(12) United States Patent
Shaaltiel et al.

(10) Patent No.: US 10,364,413 B2
(45) Date of Patent: Jul. 30, 2019

(54) LARGE SCALE DISPOSABLE BIOREACTOR

(75) Inventors: Yoseph Shaaltiel, Doar-Na HaMovil (IL); Yair Kirshner, Doar-Na Bikat Beith HaKerem (IL); Alon Shtainiz, Doar-Na Misgav (IL); Yaron Naos, Doar-Na HaMovil (IL); Yftach Shneor, Doar-Na Oshrat (IL)

(73) Assignee: Protalix Ltd., Carmiel (IL)

( * ) Notice: Subject to any disclaimer, the term of this patent is extended or adjusted under 35 U.S.C. 154(b) by 1364 days.

(21) Appl. No.: 12/451,295

(22) PCT Filed: May 5, 2008

(86) PCT No.: PCT/IL2008/000614
§ 371 (c)(1),
(2), (4) Date: Nov. 5, 2009

(87) PCT Pub. No.: WO2008/135991
PCT Pub. Date: Nov. 13, 2008

(65) Prior Publication Data
US 2010/0112700 A1    May 6, 2010

Related U.S. Application Data

(60) Provisional application No. 60/924,273, filed on May 7, 2007.

(51) Int. Cl.
*C12M 1/12* (2006.01)
*C12M 1/00* (2006.01)
(Continued)

(52) U.S. Cl.
CPC ............ *C12M 41/34* (2013.01); *C12M 23/00* (2013.01); *C12M 23/26* (2013.01); *C12M 23/28* (2013.01)

(58) Field of Classification Search
USPC .......... 435/292.1, 296.1, 297.5, 283.1–309.4
See application file for complete search history.

(56) References Cited

U.S. PATENT DOCUMENTS

| 467,993 A | 2/1892 | Jorgensen et al. |
|---|---|---|
| 2,147,271 A | 2/1939 | Schwarz et al. |

(Continued)

FOREIGN PATENT DOCUMENTS

| AU | 2004229070 | 6/2005 |
|---|---|---|
| CN | 1875111 | 12/2006 |

(Continued)

OTHER PUBLICATIONS

Invitation Pursuant to Rule 63(1) EPC dated Mar. 25, 2011 From the European Patent Office Re. Application No. 10012373.6.
(Continued)

*Primary Examiner* — Gautam Prakash
*Assistant Examiner* — Lydia Edwards

(57) ABSTRACT

A reusable, disposable device for culturing plant tissues or cells including a non-rigid container having dimensions and gas exchange ports designed for maintaining oxygen saturation and shear forces suitable for culturing plant tissue or cells in 400 liters or more of culture medium is provided. Also provided are methods for producing a catalytically active human recombinant protein in a plant cell, using the disposable device of one of the embodiments of the instant specification.

36 Claims, 16 Drawing Sheets
(11 of 16 Drawing Sheet(s) Filed in Color)
Specification includes a Sequence Listing.

(51) Int. Cl.
*C12M 3/00* (2006.01)
*C12M 1/22* (2006.01)
*C12M 1/34* (2006.01)

(56) References Cited

U.S. PATENT DOCUMENTS

| | | | |
|---|---|---|---|
| 2,341,259 A | 2/1944 | Baldwin | |
| 2,836,434 A | 5/1958 | Heden | |
| 3,201,327 A | 8/1965 | Beck | |
| 3,468,520 A | 9/1969 | Duryea et al. | |
| 3,504,185 A | 3/1970 | Zweig et al. | |
| 3,540,700 A | 11/1970 | Freedman et al. | |
| 3,705,082 A | 12/1972 | Hondermarck et al. | |
| 3,743,582 A | 7/1973 | Kitai et al. | |
| 3,793,154 A | 2/1974 | Efthymiou | |
| 3,806,423 A | 4/1974 | Karrenbauer et al. | |
| 3,950,227 A | 4/1976 | Efthymiou | |
| 4,179,339 A | 12/1979 | Sogi et al. | |
| 4,228,243 A | 10/1980 | Iizuka | |
| 4,328,317 A | 5/1982 | Prentice et al. | |
| 4,425,908 A | 1/1984 | Simon | |
| 4,491,549 A * | 1/1985 | Fischer et al. | 261/36.1 |
| 4,519,984 A | 5/1985 | Hitzman | |
| 4,577,631 A | 3/1986 | Kreamer | |
| 4,619,246 A | 10/1986 | Mølgaard-Nielsen et al. | |
| 4,643,184 A | 2/1987 | Mobin-Uddin | |
| 4,655,771 A | 4/1987 | Wallsten | |
| 4,668,632 A | 5/1987 | Young et al. | |
| 4,708,938 A | 11/1987 | Hickinbotham | |
| 4,713,345 A | 12/1987 | Ramsden | |
| 4,717,668 A | 1/1988 | Keilman et al. | |
| 4,725,548 A | 2/1988 | Karrer | |
| 4,760,849 A | 8/1988 | Kropf | |
| 4,888,294 A | 12/1989 | Van Wezel et al. | |
| 4,908,315 A | 3/1990 | Kertz | |
| 4,931,401 A | 6/1990 | Safi | |
| 4,954,126 A | 9/1990 | Wallsten | |
| 5,043,283 A | 8/1991 | Endo et al. | |
| 5,061,275 A | 10/1991 | Wallsten et al. | |
| 5,073,491 A | 12/1991 | Familletti | |
| 5,081,036 A | 1/1992 | Familletti | |
| 5,100,801 A | 3/1992 | Ward et al. | |
| 5,166,072 A | 11/1992 | Krauling et al. | |
| 5,188,946 A | 2/1993 | Ward et al. | |
| 5,225,346 A | 7/1993 | Matsumiya et al. | |
| 5,240,598 A | 8/1993 | Portier et al. | |
| 5,246,855 A | 9/1993 | Katinger et al. | |
| 5,267,791 A | 12/1993 | Christian et al. | |
| 5,324,304 A | 6/1994 | Rasmussen | |
| 5,342,781 A | 8/1994 | Su | |
| 5,350,398 A | 9/1994 | Pavcnik et al. | |
| 5,367,110 A | 11/1994 | Galili | |
| 5,372,945 A | 12/1994 | Alchas et al. | |
| 5,383,392 A | 1/1995 | Kowalewski et al. | |
| 5,409,833 A | 4/1995 | Hu et al. | |
| 5,415,630 A | 5/1995 | Gory et al. | |
| 5,443,497 A | 8/1995 | Venbrux | |
| 5,456,712 A | 10/1995 | Maginot | |
| 5,464,449 A | 11/1995 | Ryan et al. | |
| 5,534,417 A | 7/1996 | Arad et al. | |
| 5,549,626 A | 8/1996 | Miller et al. | |
| 5,549,892 A | 8/1996 | Friedman et al. | |
| 5,562,725 A | 10/1996 | Schmitt et al. | |
| 5,565,015 A | 10/1996 | Kobayashi | |
| 5,612,188 A | 3/1997 | Shuler et al. | |
| 5,725,568 A | 3/1998 | Hastings | |
| 5,769,816 A | 6/1998 | Barbut et al. | |
| 5,800,514 A | 9/1998 | Nunez et al. | |
| 5,807,330 A | 9/1998 | Teitelbaum | |
| 5,817,126 A | 10/1998 | Imran | |
| 5,843,089 A | 12/1998 | Sahatjian et al. | |
| 5,843,172 A | 12/1998 | Yan | |
| 5,853,419 A | 12/1998 | Imran | |
| 5,855,599 A | 1/1999 | Wan | |
| 5,871,537 A | 2/1999 | Holman et al. | |
| 5,876,367 A | 3/1999 | Kaganov et al. | |
| 5,891,191 A | 4/1999 | Stinson | |
| 5,904,714 A | 5/1999 | Nunez et al. | |
| 5,922,019 A | 7/1999 | Hankh et al. | |
| 5,928,260 A | 7/1999 | Chin et al. | |
| 5,928,261 A | 7/1999 | Ruiz | |
| 5,929,304 A | 7/1999 | Radin et al. | |
| 5,941,896 A | 8/1999 | Kerr | |
| 5,951,599 A | 9/1999 | McCrory | |
| 5,964,798 A | 10/1999 | Imran | |
| 5,976,169 A | 11/1999 | Imran | |
| 5,980,555 A | 11/1999 | Barbut et al. | |
| 6,022,374 A | 2/2000 | Imran | |
| 6,027,529 A | 2/2000 | Roychowdhury et al. | |
| 6,030,414 A | 2/2000 | Taheri | |
| 6,053,932 A | 4/2000 | Daniel et al. | |
| 6,054,637 A | 4/2000 | Boller et al. | |
| 6,059,823 A | 5/2000 | Holman et al. | |
| 6,071,306 A | 6/2000 | Angelini | |
| 6,083,725 A | 7/2000 | Selden et al. | |
| 6,086,577 A | 7/2000 | Ken et al. | |
| 6,093,199 A | 7/2000 | Brown et al. | |
| 6,096,546 A | 8/2000 | Raskin | |
| 6,136,022 A | 10/2000 | Nunez et al. | |
| 6,146,370 A | 11/2000 | Barbut | |
| 6,190,913 B1 | 2/2001 | Singh | |
| 6,193,708 B1 | 2/2001 | Ken et al. | |
| 6,193,748 B1 | 2/2001 | Thompson et al. | |
| 6,194,560 B1 | 2/2001 | Arntzen et al. | |
| 6,210,166 B1 | 4/2001 | Jenkins et al. | |
| 6,258,115 B1 | 7/2001 | Dubrul | |
| 6,258,120 B1 | 7/2001 | McKenzie et al. | |
| 6,261,305 B1 | 7/2001 | Marotta et al. | |
| 6,309,413 B1 | 10/2001 | Dereume et al. | |
| 6,312,463 B1 | 11/2001 | Rourke et al. | |
| 6,348,063 B1 | 2/2002 | Yassour et al. | |
| 6,383,171 B1 | 5/2002 | Gifford et al. | |
| 6,391,638 B1 | 5/2002 | Shaaltiel | |
| 6,409,750 B1 | 6/2002 | Hyodoh et al. | |
| 6,409,757 B1 | 6/2002 | Trout, III et al. | |
| 6,432,698 B1 | 8/2002 | Gaugler et al. | |
| 6,458,152 B1 | 10/2002 | Khosravi et al. | |
| 6,475,208 B2 | 11/2002 | Mauch | |
| 6,488,704 B1 | 12/2002 | Connelly et al. | |
| 6,499,487 B1 | 12/2002 | McKenzie et al. | |
| 6,533,811 B1 | 3/2003 | Ryan et al. | |
| 6,576,009 B2 | 6/2003 | Ryan et al. | |
| 6,638,294 B1 | 10/2003 | Palmer | |
| 6,673,089 B1 | 1/2004 | Yassour et al. | |
| 6,709,862 B2 | 3/2004 | Curtis | |
| 6,740,112 B2 | 5/2004 | Yodfat et al. | |
| 6,815,184 B2 | 11/2004 | Stomp et al. | |
| 6,846,968 B1 | 1/2005 | Erwin et al. | |
| 6,866,680 B2 | 3/2005 | Yassour et al. | |
| 7,329,539 B2 | 2/2008 | Hong et al. | |
| 7,572,290 B2 | 8/2009 | Yodfat et al. | |
| 7,655,781 B2 | 2/2010 | Shemesh et al. | |
| 7,951,557 B2 | 5/2011 | Shaaltiel et al. | |
| 8,449,876 B2 | 5/2013 | Shaaltiel et al. | |
| 2002/0015708 A1 | 2/2002 | Stram et al. | |
| 2002/0088024 A1 | 7/2002 | Larger et al. | |
| 2002/0110915 A1 | 8/2002 | Shaaltiel | |
| 2002/0127219 A1 | 9/2002 | Okkels et al. | |
| 2003/0077806 A1 | 4/2003 | Selden et al. | |
| 2003/0100945 A1 | 5/2003 | Yodfat et al. | |
| 2003/0125801 A1 | 7/2003 | Yodfat et al. | |
| 2003/0175948 A1 * | 9/2003 | Hong et al. | 435/289.1 |
| 2004/0010307 A1 | 1/2004 | Grad et al. | |
| 2004/0010308 A1 | 1/2004 | Zafrir-Pachter et al. | |
| 2004/0024416 A1 | 2/2004 | Yodfat et al. | |
| 2004/0133266 A1 | 7/2004 | Clerc et al. | |
| 2004/0167613 A1 | 8/2004 | Yodfat et al. | |
| 2005/0010281 A1 | 1/2005 | Yodfat et al. | |
| 2005/0023198 A1 | 2/2005 | Halemba | |
| 2005/0032211 A1 | 2/2005 | Shaaltiel | |
| 2005/0272146 A1 * | 12/2005 | Hodge et al. | 435/289.1 |
| 2005/0281805 A1 | 12/2005 | LeBowitz et al. | |
| 2005/0282269 A1 * | 12/2005 | Proulx | 435/296.1 |
| 2006/0204487 A1 | 9/2006 | Shaaltiel et al. | |

(56) References Cited

U.S. PATENT DOCUMENTS

| | | |
|---|---|---|
| 2008/0038232 A1 | 2/2008 | Shaaltiel et al. |
| 2008/0039933 A1 | 2/2008 | Yodfat et al. |
| 2008/0132743 A1 | 6/2008 | Mack et al. |
| 2009/0053743 A1 | 2/2009 | Link et al. |
| 2009/0053762 A1 | 2/2009 | Shaaltiel |
| 2009/0082548 A1 | 3/2009 | Shaalticl et al. |
| 2009/0208477 A1 | 8/2009 | Shaaltiel et al. |
| 2009/0270970 A1 | 10/2009 | Yodfat et al. |
| 2010/0112700 A1 | 5/2010 | Shaaltiel et al. |
| 2010/0136673 A1 | 6/2010 | Shaaltiel |
| 2011/0250181 A1 | 10/2011 | Schaaltiel et al. |
| 2012/0282231 A1 | 11/2012 | Shaaltiel et al. |
| 2013/0177538 A1 | 7/2013 | Shaaltiel et al. |

FOREIGN PATENT DOCUMENTS

| | | |
|---|---|---|
| CN | 1946835 | 4/2007 |
| DE | 2654725 | 8/1977 |
| DE | 69718812 | 1/2003 |
| EP | 0183372 | 6/1984 |
| EP | 0200792 | 12/1986 |
| EP | 0343885 | 11/1989 |
| EP | 0350723 | 1/1990 |
| EP | 0447256 | 9/1991 |
| EP | 0462065 | 12/1991 |
| EP | 0713966 | 5/1996 |
| EP | 0880948 | 12/1998 |
| EP | 0938544 | 1/2003 |
| GB | 1053848 | 1/1967 |
| GB | 2202549 | 9/1988 |
| IN | 227249 | 1/2009 |
| JP | 63-109772 | 5/1988 |
| JP | 02-119771 | 5/1990 |
| JP | 08-503615 | 4/1996 |
| JP | 10-084802 | 4/1998 |
| JP | 10-507916 | 8/1998 |
| JP | 11-012143 | 1/1999 |
| JP | 2000-053549 | 2/2000 |
| JP | 2000-128752 | 5/2000 |
| JP | 2001-502526 | 2/2001 |
| JP | 2002-238580 | 8/2002 |
| JP | 2002-526116 | 8/2002 |
| JP | 2003-180354 | 7/2003 |
| JP | 04-229182 | 2/2006 |
| JP | 2006-524506 | 11/2006 |
| JP | 1946835 | 4/2007 |
| JP | 2007-511231 | 5/2007 |
| NL | 1012782 | 4/2001 |
| RU | 2140986 | 11/1999 |
| WO | WO 88/00234 | 1/1988 |
| WO | WO 94/12628 | 6/1994 |
| WO | WO 96/12801 | 5/1996 |
| WO | WO 96/13599 | 5/1996 |
| WO | WO 96/21723 | 7/1996 |
| WO | WO 97/10353 | 3/1997 |
| WO | WO 98/13469 | 4/1998 |
| WO | WO 98/47447 | 10/1998 |
| WO | WO 98/58599 | 12/1998 |
| WO | WO 99/02092 | 1/1999 |
| WO | WO 99/07210 | 2/1999 |
| WO | WO 99/32050 | 7/1999 |
| WO | WO 00/20612 | 4/2000 |
| WO | WO 00/53118 | 9/2000 |
| WO | WO 00/53119 | 9/2000 |
| WO | WO 01/49830 | 7/2001 |
| WO | WO 02/05729 | 1/2002 |
| WO | WO 02/08404 | 1/2002 |
| WO | WO 02/15927 | 2/2002 |
| WO | WO 02/40686 | 5/2002 |
| WO | WO 02/68666 | 6/2002 |
| WO | WO 02/055123 | 7/2002 |
| WO | WO 02/055125 | 7/2002 |
| WO | WO 02/083888 | 10/2002 |
| WO | WO 03/006097 | 1/2003 |
| WO | WO 2003/013598 | 2/2003 |
| WO | WO 03/043527 | 5/2003 |
| WO | WO 03/073839 | 9/2003 |
| WO | WO 2004/003207 | 1/2004 |
| WO | WO 2004/005480 | 1/2004 |
| WO | WO 2004/096978 | 11/2004 |
| WO | WO 2005/080544 | 1/2005 |
| WO | WO 2005/049784 | 6/2005 |
| WO | WO 2005/080544 | 9/2005 |
| WO | WO 2005/118771 | 12/2005 |
| WO | WO 2006/038209 | 4/2006 |
| WO | WO 2006/040764 | 4/2006 |
| WO | WO 2006/116067 | 11/2006 |
| WO | WO 2007/005882 | 1/2007 |
| WO | WO 2007/010533 | 1/2007 |
| WO | WO 2007/134141 | 11/2007 |
| WO | WO 2008/088371 | 7/2008 |
| WO | WO 2008/132743 | 11/2008 |
| WO | WO 2008/135991 | 11/2008 |

OTHER PUBLICATIONS

Response dated Apr. 19, 2011 to Invitation Pursuant to Rule 63(1) EPC of Mar. 25, 2011 From the European Patent Office Re. Application No. 10012373.6.
Response dated Dec. 22, 2011 to Notice of the Reason for Rejection dated Sep. 7, 2011 From the Korean Intellectual Property Office (KIPO) Re. Application No. 2011-7014421.
Response dated Dec. 22, 2011 to Written Opinion dated Jul. 26, 2011 From the Intellectual Property Office of Singapore, Issued by the Hungarian Patent Office on Apr. 6, 2011 Re. Application No. 2009073719.
Office Action dated Dec. 22, 2011 From the U.S. Patent and Trademark Office Re. U.S. Appl. No. 13/008,048.
Response dated Jan. 1, 2012 to European Search Report and the European Search Opinion dated May 27, 2011 From the European Patent Office Re. Application No. 10012373.6.
Supplementary European Search Report and the European Search Opinion dated Dec. 16, 2010 From the European Patent Office Re. Application No. 08738278.4.
Translation of Notice of Reason for Rejection dated Jan. 4, 2011 From the Japanese Patent Office Re.: Application No. 2006-507577.
Davis et al. "MemO: A Consensus Approach to the Annotation of a Protein's Membrane Organization", In Silico Biology, XP009141065, 6(5): 387-399, 2006. p. 391-392, 395, 397.
Strous et al. "Differential Effects of Brefeldin A on Transport of Secretory and Lysomal Proteins", The Journal of Biological Chemistry, XP009141068, 268(4): 2341-2347, Feb. 5, 1993. Abstract.
Communication Pursuant to Article 94(3) EPC dated Jan. 20, 2012 From the European Patent Office Re. Application No. 10012376.9.
Office Action dated Dec. 22, 2011 From the Israeli Patent Office Re.: Application No. 171561 and Its Translation Into English.
Examination Report dated Jun. 18, 2010 From the Instituto Mexicano de la Propriedad Industrial Re.: Application No. PA/a/2006/009612.
Notice of Acceptance dated Dec. 8, 2010 From the South African Patent Office Re. Application No. 2009/07804.
Response dated Jan. 9, 2011 to Notice of Acceptance dated Dec. 8, 2010 From the South African Patent Office Re. Application No. 2009/07804.
Communication Pursuant to Article 94(3) EPC dated Jan. 30, 2012 From the European Patent Office Re. Application No. 10012372.8.
Examination Report dated Jan. 12, 2012 From the Federal Institute of Industrial Property of the Federal Service for Intellectual Property, Patents and Trademark of the Russian Federation Re. Application No. 2009143751 and Its Summary in English.
Translation of Notice of Reason for Rejection dated Jan. 31, 2012 From the Japanese Patent Office Re.: Application No. 2006-507577.
Translation of Notice of Reason for Rejection dated May 20, 2011 From the Japanese Patent Office Re. Application No. 2007-500352.
European Search Report and the European Search Opinion dated May 27, 2011 From the European Patent Office Re. Application No. 10012373.6.
Notice of Allowance dated May 20, 2011 From the Instituto Mexicano de la Propriedad Industrial Re.: Application No. PA/a/2006/009612.

(56) References Cited

OTHER PUBLICATIONS

Office Action dated Jun. 9, 2011 From the U.S. Patent and Trademark Office Re. U.S. Appl. No. 13/008,048.
Requisition by the Examiner dated May 31, 2011 From the Canadian Intellectual Property Office Re. Application No. 2,557,525.
Requisition by the Examiner dated Dec. 9, 2010 From the Canadian Intellectual Property Office Re. Application No. 2,523,539.
Response dated Jun. 1, 2011 to Requisition by the Examiner of Dec. 9, 2010 From the Canadian Intellectual Property Office Re. Application No. 2,523,539.
Response dated May 26, 2011 to Invitation Pursuant to Article 94(3) and Rule 71(1) EPC of Mar. 31, 2011 From the European Patent Office Re.: Application No. 04713966.2.
Response dated Jun. 29, 2010 to Office Action dated May 19, 2010 From the State Intellectual Property Office of the People's Republic of China Re.: Application No. 200480017916.2.
Search Report and Written Opinion dated Mar. 18, 2010 From the Intellectual Property Office of Singapore issued by the Hungarian Patent Office Re. Application No. 2009073719.
Response dated Jul. 6, 2010 to Official Action dated Apr. 6, 2010 From the U.S. Patent and Trademark Office Re. U.S. Appl. No. 11/979,813.
Response dated Jun. 9, 2011 to the Notice of the Reason for Rejection of Mar. 12, 2011 From the Korean Intellectual Property Office Re. Application No. 2005-7020434.
Invitation to Repond to Written Opinion and Search Report dated Jun. 18, 2010 Issued by the Hungarian Patent Office at May 13, 2010 From the Intellectual Property Office of Singapore Re. Application No. 200907212-5.
Summons to Attend Oral Proceedings Pursuant to Rule 115(1) EPC dated Jul. 23, 2010 From the European Patent Office Re.: Application No. 04713966.2.
Communication Pursuant to Article 96(2) EPC dated Oct. 5, 2011 From the European Patent Office Re.: Application No. 08738278.4.
Examination Report dated Sep. 5, 2011 From the Instituto Mexicano de la Propriedad Industrial Re. Application No. MX/a/2009/011751 and Its Summary in English.
Translation of Notice of Reason for Rejection dated Sep. 16, 2011 From the Japanese Patent Office Re. Application No. 2007-500352.
Tsuji et al. "Alpha-Galactosidase [*Homo Sapiens*]", GenBank EMBL, Version CAA29232.1, GI:757912, Accession No. CAA29232.
Translation of Notice of the Reason for Rejection dated Sep. 7, 2011 From the Korean Intellectual Property Office (KIPO) Re. Application No. 2011-7014421.
Examination Report dated Aug. 12, 2005 From the Government of India, Patent Office Re.: Application No. 631/del/2001.
Examiner's Report dated Dec. 1, 2008 From the Australian Government, IP Australia Re.: Application No. 2004234635.
Examiner's Report dated Jan. 5, 2010 From the Australian Patent Office Re.: Application No. 2004234635.
Examiner's Report dated Jan. 18, 2010 From the Australian Government, IP Australia Re. Application No. 2007201909.
Formal Examination dated Jan. 26, 2010 From the ROSPATENT, Federal State Office , Federal Institution of Industrial Property of the Federal Office of Intellectual Property, Patents and Trademarks of the Russian Federation Re.: Application No. 2009148012 and Its Summary Into English.
International Preliminary Report on Patentability dated Apr. 12, 2007 From the International Preliminary Examining Authority Re.: Application No. PCT/IL04/00181.
International Preliminary Report on Patentability dated Nov. 19, 2009 From the International Bureau of WIPO Re.: Application No. PCT/IL2008/000614.
International Preliminary Report on Patentability dated Apr. 21, 2006 From the Internatinoal Preliminary Examining Authority Re.: Application No. PCT/IL2005/000228.
International Preliminary Report on Patentability dated Mar. 23, 2006 From the International Bureau of WIPO Re.: Application No. PCT/IL2004/000181.

International Preliminary Report on Patentability dated Apr. 29, 2010 From the International Bureau of WIPO Re.: Application No. PCT/IL2008/000576.
Office Action dated Jan. 6, 2010 From the Israel Patent Office Re.: Application No. 177586 and Its Translation Into English.
Official Action dated Mar. 8, 2010 From the U.S. Patent and Trademark Office Re.: U.S. Appl. No. 11/790,991.
Official Action dated Mar. 9, 2010 From the U.S. Patent and Trademark Office Re.: U.S. Appl. No. 12/385,894.
Official Action dated Feb. 18, 2010 From the Its Patent and Trademark Office Re.: U.S. Appl. No. 10/554,387.
Requisition by the Examiner dated Aug. 3, 2006 From the Canadian Intellectual Property Office Re.: Application No. 2,266,851.
Response dated Jun. 6, 2010 to Office Action dated Jan. 6, 2010 From the Israel Patent Office Re.: Application No. 177586.
Response dated Mar. 18, 2010 to Notice of Reason for Rejection of Dec. 4, 2009 From the Japanese Patent Office Re.: Application No. 2006-507577.
Response dated Mar. 22, 2010 to Examiner's Report dated Jan. 5, 2010 From the Australian Patent Office Re.: Application No. 2004234635.
Response dated Jul. 27, 2009 to Official Action dated Apr. 8, 2009 From the U.S. Patent and Trademark Office Re.: U.S. Appl. No. 10/554,387.
Response dated Nov. 30, 2009 to Examiner's Report of Dec. 1, 2008 From the Australian Government, IP Australia Re.: Application No. 2004234635.
Search Report dated Dec. 23, 2008 From the Intellectual Property Office of Singapore Issued by the Australian Patent Office Re.: Application No. SG 200800359-2.
Supplementary Partial European Search Report dated Mar. 7, 2007 From the European Patent Office Re.: Application No. 04713966.2.
Translation of Office Action dated May 19, 2010 From the State Intellectual Property Office of the People's Republic of China Re.: Application No. 200480017916.2.
Berg-Fussman et al. "Human Acid β-Glucosidase. N-Glycosylation Site Occupancy and the Effect of Glycosylation on Enzymatic Activity", The Journal of Biological Chemistry, 268(20): 14861-14866, Jul. 15, 1993.
ExPASy "NiceZyme View of Enzyme: EC 3.2.1.45", UniProtKB/Swiss-Prot, ExPASy, 2008.
Hayes et al. "Remodelled, Recombinant Glucocerebrosidase (r-GCR)", Accession AAW07885, Jan. 28, 1997.
Hein et al. "Evaluation of Immunoglobulins From Plant Cells", Biotechnology Progress, 7(5): 455-461, 1991.
Hood et al. "Plant Binary Vector P1G121-Hm DNA, Complete Sequence", GenBank Nucleotide, Accession No. AB489142.1, 2009.
Jefferson et al. "GUS Fusions: β-Glucuronidase as a Sensitive and Versatile Gene Fusion Marker in Higher Plants", The EMBO Journal, 6(13): 3901-3907, 1987.
Martin et al. "Glucosylceramidase Precursors (Beta-Glucocerebrosidase) (Acid Beta-Glucosidase) (D-Glucosyl-N-Acylsphingosine Glucohydrolase)", Fed. Proc., 43, 1984, GenBank NCBI Accession No. P04062, UniProtKB: Locus GLCM_HUMAN, GI: 121283, Apr. 1, 1993.
Schähs et al. "Production of a Monoclonal Antibody in Plants With a Humanized N-Glycosylation Pattern", Plant Biotechnology Journal, 5(5): 657-663, Sep. 2007. Abstract.
Sorge et al. "Molecular Cloning and Nucleotide Sequence of Human Glucocerebrosidase cDNA", Proc. Natl. Acad. Sci. USA, 82: 7289-7293, Nov. 1985.
Tsuji et al. "Nucleotide Sequence of cDNA Containing the Complete Cosing Sequence for Human Lysosomal Glucocerebrosidase", The Journal of Biological Chemistry, 261(1): 50-53, Jan. 5, 1986.
Witkowski et al. "Conversion of a β-Ketoacyl Synthase to a Malonyl Decarboxylase by Replacement of the Active-Site Cysteine With Glutamine", Biochemistry, 38(36): 11643-11650, 1999.
Official Action dated Oct. 29 2010 From the U.S. Patent and Trademark Office Re.: U.S. Appl. No. 10/554,387.
Communication Pursuant to Rules 70(2) and 70a(2) EPC and Reference to Rule 39(1) EPC dated Jul. 19, 2011 From the European Patent Office Re. Application No. 10012373.6.

(56) References Cited

OTHER PUBLICATIONS

Invitation to Repond to Written Opinion and Search Report dated Feb. 11, 2011 Issued by the Hungarian Patent Office at Jan. 21, 2011 From the Intellectual Property Office of Singapore Re. Application No. 200907212-5.
Response dated Aug. 3, 2011 to Notice of Reason for Rejection dated May 20, 2011 From the Japanese Patent Office Re. Application No. 2007-500352.
Response dated Jul. 7, 2011 to Examination Report dated Apr. 7, 2011 From the Instituto Mexicano de la Propriedad Industrial Re. Application No. PA/a/2005/011507.
Response dated Jul. 7, 2011 to Invitation to Repond to Written Opinion and Search Report dated Feb. 11, 2011 From the Intellectual Property Office of Singapore Re. Application No. 200907212-5.
Response dated Jul. 12, 2011 to Supplementary European Search Report and the European Search Opinion dated Dec. 16, 2010 From the European Patent Office Re. Application No. 08738278.4.
Response dated Jul. 21, 2011 to Invitation Pursuant to Article 94(3) and Rule 71(1) EPC dated Jun. 17, 2011 From the European Patent Office Re.: Application No. 04713966.2.
Office Action dated Jul. 15, 2010 From the Israel Patent Office Re.: Application No. 177586 and Its Translation Into English.
Gomord et al. "Plant-Specific Glycosylation Patterns in the Context of Therapeutic Protein Production", Plant Biotechnology Journal, 8: 564-587, 2010.
Holwerda et al. "In Vitro Processing of Aleurain, A Barley Vacuolar Thiol Protease", The Plant Cell, 2: 1091-1106, Nov. 1990.
Holwerda et al. "Proaleurain Vacuolar Targeting Is Mediated by Short Contiguous Peptide Interactions", The Plant Cell, 4: 307-318, Mar. 1992.
Neuhaus et al. "A Short C-Terminal Sequence Is Necessary and Sufficient for the Targeting of Chitinases to the Plant Vacuole (Cucumber / Nicotiana Silvestris / Nicotiana Tabacum / Plant Defense / Secretion)", Proc. Natl. Acad. Sci. USA, 88: 10362-10366, Nov. 1991.
Neuhaus et al. "Sorting of Proteins to Vacuoles in Plant Cells", Plant Molecular Biology, 38: 127-144, 1998.
Official Action dated Aug. 17, 2010 From the U.S. Patent and Trademark Office Re.: U.S. Appl. No. 11/979,813.
Response dated Aug. 17, 2010 to Official Actiondated Feb. 18, 2010 From the U.S. Patent and Trademark Office Re.: U.S. Appl. No. 10/554,387.
Alfermann et al. "Natural Product Formation by Plant Cell Biotechnology. Results and Perspectives", Plant Cell, Tissue and Organ Culture, 43: 199-205, 1995.
Gomez et al. "Tonoplast and Soluble Vacuolar Proteins Are Targeted by Different Mechanisms", The Plant Cell, 5: 1113-1124, Sep. 1993.
Hardegger et al. "Transformation and Regeneration of Carrot (*Daucus carona* L.)", Molecular Breeding, 4: 119-127, 1998.
Horowitz "Human Glucocerebrosidase mRNA, Complete Cds", GenBank Nucleotide, Accession No. M19285.1, 1993.
Ozeki et al. "Effects of Inoculum Density, Zeatin and Sucrose on Anthocyanin Accumulation in a Carrot Suspension Culture", Plant Cell Tissue Organ Culture, 5: 45-53, 1985.
Communication Under Rule 71(3) EPC dated Dec. 1, 2011 From the European Patent Office Re.: Application No. 04713966.2.
Invitation to Respond to Written Opinion dated Aug. 17, 2010 From the Intellectual Property Office of Singapore Re. Application No. 2009073719.
Official Action dated Nov. 12, 2010 From the U.S. Patent and Trademark Office Re. U.S. Appl. No. 12/690,977.
Response dated Dec. 1, 2010 to Notice of Reason for Rejection dated Aug. 31, 2010 From the Japanese Patent Office Re. Application No. 2007-500352.
Response dated Nov. 15, 2010 to Office Action dated Jul. 15, 2010 From the Israel Patent Office Re.: Application No. 177586.
Response dated Nov. 17, 2010 to Invitation to Repond to Written Opinion and Search Report dated Jun. 18, 2010 Issued by the Hungarian Patent Office at May 13, 2010 From the Intellectual Property Office of Singapore Re. Application No. 200907212-5.

Response dated Dec. 20, 2010 to Invitation to Respond to Written Opinion dated Aug. 17, 2010 From the Intellectual Property Office of Singapore Re. Application No. 2009073719.
Response dated Nov. 22, 2010 to Official Action dated Jun. 21, 2010 From the U.S. Patent and Trademark Office Re.: U.S. Appl. No. 12/385,894.
Response dated Nov. 24, 2010 to Office Action dated Jul. 25, 2010 From the Israeli Patent Office Re.: Application No. 171561.
Response dated Nov. 28, 2010 to Examination Report dated Aug. 31, 2009 From the Australian Government, IP Australia Re.: Application No. 2005214181.
Search Report and Written Opinion dated Oct. 5, 2010 From the Intellectual Property Office of Singapore Issued by the Austrian Patent Office Re. Application No. 200717273-7.
Shaaltiel et al. "Production of Glucocerebrosidase With Terminal Mannose Glycans for Enzyme Replacement Therapy of Gaucher's Disease Using a Plant Cell System", Plant Biotechnology Journal, 5: 579-590, 2007.
Wandelt et al. "Vicilin With Carboxy-Terminal KDEL Is Retained in the Endoplasmic Reticulum and Accumulates to High Levels in the Leaves of Transgenic Plants", Plant Journal, 2(2): 181-192, Mar. 1992. Abstract.
Translation of Notice of the Reason for Rejection dated Feb. 17, 2012 From the Korean Intellectual Property Office Re. Application No. 2005-7020434.
Official Action dated Feb. 24, 2012 From the U.S. Patent and Trademark Office Re. U.S. Appl. No. 13/080,692.
Requisition by the Examiner dated Feb. 7, 2012 From the Canadian Intellectual Property Office Re. Application No. 2,523,539.
Sen et al. "Developments in Directed Evolution for Improving Enzyme Functions", Applied Biochemistry and Biotechnology, 143(3): 212-223, Dec. 2007.
Response dated Apr. 25, 2010 to Office Action dated Sep. 23, 2009 From the Israeli Patent Office Re.: Application No. 182888.
Translation of Notice of the Reason for Rejection dated Mar. 12, 2011 From the Korean Intellectual Property Office Re. Application No. 2005-7020434.
Restriction Official Action dated Mar. 12, 2012 From the U.S. Patent and Trademark Office Re.: U.S. Appl. No. 12/451,188.
Moran et al. "Fabry Kidney Disease", Saudi Journal of Kidney Diseases and Transplantation, 14(3): 367-377, 2003.
Invitation Pursuant to Article 94(3) and Rule 71(1) EPC dated Mar. 31, 2011 From the European Patent Office Re.: Application No. 04713966.2.
Response dated Feb. 14, 2011 to Examination Report dated Jun. 18, 2010 From the Instituto Mexican de la Propriedad Industrial Re.: Application No. PA/a/2006/009612.
Response dated Feb. 15, 2011 to Examiner's Report dated Jan. 18, 2010 From the Australian Government, IP Australia Re. Application No. 2007201909.
Official Action dated Apr. 5, 2012 From the U.S. Patent and Trademark Office Re. U.S. Appl. No. 13/080,694.
Examination Report dated Sep. 25, 2009 From the Instituto Mexicano de la Propriedad Industrial Re.: Application No. PA/a/2006/009612.
Official Action dated Feb. 18, 2010 From the U.S. Patent and Trademark Office Re.: U.S. Appl. No. 10/554,387.
Response dated Mar. 18, 2010 to Notice of Reason for Rejection dated Dec. 4, 2009 From the Japanese Patent Office Re.: Application No. 2006- 507577.
Official Action dated Jun. 21, 2010 From the U.S. Patent and Trademark Office Re.: U.S. Appl. No. 12/385,894.
Response dated Jun. 8, 2010 to Official Action dated Mar. 9, 2010 From the U.S. Patent and Trademark Office Re.: U.S. Appl. No. 12/385,894.
Response dated Jul. 13, 2010 to Official Action dated Mar. 29, 2010 From Rospatent, Federal State Office , Federal Institution of Industrial Property of the Federal Office of Intellectual Properly, Patents and Trademarks of the Russian Federation Re.: Application No. 2009140906.
Response dated Jul. 8, 2010 to Official Action dated Mar. 8, 2010 From the U.S. Patent and Trademark Office Re.: U.S. Appl. No. 11/790,991.

(56) References Cited

OTHER PUBLICATIONS

Examination Report dated Jun. 24, 2011 From the Government of India, Patent Office, Intellectual Property Building Re. Application No. 930/CRENP/2008.
Communication Pursuant to Article 94(3) EPC dated Feb. 12, 2009 From the European Patent Office Re.: Application No. 04713966.2.
Communication Pursuant to Article 94(3) EPC dated Oct. 16, 2009 From the European Patent Office Re.: Application No. 02785876.0.
Communication Pursuant to Article 96(2) EPC dated Oct. 31, 2007 From the European Patent Office Re.: Application No. 04713966.2.
Decision of Rejection and Decision of Dismissal of Amendment dated Sep. 25, 2009 From the Japanese Patent Office Re.: Application No. 2000-603610 and Its Translation Into English.
Examination Report dated Jun. 12, 2007 From the Government of India, Patent Office Re.: Application No. 3150/CHENP/2005.
Examination Report dated Aug. 31, 2009 From the Australian Government, IP Australia Re.: Application No. 2005214181.
Examination Request dated Aug. 16, 2007 to the Australian Government, IP Australia Re.: Application No. 2005214181.
Examiner's Report daed Dec. 1, 2008 From the Australian Government, IP Australia Re.: Application No. 2004234635.
Indication of Defiencies in a Request Under Rule 20 EPC dated Jan. 23, 2007 From the European Patent Office Re.: Application No. 02785875.2.
International Preliminary Examination Report dated Jun. 19, 2001 From the International Preliminary Examining Authority Re.: Application No. PCT/IL00/00147.
International Preliminary Report on Patentability dated Apr. 21, 2006 From the International Preliminary Examining Authority Re.: Application No. PCT/IL2005/000228.
International Search Report and the Written Opinion dated Dec. 15, 2005 From the International Searching Authority Re.: Application No. PCT/IL2005/000228.
International Search Report dated Feb. 17, 2006 From the International Searching Authority Re.: Application No. PCT/IL04/00181.
International Search Report dated May 27, 2009 From the International Searching Authority Re.: Application No. PCT/IL2008/000614.
Notice of Allowance dated Apr. 3, 2009 From the U.S. Patent and Trademark Office Re.: U.S. Appl. No. 11/907,675.
Notice of Allowance dated Oct. 16, 2009 From the U.S. Patent and Trademark Office Re.: U.S. Appl. No. 10/554,387.
Notification of the Results of the Examination dated Oct. 14, 2008 From the Patent Office of the Russian Federation Re.: Application No. 2005136874 and Its Translation Into English.
Office Action dated Nov. 1, 2005 From the Israeli Patent Office Re.: Application No. 145137.
Office Action dated Feb. 4, 2005 From the Patent Office of the People's Republic of China Re.: Application No. 01815497.2.
Office Action dated Feb. 6, 2009 From the State Intellectual Property Office of the People's Republic of China Re.: Application No. 200480017916.2.
Office Action dated Dec. 10, 2008 From the Israeli Patent Office Re.: Application No. 171561 and Its Translation Into English.
Office Action dated Jan. 10, 2007 From the Israeli Patent Office Re.: Application No. 145138.
Office Action dated May 10, 2006 From the Israeli Patent Office Re.: Application No. 140871.
Office Action dated Nov. 12, 2006 From the Israeli Patent Office Re.: Application No. 145137.
Office Action dated Nov. 12, 2006 From the Israeli Patent Office Re.: Application No. 145138.
Office Action dated Sep. 23, 2009 From the Israeli Patent Office Re.: Application No. 182888 and Its Translation Into English.
Office Action dated Jan. 27, 2005 From the Israeli Patent Office Re.: Application No. 137326.
Office Letter dated Jan. 14, 2008 From the Government of India, Patent Office Re.: Application No. 3150/CHENP/2005.
Official Action dated Jul. 1, 2008 From the U.S. Patent and Trademark Office Re.: U.S. Appl. No. 10/311,876.
Official Action dated Nov. 1, 2006 From the U.S. Patent and Trademark Office Re.: U.S. Appl. No. 10/311,876.
Official Action dated Oct. 4, 2004 From the U.S. Patent and Trademark Office Re.: U.S. Appl. No. 10/311,876.
Official Action dated Jun. 6. 2007 From the U.S. Patent and Trademark Office Re.: U.S. Appl. No. 10/216,356.
Official Action dated Jun. 6, 2008 From the U.S. Patent and Trademark Office Re.: U.S. Appl. No. 11/790,991.
Official Action dated Dec. 7, 2007 From the U.S. Patent and Trademark Office Re.: U.S. Appl. No. 10/311,876.
Official Action dated Apr. 8, 2009 From the U.S. Patent and Trademark Office Re.: U.S. Appl. No. 10/554,387.
Official Action dated Jan. 8, 2008 From the U.S. Patent and Trademark Office Re.: U.S. Appl. No. 10/784,295.
Official Action dated Jan. 9, 2008 From the U.S. Patent and Trademark Office Re.: U.S. Appl. No. 10/554,387.
Official Action dated Oct. 9, 2008 From the U.S. Patent and Trademark Office Re.: U.S. Appl. No. 10/311,876.
Official Action dated Jul. 10, 2008 From the U.S. Patent and Trademark Office Re.: U.S. Appl. No. 11/907,675.
Official Action dated Apr. 12, 2007 From the U.S. Patent and Trademark Office Re.: U.S. Appl. No. 10/910,621.
Official Action dated Mar. 12, 2007 From the U.S. Patent and Trademark Office Re.: U.S. Appl. No. 10/311,876.
Official Action dated Nov. 14, 2008 From the U.S. Patent and Trademark Office Re.: U.S. Appl. No. 10/784,295.
Official Action dated Oct. 14, 2009 From the U.S. Patent and Trademark Office Re.: U.S. Appl. No. 11/790,991.
Official Action dated Jun. 18, 2007 From the U.S. Patent and Trademark Office Re.: U.S. Appl. No. 10/784,295.
Official Action dated Jul. 21, 2008 From the U.S. Patent and Trademark Office Re.: U.S. Appl. No. 10/554,387.
Official Action dated Jul. 22, 2009 From the U.S. Patent and Trademark Office Re.: U.S. Appl. No. 10/784,295.
Official Action dated Aug. 23, 2006 From the U.S. Patent and Trademark Office Re.: U.S. Appl. No. 10/615,945.
Official Action dated Feb. 25, 2009 From the U.S. Patent and Trademark Office Re.: U.S. Appl. No. 10/311,876.
Official Action dated Sep. 26, 2008 From the U.S. Patent and Trademark Office Re.: U.S. Appl. No. 11/790,991.
Official Action dated Jan. 29, 2008 From the U.S. Patent and Trademark Office Re.: U.S. Appl. No. 11/790,991.
Official Action dated Jun. 29, 2005 From the U.S. Patent and Trademark Office Re.: U.S. Appl. No. 10/311,876.
Official Action dated Oct. 31, 2008 From Patent Office of the Russian Federation Re.: 2007147328/15(051871).
Protocol dated Jun. 17, 2009 From the Patent Office of the Russian Federation Re.: Application No. 2005136874 and a Summary in English.
Response dated Jul. 28, 2003 to Official Action dated Apr. 1, 2003 From the U.S. Patent and Trademark Office Re.: U.S. Appl. No. 10/216,356.
Response dated Nov. 30, 2009 to Examiner's Report dated Dec. 1, 2008 From the Australian Government, IP Australia Re.: Application No. 2004234635.
Summons to Attend Oral Proceedings Pursuant to Rule 115(1) EPC dated Dec. 9, 2008 From the European Patent Office Re.: Application No. 00909599.3.
Supplementary Partial European Search Report dated Jun. 23, 2009 From the European Patent Office Re.: Application No. 02785876.0.
Translation of Notice of Reason for Rejection dated Dec. 4, 2009 From the Japanese Patent Office Re.: Application No. 2006-507577.
Translation of Notification of Reason for Rejection dated Apr. 11, 2008 From the Japanese Patent Office Re.: Application No. 2000-603610.
Translation of Office Action dated Nov. 6, 2009 From the State Intellectual Property Office of the People's Republic of China Re.: Application No. 200480017916.2.
Translation of Request dated Mar. 24, 2009 From the Patent Office of Ukraine Re.: Application No. 200511193.
Translation of the Office Action dated Aug. 31, 2007 Form the Patent Office of the People's Republic of China Re.: Application No. 200480017916.2.

(56) References Cited

OTHER PUBLICATIONS

Translation of the Official Action dated Jan. 16, 2007 From the Japanese Patent Office Re.: Application No. 515465/98.
Written Opinion dated Feb. 17, 2006 From the International Searching Authority Re.: Application No. PCT/IL04/00181.
Written Opinion dated Dec. 23, 2008 From the Intellectual Property Office of Singapore Issued by the Australian Patent Office Re.: Application No. SG 200800359-2.
Written Opinion dated May 27, 2009 From the International Searching Authority Re.: Application No. PCT/IL2008/000614.
Barnett et al. "Causes and Severtity of Ischemic Stroke in Patients With Internal Carotid Artery Stenosis", JAMA, 283: 1429-1436, 2000.
Barton et al. "Therapeutic Response to Intravenous Infusions of Glucocerebrosidase in a Patient With Gaucher Disease", Proc. Natl. Acad. Sci. USA, 87: 1913-1916, Mar. 1990.
Boller et al. "DNA Sequence Encoding Vacuole Targetting Peptide—Esp. Signal Region of Tobacco Chitinase or Glucanase Gene, and Derived Recombinant DNA, Vectors, Etc. Functional in Plants", Database GenBank, US National Library of Medicine, No. AAR15823, 2003.
Branden et al. "Prediction, Engineering, and Design of Protein Structures", Introduction to Protein Structure, Garland Publishing, p. 247, 1991.
Caplan "Multiple Potential Risks for Stroke", JAMA, 283(11): 1479-1480, 2000.
Chica et al. "Semi-Rational Approaches to Engineering Enzyme Activity: Combining the Benefits of Directed Evolution and Rational Design", Current Opinion in Biotechnology, 16: 378-384, 2005.
Cramer et al. "Transgenic Plants for Therapeutic Proteins: Linking Upstream and Downstream Strategies", Current Topics in Microbiology and Immunology, 240: 95-118, 1999. p. 109-112, § 1.
Crooy et al. "Recombinant. Glucocerebrosidase and Lyme Disease Vaccine Made by Genetic Engineering (No. 11 in a Series of Articles to Promote a Better Understanding of the Use of Genetic Engineering", Journal of Biotechnology, 76: 259-263, 2000.
Dulk-Ra et al. "Electroporation of Agrobacterium Tumefaciens ", Methods in Molecular Biology, 55: 63-72, 1995. Abstract.
Erickson et al. "Biosynthesis of the Lysosomal Enzyme Glucocerebrosidase", The Journal of Biological Chemistry, 260(26): 14319-14324, 1985.
ExPASy "NiceZyme View of Enzyme: EC 3.2.1.45", UniProtKB/Swiss-Prot, ExPASy. http://us.expasy.org/enzyme/3.2.1.45.
Fischer et al. "Molecular Farming of Pharmaceutical Proteins", Transgenic Research, 9: 279-299, 2000.
Giddings et al. "Transgenic Plants as Factories for Biopharmaceuticals", Nature Biotechnology, 18(11): 1151-1155, Nov. 2000.
Gomord et al. "Posttranslational Modification of Therapeutic Proteins in Plants", Current Opinion in Plant Biology, 7: 171-181, 2004.
Hart et al. "Crystal Structure of an Endochitinase From *Hordeum vulgare* L. Seeds", Journal of Molecular Biology, 229: 189-193, 1993.
Haseloff et al. "Removal of a Cryptic Intron and Subcellular Localization of Green Fluorescent Protein Are Required to Mark Transgenic *Arabidopsis* Plants Brightly", Proc. Natl. Acad. Sci. USA, 94: 2122-2127, Mar. 1997.
Hellens et al. "PGreen: A Versatile and Flexible Binary Ti Vector for Agrobacterium-Mediated Plant Transformation", Plant Molecular Biology, 42(6): 819-832, 2000.
James et al. "The Production of Foreign Proteins From Genetically Modified Plant Cells", Advances in Biochemical Engineering/Biotechnology, 72: 127-156, 2001.
Kallmes et al. "A Second-Generation, Endolumonal, Flow-Disrupting Device for Treatment of Saccular Aneurysms", Journal of Neuroradiology, 30: 1153-1158, 2009.
Ko et al. "Function and Glycosylation of Plant-Derived Antiviral Monoclonal Antibody", Proc. Natl. Acad. Sci. USA, 100(13): 8013-8018, 2003. p. 8013.
Laemmli "Relevant Page on Gel Electrophoresis", Nature, 227: 681, 1970.
Lanzino et al. "Efficacy and Current Limitations of Intravascular Stents for Intracranial Internal Carotid, Vertebral, and Basilar Artery Aneurysms", Journal of Neurosurgery, 91: 538-546, 1999.
Lee et al. "High-Density Algal Photobioreactors Using Light-Emitting Diodes", Biotechnology and Bioengineering, 44: 1161-1167, 1994.
Lerouge et al. "N-Glycoprotein Biosynthesis in Plants: Recent Developments and Future Trends", Plant Molecular Biology, 38: 31-48, 1998.
Lieber et al. "Alteration of Hemodynamics in Aneurysm Models by Stenting: Influence of Stent Porosity", Annals of Biomedical Engineering, 25(3): 460-469, 1997. Abstract.
Ma et al. "Genetic Modification: The Production of Recombinant Pharmaceutical Proteins in Plants", Nature Reviews Genetics 4: 794-805, 2003. Abstract.
Marinkovic et al. "Anatomic and Clinical Correlations of the Lenticulostriate Arteries", Clinical Anatomy, 14: 190-195, 2001.
Martin et al. "Glycosylation and Processing of High Levels of Active Human Glucoceerebrosidase in Invertebrate Cells Using a Baculovirus Expression Vector", DNA, 7(2): 99-106, 1988.
Petty "Ischemic Stroke Subtypes, A Populatation-Based Study of Incidence and Risk Factors", Stroke, p. 1513-1516, 1999.
Rayon et al. "The Protein N-Glycosylation in Plants", Journal of Experimental Botany, 49(326): 1463-1472, Sep. 1998.
Seffernick et al. "Melamine Deaminase and Atrazine Chlorohydrolase: 98 Percent Identical But Functionally Different", Journal of Bacteriology, 183(8): 2405-2410, Apr. 2001.
Sharp et al. "Characterization of Monoclonal Antibody Fragments Produced by Plant Cells", Biotechnology and Bioengineering, 73(5): 338-346, 2001. p. 345, col. 2, § 2.
Sorge et al. Alignments, Sequence List, 10/554387 SEQ ID No. 8.
Stroke Editorial Office "Major Ongoing Stroke Trials", p. 557-562, 2003.
Syrkin Wurtele et al. "A Simple, Efficient Method for the Agrobacterium-Mediated Transformation of Carrot Callus Cells", Plant Science, 61(2): 253-262, 1989.
Van Patten et al. "Effect of Mannose Chain length on Targeting of Glucocerebrosidase for Enzyme Replacement Therapy of Gaucher Disease", Glycobiology, 17(5): 467-478, 2007.
Van Weely et al. "Function of Oligosaccharide Modifications in Glucocerebrebrosidase, A Membrane-Associated Lysosomal Hydrolase", European Journal of Biochemistry, 191(3): 669-677, 1990.
Wakhloo et al. "Stents for Intracranial Aneurysms: The Beginning of a New Endovascular Era?", Neurosurgery, 43(2): 377-379, 1998.
Yu et al. "A Steady Flow Analysis on the Stented and Non-Stented Sidewall Aneurysm Models", Medical Engineering & Physics, 21(3): 133-141, 1999. Abstract.
Zhu et al. "Novel Polynucleic Acid Segment Useful for Modulating Gene Expression Within a Cell by Posttranscriptional Gene Silencing, and for Augmenting a Plant Cell Genome", Database GenBank, US National Library of Medicine, No. ABP81239, 2003.
European Search Report and the European Search Opinion dated Apr. 8, 2011 From the European Patent Office Re. Application No. 10012372.8.
European Search Report and the European Search Opinion dated Apr. 8, 2011 From the European Patent Office Re. Application No. 10012376.9.
Interview Summary dated Apr. 7, 2011 From the U.S. Patent and Trademark Office Re.: U.S. Appl. No. 12/385,894.
Notice of Allowance dated May 1, 2012 From the U.S. Patent and Trademark Office Re. U.S. Appl. No. 13/080,692.
Response dated Apr. 13, 2011 to Notice of Reason for Rejection dated Jan. 4, 2011 From the Japanese Patent Office Re.: Application No. 2006-507577.
International Search Report and the Written Opinion dated Apr. 9, 2010 From the International Searching Authority Re.: Application No. PCT/IL08/00576.
Communication Pursuant to Article 94(3) EPC dated May 10, 2012 From the European Patent Office Re. Application No. 10012374.4.
Translation of Notice of Reason for Rejection dated May 8, 2012 From the Japanese Patent Office Re. Application No. 2010-507055.

(56) References Cited

OTHER PUBLICATIONS

Translation of Notice of the Reason for Rejection dated Apr. 26, 2012 From the Korean Intellectual Property Office (KIPO) Re. Application No. 2006-7019631.
Sorge et al. "Glucocerebrosidase Precursor (5' End Put.); Putative [*Homo Sapiens*]", Database NCBI, GenBank Accession No. AAA35873, Apr. 27, 1993.
Invitation Pursuant to Article 94(3) and Rule 71(1) EPC dated Jun. 17, 2011 From the European Patent Office Re.: Application No. 04713966.2.
Examination Report dated Sep. 12, 2011 From the Instituto Mexicano de la Propriedad Industrial Re. Application No. PA/a/2005/011507.
Official Action dated Oct. 18, 2011 From ROSPATENT, Federal Government Institution, Federal Institute of Industrial Property of the Federal Service for Intellectual Property, Patents and Trademarks of the Russian Federation Re. Application No. 2009140906 and Its Summary in English.
Response dated Nov. 28, 2011 to Office Action dated Jun. 9, 2011 From the U.S. Patent and Trademark Office Re. U.S. Appl. No. 13/008,048.
Response dated Nov. 28, 2011 to Office Action dated Jun. 28, 2011 From the Israeli Patent Office Re.: Application No. 182888.
Response dated Dec. 5, 2011 to European Search Report and the European Search Opinion dated Apr. 5, 2011 From the European Patent Office Re. Application No. 10012374.4.
Response dated Dec. 6, 2011 to European Search Report and the European Search Opinion dated Apr. 1, 2011 From the European Patent Office Re. Application No. 10012375.1.
Response dated Nov. 20, 2011 to European Search Report and the European Search Opinion dated Apr. 8, 2011 From the European Patent Office Re. Application No. 10012376.9.
Restriction Official Action dated Nov. 29, 2011 From the U.S. Patent and Trademark Office Re. U.S. Appl. No. 13/080,694.
Response dated Jun. 2, 2011 to Official Action dated Feb. 2, 2011 From the U.S. Patent and Trademark Office Re.: U.S. Appl. No. 12/385,894.
Response dated Apr. 28, 2011 to Official Action dated Oct. 29, 2010 From the U.S. Patent and Trademark Office Re.: U.S. Appl. No. 10/554,387.
Aviezer et al. "A Plant-Derived Recombinant Human Glucocerebrosidase Enzyme—A Preclinical and Phase I Investigation", PLoS One, 4(3): 1-6, Mar. 2009.
Borrell "Virus Hits Genzyme Plant, Halting Production of Orphan Drugs", SciAmericanblog 2009.
Gaucher "Cerezyme", Gaucher's Association UK Website, http://www.gaucher.org.uk/newsstory.php?action=show&id=73, Apr. 22, 2010.
Press Release 2 "Protalix BioTherapeutics Announces Preliminary Top-Line Positive Data From Taliglucerase Alfa Switch over Trial ", Protalix Riotherapeutics, Nov. 2, 2010.
Press Release 3 "Protalix BioTherapeutics Announces French ATU Granted for Taliglicerase Alfa for the Treatment of Gaucher Disease", Protalix Biotherapeutics, Jul. 13, 2010.
Ratner "Pfizer Stakes a Claim in Plant Cell-Made Biopharmaceuticals", Nature Biotechnology, 28(2): 107-108, Feb. 2010. Press Release 1.
Official Action dated Feb. 2, 2011 From the U.S. Patent and Trademark Office Re.: U.S. Appl. No. 12/385,894.
Examination Report dated Sep. 13, 2011 From the Intellectual Property Office of Singapore, Issued by the Hungarian Patent Office dated Aug. 25, 2011 Re. Application No. 200907212-5.
European Search Report and the European Search Opinion dated Apr. 1, 2011 From the European Patent Office Re. Application No. 10012375.1.
European Search Report and the European Search Opinion dated Apr. 5, 2011 From the European Patent Office Re. Application No. 10012374.4.
Atkinson "Protein Trafficking in the Secretary and Endocytic Pathways", G817 Eukaryotic Cell Biology 2006, Internet Article, XP007917298, Retrieved From the Internet, p. 1-10, 2006.

Fu et al. "Retention of Subunits of the Oligosaccharyltransferase Complex in the Endoplasmic Reticulum", The Journal of Biological Chemistry, XP002624334, 275(6): 3984-3990, Feb. 11, 2000.
Karg et al. "The Production of Biopharmaceuticals in Plant Systems", Biotechnology Advances, XP002624335, 27(6): 879-894, Nov. 2009.
Official Action dated Apr. 6, 2010 From the U.S. Patent and Trademark Office Re.: U.S. Appl. No. 11/979,813.
Response dated Feb. 14, 2010 to Office Action dated Nov. 6, 2009 From the State Intellectual Property Office of the People's Republic of China Re.: Application No. 200480017916.2.
Response dated Apr. 22, 2010 to Examination Report dated Sep. 22, 2009 From the Instituto Mexicano de la Propriedad Industrial Re.: Application No. PA/a/2006/009612.
Summary of Official Action dated Mar. 29, 2010 From Rospatent, Federal State Office , Federal Institution of Industrial Property of the Federal Office of Intellectual Property, Patents and Trademarks of the Russian Federation Re.: Application No. 2009140906.
Examination Report dated Apr. 7, 2011 From the Instituto Mexicano de la Propriedad Industrial Re. Application No. PA/a/2005/011507.
Response dated Mar. 31, 2011 to Search Report and Written Opinion dated Nov. 8, 2010 From the Intellectual Property Office of Singapore Issued by the Austrian Patent Office Re. Application No. 200717273-7.
Neuhaus et al. "Mutation Analysis of the C-Terminal Vacuolar Targeting Peptide of Tobacco Chitinase: Low Specificity of the Sorting System, and Gradual Transition Between Intracellular Retention and Secretion Into the Extracellular Space", the Plant Journal, 5(1): 45-54, 1994.
Office Action dated Jun. 28, 2011 From the Israeli Patent Office Re.: Application No. 182888 and Its Translation Into English.
Examination Report dated Aug. 2, 2011 From the Government of India, Patent Office, Intellectual Property Building Re.: Application No. 3478/CHENP/2006.
Written Opinion dated Jul. 26, 2011 From the Intellectual Property Office of Singapore, Issued by the Hungarian Patent Office dated Apr. 6, 2011 Re. Application No. 2009073719.
Office Action dated Jul. 25, 2010 From the Israeli Patent Office Re.: Application No. 171561 and Its Translation Into English.
Response dated Aug. 25, 2010 to Summons to Attend Oral Proceedings Pursuant to Rule 115(1) EPC of Jul. 23, 2010 From the European Patent Office Re.: Application No. 04713966.2.
Chrispeels et al. "The Production of Recombinant Glycoproteins With Defined Non-Immunogenic Glycans", Transgenic Plant: A Production System for Industrial and Pharmaceutical Proteins, Chap.2: 99-102, 1996.
Cramer et al. "Bioproduction of Human Enzymes in Transgenic Tobacco", Annals of the New York Academy of Sciences, 792: 62-71, May 25, 1996.
Official Action dated Aug. 10, 2011 From the U.S. Patent and Trademark Office Re. U.S. Appl. No. 10/554,387.
Translation of Notice of the Reason for Rejection dated Aug. 24, 2011 From the Korean Intellectual Property Office (KIPO) Re. Application No. 2006-7019631.
Response dated Nov. 10, 2011 to Notice of Reason for Rejection dated Sep. 16, 2011 From the Japanese Patent Office Re. Application No. 2007-500352.
Restriction Official Action dated Oct. 28, 2011 From the U.S. Patent and Trademark Office Re. U.S. Appl. No. 13/080,692.
Office Action dated Oct. 27, 2011 From the Israel Patent Office Re. Application No. 201799 and Its Translation Into English.
Response dated Nov. 16, 2011 to European Search Report and the European Search Opinion dated Apr. 8, 2011 From the European Patent Office Re. Application No. 10012372.8.
Response dated Nov. 24, 2011 to Notice of the Reason for Rejection dated Aug. 24, 2011 From the Korean Intellectual Property Office (KIPO) Re. Application No. 2006-7019631.
Response dated Nov. 28, 2011 to Requisition by the Examiner dated May 31, 2011 From the Canadian Intellectual Property Office Re. Application No. 2,557,525.
Vitale et al. "The Endoplasmic Reticulum—Gateway of the Secretory Pathway", The Plant Cell, 11: 615-628, Apr. 1999.

(56) References Cited

OTHER PUBLICATIONS

Office Action dated Nov. 27, 2012 From the Israel Patent Office Re. Application No. 201929 and Its Translation Into English.
Communication Pursuant to Article 94(3) EPC dated Sep. 12, 2012 From the European Patent Office Re. Application No. 10012373.6.
Communication Pursuant to Article 94(3) EPC dated Aug. 14, 2012 From the European Patent Office Re. Application No. 10012375.1.
Communication Pursuant to Article 94(3) EPC dated Aug. 28, 2012 From the European Patent Office Re. Application No. 10012372.8.
Office Action dated Aug. 28, 2012 From the U.S. Patent and Trademark Office Re. U.S. Appl. No. 13/008,048.
Official Action dated Jul. 16, 2012 From the U.S. Patent and Trademark Office Re. U.S. Appl. No. 12/451,188.
Official Action dated Jul. 20, 2012 From the U.S. Patent and Trademark Office Re. U.S. Appl. No. 13/080,694.
Translation of Notice of Reason for Rejection dated Jun. 28, 2012 From the Korean Intellectual Property Office Re. Application No. 2011-7014421.
Translation of Notice of the Reason for Rejection dated Jun. 28, 2012 From the Korean Intellectual Property Office Re. Application No. 10-2005-7020434.
Atkinson "RecName: Full=Polygalacturonase; Short=PG; EC=3.2.1.15; AltName: Full=Pectinase; Flags: Precursor", UniProtKB/Swiss-Prot., Medline=95062722, PGLR_MALDO, Accession No. P48978, Feb. 1, 1996.
Boller et al. Alignment to Patent U.S. Pat. No. 6,054,637, filed Apr. 25, 2000.
Germain "Fabry Disease: Recent Advances in Enzyme Replacement Therapy", Expert Opinion on Investigational Drugs, 11(10): 1467-1476, Oct. 2002.
Podsakoff et al. "Human Glucocerebrosidase (GC) #2", WPI SCORE Search Results, Accession No. AAE02446, Aug. 10, 2001.
Tsuji et al. "RecName: Full=Alpha-Galactosidase A; EC=3. 2.1.22; AltName: Full=Alpha-D-Galactosidase A; AltName: Full=Alpha-D-Galactoside Galactohydrolase; AltName: Full=Melibiase; AltName: INN=Agalsidase; Flags: Precursor", UniProtKB/Swiss-Prot., Medline=87246603, AGAL_HUMAN, Accession No. P06280, Jan. 1, 1988.
Examination Report dated Feb. 8, 2013 From the Government of India, Patent Office, Intellectual Property Building Re. Application No. 930/CHENP/2008.
Requisition by the Examiner dated Jan. 24, 2013 From the Canadian Intellectual Property Office Re. Application No. 2,523,539.
Summons to Attend Oral Proceedings Pursuant to Rule 115(1) EPC dated Feb. 14, 2013 From the European Patent Office Re. Application No. 10012376.9.
Official Action dated Jan. 29, 2013 From the U.S. Patent and Trademark Office Re.: U.S. Appl. No. 12/451,188.
Restriction Official Action dated Jan. 31, 2013 From the U.S. Patent and Trademark Office Re. U.S. Appl. No. 13/555,243.
Translation of Notice of Reason for Rejection dated Jan. 18, 2013 From the Japanese Patent Office Re. Application No. 2010-505007.
Requisition by the Examiner dated Oct. 11, 2012 From the Canadian Intellectual Property Office Re. Application No. 2,557,525.
Translation of Office Action dated Sep. 29, 2012 From the State Intellectual Property Office of the People's Republic of China Re. Application No. 200880023217.7.
Written Opinion dated Oct. 23, 2012 From the Intellectual Property Office of Singapore Issued by the Austrian Patent Office Re. Application No. 200717273-7.
Notice of Allowance dated Nov. 13, 2012 From the U.S. Patent and Trademark Office Re. U.S. Appl. No. 13/080,694.
Translation of Notice of Reason for Rejection dated Nov. 13, 2012 From the Japanese Patent Office Re. Application No. 2011-99013.
Braun et al. "Metabolic Correction and Cross-Correction of Mucopolysaccharidosis Type II (Hunter Syndrome) by Retroviral-Mediated Gene Transfer and Expression of Human Iduronate-2-Sulfatase", Proc. Natl. Acad. Sci. USA, 90: 11830-11834, Dec. 1993.
Applicant-Tritiated Interview Summary dated Nov. 2, 2012 From the U.S. Patent and Trademark Office Re. U.S. Appl. No. 13/080,694.
Translation of Office Action dated Aug. 28, 2012 From the State Intellectual Property Office of the People's Republic of China Re. Application No. 200880023649.8.
Translation of Search Report dated Aug. 28, 2012 From the State Intellectual Property Office of the People's Republic of China Re. Application No. 200880023649.8.
Office Action dated Dec. 3, 2012 From the Israeli Patent Office Re.: Application No. 182888 and Its Translation Into English.
Translation of Official Decision of Rejection dated Apr. 16, 2013 From the Japanese Patent Office Re. Application No. 2010-507055.
Office Action dated Jun. 27, 2013 From the Israel Patent Office Re. Application No. 201929 and Its Translation Into English.
Communication Pursuant to Article 94(3) EPC dated Nov. 14, 2013 From the European Patent Office Re. Application No. 10012372.8.
Communication Pursuant to Article 94(3) EPC dated Oct. 30, 2013 From the European Patent Office Re. Application No. 10012373.6.
Ex Parte Quayle Official Action dated Oct. 9, 2013 From the U.S. Patent and Trademark Office Re. U.S. Appl. No. 13/555,243.
Invitation Pursuant to Article 94(3) and Rule 71(1) EPC dated Nov. 13, 2013 From the European Patent Office Re. Application No. 10012375.1.
Patent Examination Report dated Sep. 11, 2013 From the Australian Government, IP Australia Re. Application No. 2008246928.
Requisition by the Examiner dated Oct. 18, 2013 From the Canadian Intellectual Property Office Re. Application No. 2,557,525.
Notice of Acceptance dated Apr. 3, 2014 From the Australian Government, IP Australia Re. Application No. 2008246928.
Office Action dated Feb. 18, 2014 From the State Intellectual Property Office of the People's Republic of China Re. Application No. 200880023649.8 and Its Translation into English.
Order u/s 15 of the Patents Act, 1970 for Patent Application No. 930/CHENP/2008 dated Mar. 14, 2014 From the Government of India, Patent Office, Intellectual Property Building Re. Application No. 930/CHENP/2008.
Request for Examination dated Mar. 25, 2014 From the Rospatent, Federal State Office, Federal Institution of Industrial Property of the Federal Office of Intellectual Property, Patents and Trademarks of the Russian Federation Re. Application No. 2009148012 and Its Translation Into English.
Restriction Official Action dated Mar. 24, 2014 From the U.S. Patent and Trademark Office Re. U.S. Appl. No. 13/727,632.
Search Report and Written Opinion dated Feb. 28, 2014 From the Intellectual Property Office of Singapore Issued by the Austrian Patent Office Re. Application No. 2013-02121-7.
Communication Pursuant to Article 94(3) EPC dated Jul. 14, 2014 From the European Patent Office Re. Application No. 10012374.4.
Official Action dated Jul. 30, 2014 From the U.S. Patent and Trademark Office Re. U.S. Appl. No. 13/727,632.
Replacing Examination Report dated Aug. 22, 2014 From the Intellectual Property Office of Singapore issued by the Austrian Patent Office Re. Application No. 200717273-7.
Requisition by the Examiner dated Sep. 4, 2014 From the Canadian Intellectual Property Office Re. Application No. 2,685,701.
Search Report and Written Opinion dated Jun. 30, 2014 From the Intellectual Property Office of Singapore Issued by the Hungarian Intellectual Property Office Re. Application No. 201300195-3.
Written Opinion dated Feb. 6, 2015 From the Intellectual Property Office of Singapore Issued by the Austrian Patent Office Re. Application No. 201302121-7.
Official Decision of Rejection dated Jul. 7, 2015 From the Japanese Patent Office Re. Application No. 2013-168642 and Its Translation Into English.
Notice of the Reason for Rejection dated Dec. 26, 2014 From the Korean Intellectual Property Office Re. Application No. 10-2009-7024937 and Its Translation Into English.
Notice of Reason for Rejection dated Nov. 21, 2014 From the Japanese Patent Office Re. Application No. 2013-168642 and Its Translation Into English.
Office Action dated Oct. 21, 2014 From the State Intellectual Property Office of the People's Republic of China Re. Application No. 200880023649.8 and Its Translation Into English.

(56) References Cited

OTHER PUBLICATIONS

Examination Report dated Jan. 5, 2015 From the Intellectual Property Office of Singapore Issued by the Hungarian Intellectual Property Office Re. Application No. 201300195-3.
Restriction Official Action dated Jan. 9, 2015 From the U.S. Patent and Trademark Office Re. U.S. Appl. No. 14/292,966.
Office Action dated Oct. 6, 2015 From the Israel Patent Office Re. Application No. 229100 and Its Translation Into English.
Patent Examination Report dated Oct. 20, 2015 From the Australian Government, IP Australia Re. Application No. 2014203790.
Requisition by the Examiner dated Sep. 14, 2015 From the Canadian Intellectual Property Office Re. Application No. 2,685,701.
Communication Pursuant to Article 94(3) EPC dated Mar. 4, 2016 From the European Patent Office Re. Application No. 05718834.4.
Merck "CVGB75S01 / Durapore Cartridge Filter 5 in. 0.22 μm Hydrophilic Code 7", Merck Millpore, Product Description, 3 P., 2016.
Merck "GVHP04700 / Durapore Membrane Filter, PVDF, Hydrophobic, 0.22 μm, 47 mm, White, Plain", Merck Millpore, Product Description, 2 P., 2016.
Merck "GVHP29325 / Durapore® Membrane, PVDF, Hydrophobic, 0.22 μm, 293 mm, White, Plain", Merck Millpore, Product Description, 2 P., 2016.
Merck "HVHP29325 / Durapore Membrane, PVDF, Hydrophobic, 0.45 μm, 293 mm, White, Plain", Merck Millpore, Product Description, 2 P., 2016.
Merck "Sterilizing-Grade Aervent Cartridge Filters", Merck Millpore, Product Description, 2 P., 2016.
Merck "Sterilizing-Grade Durapore 0.1 μm and 0.22 μm Hydrophilic Cartridge Filters", Merck Millpore, Product Description, 7 P., 2016.
Translation of Notice of Reason for Rejection dated Aug. 31, 2010 From the Japanese Patent Office Re. Application No. 2007-500352.

\* cited by examiner

1. PX-400-GC 2 10µg
2. PLX-016-0505 DS 10µg
3. PLX-016-0505 DS 20µg
4. Cerezyme 10µg
5. Cerezyme 20µg
6. MW markers 1. PX-400-GC 2 50ng
2. PX-400-GC-2 100ng
3. PLX-016-0505 DS 50ng
4. PLX-016-0505 DS 100ng
5. Cerezyme 50ng
6. Cerezyme 100ng 1. PI standard
2. PX-400-GC-2 C-3
3. PX-400-GC-2 C-4
4. PX-400-GC-2 C-5
5. PLX-GC-016-0505DS
6. PI standard 1. PX-400-GC-2 50ng
2. PX-400-GC-2 100ng
3. PLX-016-0505 DS 50ng
4. PLX-016-0505 DS 100ng
5. Cerezyme 50ng
6. Cerezyme 100ng
7. CHP 50ng
8. CHP 100ng

SEQUENCE LISTING

<160> NUMBER OF SEQ ID NOS: 11

<210> SEQ ID NO 1
<211> LENGTH: 18
<212> TYPE: DNA
<213> ORGANISM: Artificial sequence
<220> FEATURE:
<223> OTHER INFORMATION: Single strand DNA nucleotide

<400> SEQUENCE: 1
ctcagaagac cagagggc                                                     18

<210> SEQ ID NO 2
<211> LENGTH: 17
<212> TYPE: DNA
<213> ORGANISM: Artificial sequence
<220> FEATURE:
<223> OTHER INFORMATION: Single strand DNA nucleotide

<400> SEQUENCE: 2
caaagcggcc atcgtgc                                                      17

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
cagaattcgc ccgcccctgc a                                                 21

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
ctcagatctt ggcgatgcca ca                                                22

<210> SEQ ID NO 5
<211> LENGTH: 21
<212> TYPE: DNA
<213> ORGANISM: Artificial sequence
<220> FEATURE:
<223> OTHER INFORMATION: Nucleic acid sequence encoding the vacuolar
      targeting signal peptide derived fromTobacco chitinase A

<400> SEQUENCE: 5
gatcttttag tcgatactat g                                                 21

<210> SEQ ID NO 6
<211> LENGTH: 66
<212> TYPE: DNA
<213> ORGANISM: Artificial sequence
<220> FEATURE:
<223> OTHER INFORMATION: Nucleic acid sequence encoding the ER signal
      peptide derived from the Arabidopsis basic endochitinase gene

<400> SEQUENCE: 6
atgaagacta atctttttct ctttctcatc ttttcacttc tcctatcatt atcctcggcc       60
gaattc                                                                  66

```
<210> SEQ ID NO 7
<211> LENGTH: 33
<212> TYPE: PRT
<213> ORGANISM: Artificial sequence
<220> FEATURE:
<223> OTHER INFORMATION: Acetylcholinesterase leader sequence into the
      ER

<400> SEQUENCE: 7

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly

<210> SEQ ID NO 8
<211> LENGTH: 6
<212> TYPE: PRT
<213> ORGANISM: Artificial sequence
<220> FEATURE:
<223> OTHER INFORMATION: ER retention signal

<400> SEQUENCE: 8

Ser Glu Lys Asp Glu Leu
1               5

<210> SEQ ID NO 9
<211> LENGTH: 606
<212> TYPE: PRT
<213> ORGANISM: Artificial sequence
<220> FEATURE:
<223> OTHER INFORMATION: A recobinant protein consists of the native
      leader sequence into the ER fused to the acetylcholinesterase
      "read through" variant (AChE-R) and the ER retention sequence

<400> SEQUENCE: 9

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190
```

-continued

```
Pro Gly Ser Arg Glu Ala Pro Gly Asn Val Gly Leu Leu Asp Gln Arg
        195                 200                 205

Leu Ala Leu Gln Trp Val Gln Glu Asn Val Ala Ala Phe Gly Gly Asp
    210                 215                 220

Pro Thr Ser Val Thr Leu Phe Gly Glu Ser Ala Gly Ala Ala Ser Val
225                 230                 235                 240

Gly Met His Leu Leu Ser Pro Ser Arg Gly Leu Phe His Arg Ala
                245                 250                 255

Val Leu Gln Ser Gly Ala Pro Asn Gly Pro Trp Ala Thr Val Gly Met
                260                 265                 270

Gly Glu Ala Arg Arg Arg Ala Thr Gln Leu Ala His Leu Val Gly Cys
            275                 280                 285

Pro Pro Gly Gly Thr Gly Gly Asn Asp Thr Glu Leu Val Ala Cys Leu
    290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Asp Gly
                325                 330                 335

Asp Phe Leu Ser Asp Thr Pro Glu Ala Leu Ile Asn Ala Gly Asp Phe
                340                 345                 350

His Gly Leu Gln Val Leu Val Gly Val Val Lys Asp Glu Gly Ser Tyr
            355                 360                 365

Phe Leu Val Tyr Gly Ala Pro Gly Phe Ser Lys Asp Asn Glu Ser Leu
    370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
                420                 425                 430

Val Gly Asp His Asn Val Val Cys Pro Val Ala Gln Leu Ala Gly Arg
            435                 440                 445

Leu Ala Ala Gln Gly Ala Arg Val Tyr Ala Tyr Val Phe Glu His Arg
    450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
    515                 520                 525

Pro Gln Trp Pro Pro Tyr Thr Ala Gly Ala Gln Gln Tyr Val Ser Leu
530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Gly Met
                565                 570                 575

Gln Gly Pro Ala Gly Ser Gly Trp Glu Glu Gly Ser Gly Ser Pro Pro
            580                 585                 590

Gly Val Thr Pro Leu Phe Ser Pro Ser Glu Lys Asp Glu Leu
    595                 600                 605
```

```
<210> SEQ ID NO 10
<211> LENGTH: 28
<212> TYPE: DNA
<213> ORGANISM: Artificial sequence
<220> FEATURE:
<223> OTHER INFORMATION: Single strand DNA nucleotide

<400> SEQUENCE: 10
cggcgtcgac acaagaggcc tccacaat                                           28

<210> SEQ ID NO 11
<211> LENGTH: 28
<212> TYPE: DNA
<213> ORGANISM: Artificial sequence
<220> FEATURE:
<223> OTHER INFORMATION: Single strand DNA nucleotide

<400> SEQUENCE: 11
ccccctgcag ctagagttca tccttctc                                           28
```

LARGE SCALE DISPOSABLE BIOREACTOR

RELATED APPLICATIONS

This Application is a National Phase of PCT Patent Application No. PCT/IL2008/000614 having International filing date of May 5, 2008, which claims the benefit of U.S. Provisional Patent Application No. 60/924,273 filed on May 7, 2007. The contents of the above Applications are all incorporated herein by reference.

FIELD OF THE INVENTION

The invention is of a large scale disposable bioreactor for cell/tissue culture, and in particular, of a large scale bioreactor for plant cell culture.

BACKGROUND OF THE INVENTION

Cell and tissue cultures are routinely utilized for commercial-scale production of various compounds including, for example, hormones, enzymes, proteins, antigens, food additives and natural pesticides.

Technology presently utilized for the production of cell and/or tissue culture at industrial scale is based on reusable glass or stainless steel bioreactor systems which are costly to set-up and maintain. Such bioreactor systems require cleaning and disinfecting between batches, and more intensive cleaning between product changeovers due to the need for expensive and time-consuming validation for cleanliness and presence of cleaning agent residue following cleaning.

In addition, these types of industrial bioreactor systems employ complicated and expensive mixing technologies such as impellers powered through expensive and complicated sterile seals; some expensive bioreactors comprise an airlift multipart construction, designed to provide mixing and gas saturation of the medium through bubbling of gas into the bioreactor. However, gas pressure, bubble size and the creation of undesirable shear forces in the medium necessitates the implementation of complicated aeration technologies. In addition, such bioreactors are designed according to the peak volume capacity that is required at the time. Thus, problems arise when scaling up from pilot plant bioreactor to large-scale bioreactor, or when the need arises to increase production beyond the capacity of existing bioreactors. The current alternative to operating a large-capacity bioreactor is to combine a number of smaller modular glass or stainless steel bioreactors whose total volume capacity matches requirements, while offering a degree of flexibility for increasing or reducing overall capacity. However, use of several smaller bioreactors increases cost and maintenance time and thus use of several small bioreactors is more expensive and labor intensive than the use of a single larger bioreactor.

Due to these limitations, culturing of plant cells in prior art bioreactors results in relatively expensive extractable products, including both secondary metabolites and recombinant proteins, which cannot compete commercially with comparable products produced by alternative production systems.

Presently, the only culture-based recombinant protein pharmaceutical produced in plant cell bioreactors is a commercial anti-viral vaccine for veterinary use in treatment of Newcastle virus. Other than this vaccine, however, there are presently only a very few secondary metabolite products produced by cell-culture in bioreactors, such as the plant metabolites paclitaxel (Taxol) and Shikonin.

At commercial scale, bioreactor systems traditionally employ permanent or semi-permanent growth chambers. Although disposable growth chambers are well known in the art, such growth chambers are typically utilized for small scale production volumes, such as in home brewing and for experimental laboratory work. Small scale bioreactors typically employ a disposable bag which can be utilized in laboratory settings.

Disposable bioreactors suitable for use with larger volumes have also been proposed. The requirements of agitation and aeration of the culture medium, which become more critical with scale-up of the reactor volume, are addressed in a number of ways in prior art systems. Applikon Biotechnology (The Netherlands) and Stedim Inc. (France) offer the Appliflex® single use bioreactor system using 50 liter flexible culture bags, which are designed for placement on a motorized platform which rocks the bag to provide aeration and agitation of the culture medium. A similar disposable bioreactor device is offered by Wave Biotech, LLD (Somerset, N.J.), which provides culture bags for volumes up to 1000 L, which are also aerated and agitated by a motorized platform. Hyclone Inc. (Logan, Utah), in conjunction with Baxter Biosciences, offers a disposable culture bag (Single Use Bioreactor "SUB") designed for animal cell culture of up to 250 L, which is designed to retrofit stainless steel bioreactor vessels. Aeration and agitation is provided by a non-disposable impeller drive, which attaches to a complicated impeller unit integrated into the culture bag. US Patent Application No. 2005/0272146 to Hodge et al. discloses a 150 liter disposable bioreactor having impellor blades or other mechanical means for mixing. Yet another type of disposable bioreactor has a U-shaped bag, and requires a crane-like apparatus to agitate and aerate the culture medium through reciprocal lifting of the sides. Still another solution is based on a pressurized cuff surrounding the flexible culture bag, which is made to inflate and deflate at regular intervals, providing a squeezing type of mixing motion.

In all the abovementioned systems, support and aeration/agitation systems are complicated, costly, dedicated and limited in capacity. Thus, although the reactor vessel itself may be disposable and intended for single use, use of these systems requires costly tool-up and maintenance.

Disposable bioreactor devices using air for agitation and aeration of the culture have also been proposed, however, adaptation of air-bubble based aeration and mixing for large volumes is problematic. Many smaller volume bioreactors provide sufficient aeration with a single gas inlet and sparger, or other type of diffuser for the gas bubbles [see, for example, the Zeta bioreactor offered by Osmotec, Israel, (Agritech Israel, issue No. 1, Fall 1997, page 19)]. One disadvantage of such systems is that aeration performed by introducing very small air bubbles (from the diffuser) results in damage to cells, particularly in the case of plant cell cultures which are particularly sensitive to shear forces.

Proteins for pharmaceutical use have been traditionally produced in mammalian or bacterial expression systems. However, due to the relative simplicity of introducing genes into plants and plant cells for mass production of proteins and peptides, using, for example, plant molecular biology systems such as the *Agrobacterium* method, plant cell technology is becoming increasingly popular as an alternative protein expression system (Ma, J. K. C., Drake, P. M. W., and Christou, P. (2003) *Nature reviews* 4, 794-805).

Plant cell culture differs from bacterial or mammalian cell culture, not only in terms of metabolic requirements, but also as a function of the extreme fragility of the generally large sized plant cells to shear forces found in conventional industrial bioreactor. Thus, on the one hand, it is important to provide adequate mixing in the plant cell cultures, to ensure sufficient aeration of all aspects of the plant cell culture, but, on the other hand, this must be done in a manner suitable for the fragile plant cells grown in culture.

Thus, there is a constant need for improving on existing systems and devices for disposable cell/tissue culture, in order to provide greater yield and quality of the product, as well as improved cost-effectiveness. The present invention provides a high volume, disposable but reusable bioreactor, effective for use with a variety of cells/cell cultures for production of recombinant protein, in which the problems inherent in scale-up of the disposable reactor volume have been addressed.

SUMMARY OF THE INVENTION

According to one aspect of the present invention there is provided a disposable device for culturing and harvesting plant tissue and/or cells comprising a non-rigid container having a volume of at least 400 liters and being configured with gas exchange ports and a harvesting port enabling said device to be used continuously for at least two consecutive culturing/harvesting cycles, wherein the device is designed and constructed for maintaining oxygen saturation and shear forces suitable for culturing said plant tissue and/or cells.

According to another aspect of the present invention there is provided a method for culturing and harvesting a plant tissue and/or plant cells in a volume greater than 400 liters, the method comprising: (a) providing a disposable non-rigid container having a volume of at least 400 liters and being configured with gas exchange ports and a harvesting port enabling said device to be used continuously for at least two consecutive culturing/harvesting cycles, wherein the device is designed and constructed for maintaining oxygen saturation and shear forces suitable for culturing said plant tissue and/or cells; and (b) providing inoculant via said harvesting port; (c) providing sterile culture medium and/or sterile additives; (d) optionally illuminating said container with external light; and (e) allowing said cells and/or tissue to grow in said medium to a desired yield.

According to further features in preferred embodiments of the invention described below, said oxygen saturation and said shear forces suitable for culturing said plant tissue and/or cells are maintained by combination of values or value ranges of the following parameters:
 a) a height to volume ratio;
 b) an inlet gas pressure;
 c) a density of gas inlets per cross sectional area;
 d) an aeration rate at inlet; and
 e) a gas bubble volume at inlet.

According to another aspect of the present invention there is provided a plant cell culturing system comprising the disposable device for culturing and harvesting plant tissue and/or cells; and culture medium suitable for culturing said plant tissue and/or cells.

According to yet further features in preferred embodiments of the invention described below the system further comprises a plant cell suspension or tissue culture growing in said medium.

According to still further features in preferred embodiments of the invention described below the plant cell culture comprises plant cells obtained from a plant root.

According to further features in preferred embodiments of the invention described below plant cells are selected from the group consisting of *Agrobacterium rihzogenes* transformed root cell, celery cell, ginger cell, horseradish cell and carrot cell.

According to further features in some embodiments of the present invention, the plant cells are tobacco cells, more preferably *Nicotiana tabaccum* cells.

According to further features in some embodiments of the present invention, the tobacco cells express human recombinant acetylcholinesterase. The human recombinant acetylcholinesterase can be acetylcholinesterase-R. The acetylcholinesterase-R can have an amino acid sequence as set forth in SEQ ID NO: 9.

According to further features in some embodiments of the present invention the tobacco cells comprise a nucleic acid sequence encoding a polypeptide as set forth in SEQ ID NO: 9.

According to yet further features in preferred embodiments of the invention described below, the values or value range of parameters are selected from at least one of the following values or value ranges:
 a) a height to volume ratio of about 0.06 to about 1 centimeter per liter;
 b) an inlet gas pressure of about to 1 bar to 5 bar;
 c) a density of gas inlets per cross sectional area of about 20 inlets per square meter to about 70 inlets per square meter;
 d) an aeration rate at inlet of about 0.05 to 0.12 volumes gas per volume medium per minute; and
 e) a gas bubble volume at inlet of about 20 cubic millimeters to about 1800 cubic millimeters.

According to still further features in preferred embodiments of the invention described below, the oxygen saturation is at least 15% volume per volume in a liquid contained within said container.

According to further features in preferred embodiments of the invention described below the combination is of a height to volume ratio of about 0.06 to about 1 centimeter per liter and an inlet gas pressure of about to 1 bar to 5 bar.

According to yet further features in preferred embodiments of the invention described below the combination is of a height to volume ratio of about 0.06 to about 1 centimeters per liter and a density of gas inlets per cross sectional area of about 20 inlets per square meter to about 70 inlets per square meter.

According to still further features in preferred embodiments of the invention described below the combination is of a height to volume ratio of about 0.06 to about 1 centimeters per liter and an aeration rate at inlet of about 0.05 to 0.12 volumes gas per volume medium per minute.

According to further features in preferred embodiments of the invention described below the combination is of a height to volume ratio of about 0.06 to about 1 centimeter per liter and a gas bubble volume at inlet of about 20 cubic millimeters to about 1800 cubic millimeters.

According to yet further features in preferred embodiments of the invention described below the combination further comprises the parameter of a gas bubble volume at inlet of about 20 cubic millimeters to about 1800 cubic millimeters.

According to still further features in preferred embodiments of the invention described below the combination further comprises the parameter of and an inlet gas pressure of about to 1 bar to 5 bar.

According to further features in preferred embodiments of the invention described below the combination further comprises the parameter of a density of gas inlets per cross sectional area of about 20 inlets per square meter to about 70 inlets per square meter.

According to still further features in preferred embodiments of the invention described below the combination further comprises the parameter of an aeration rate at inlet of about 0.05 to 0.12 volumes gas per volume medium per minute.

According to yet further features in preferred embodiments of the invention described below the combination comprises a height to volume ratio of about 0.06 to about 1 centimeter per liter, an inlet gas pressure of about to 1 bar to 5 bar, a density of gas inlets per cross sectional area of about 20 inlets per square meter to about 70 inlets per square meter and a gas bubble volume at inlet of about 20 cubic milliliters to about 1800 cubic milliliters.

According to still further features in preferred embodiments of the invention described below the combination is of a height to volume ratio of about 0.06 to about 1 centimeter per liter, an inlet gas pressure of about to 1 bar to 5 bar, a density of gas inlets per cross sectional area of about 20 inlets per square meter to about 70 inlets per square meter, an aeration rate at inlet of about 0.05 to 0.12 volumes gas per volume medium per minute; and a gas bubble volume at inlet of about 20 cubic millimeters to about 1800 cubic millimeters.

According to further features in preferred embodiments of the invention described below the height to volume ratio is about 0.1 cm to about liter to 0.5 cm to liter.

According to yet further features in preferred embodiments of the invention described below the height to volume ratio is about 0.44 cm to liter.

According to still further features in preferred embodiments of the invention described below the inlet gas pressure is about 1.5 bar to about 4 bar.

According to further features in preferred embodiments of the invention described below the inlet gas pressure is about 1.5 bar to about 2.5 bar.

According to yet further features in preferred embodiments of the invention described below the density of gas inlets per cross-sectional area is about 40 per square meter to about 60 per square meter.

According to still further features in preferred embodiments of the invention described below the density of gas inlets per cross-sectional area is 55 per square meter.

According to yet further features in preferred embodiments of the invention described below the gas bubbling rate is about 20 liters per minute to about 50 liters per minute, more preferably 30 liters per minute.

According to still further features in preferred embodiments of the invention described below the gas bubble volume at the inlet is about 300 cubic millimeters.

According to further features in preferred embodiments of the invention described below the disposable container is transparent and/or translucent.

According to still further features in preferred embodiments of the invention described below the container is made from a material is selected from the group comprising polyethylene, polycarbonate, a copolymer of polyethylene and nylon, PVC and EVA.

According to yet further features in preferred embodiments of the invention described below the container is made from a laminate of more than one layer of said materials.

According to further features in preferred embodiments of the invention described below the device further comprises a support structure for supporting said device.

According to yet further features in preferred embodiments of the invention described below the support structure comprises a rigid cylindrical frame having a conical base.

According to still further features in preferred embodiments of the invention described below the harvesting port is located at the bottom of said bottom end of the container.

According to further features in preferred embodiments of the invention described below said harvesting port is located near the bottom of the bottom end of said container, such that at the end of each harvesting cycle said remainder of said medium containing cells and/or tissue automatically remains at said bottom end of said container up to a level below the level of said harvester.

According to still further features in preferred embodiments of the invention described below said bottom end is substantially conical.

According to yet further features in preferred embodiments of the invention described below the said bottom end is substantially frusta-conical.

According to further features in preferred embodiments of the invention described below said container comprises an internal fillable volume of between about 400 liters and about 30000 liters, preferably between about 500 liters and 8000 liters, and preferably about 1000 liters.

According to yet further features in preferred embodiments of the invention described below the method further comprising checking for contaminants and/or the quality of the cells/tissues which are produced in said container: if contaminants are found or the cells/tissues which are produced are of poor quality, the device and its contents are disposed of; if contaminants are not found, harvesting a portion of said medium containing cells and/or tissue.

According to further features in preferred embodiments of the invention described below, while harvesting said portion, leaving a remainder of medium containing cells and/or tissue in said container, wherein said remainder of medium serves as inoculant for a next culture/harvest cycle.

According to still further features in preferred embodiments of the invention described below the method further comprising: providing sterile culture medium and/or sterile additives for the next culture/harvest cycle; and repeating the growth cycle until said contaminants are found or the cells/tissues which are produced are of poor quality, whereupon the device and its contents are disposed of.

According to yet further features in preferred embodiments of the invention described below, wherein sterile air is supplied through said gas exchange ports continuously throughout at least one culture/harvest cycle.

According to further features in preferred embodiments of the invention described below the sterile air is supplied through said plurality of gas inlets in pulses during at least one culturing/harvest cycle.

According to further features in preferred embodiments of the invention described below the device has no mechanical means for mixing and aerating the culture medium.

The present invention successfully addresses the shortcomings of the presently known configurations by providing a high volume, disposable but reusable bioreactor, effective for use with a variety of cells/cell cultures for production of recombinant protein, and methods and systems for the use thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 illustrates the main components of an exemplary embodiment of the device of the present invention in cross-sectional side view;

FIG. 2 illustrates the main components of an exemplary embodiment of the device of the present invention and an exemplary support structure in front elevation;

Figure 3:
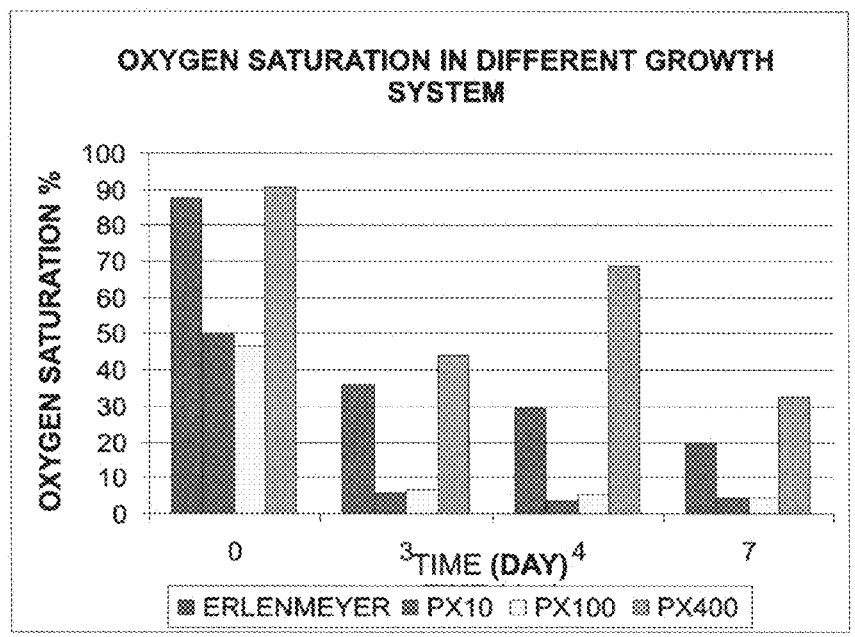
Figure 4:
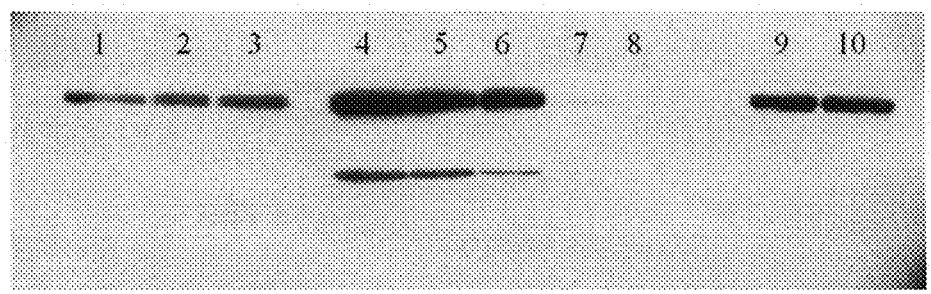
Figure 5A:
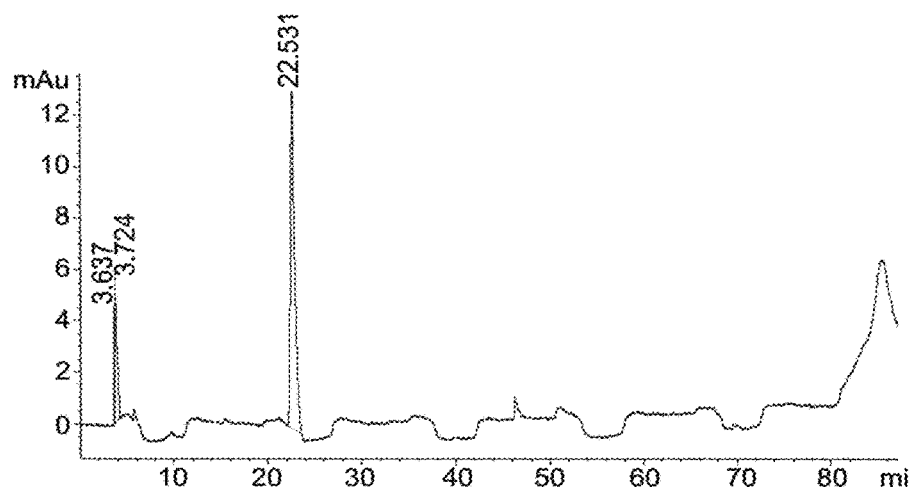
Figure 5B:
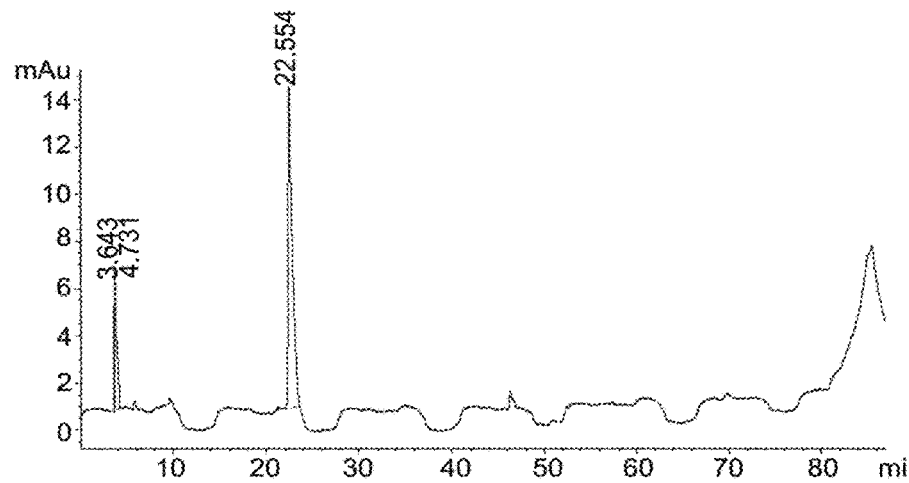
Figure 6:
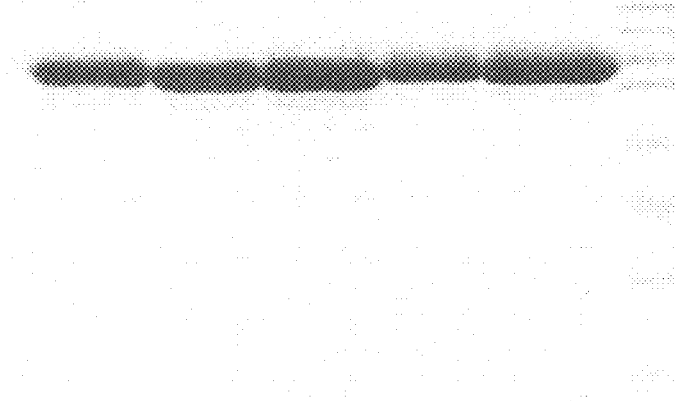
Figure 7:
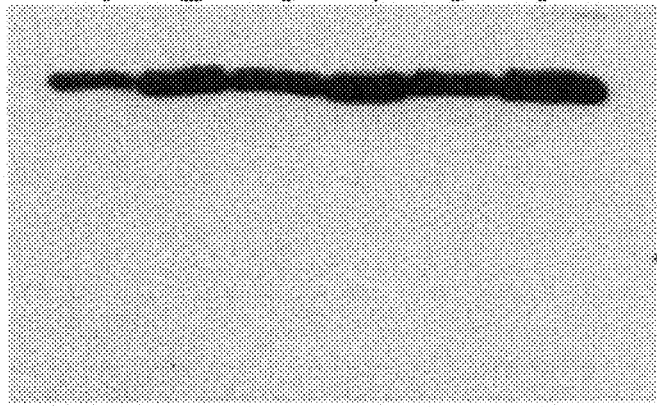
Figure 8A:
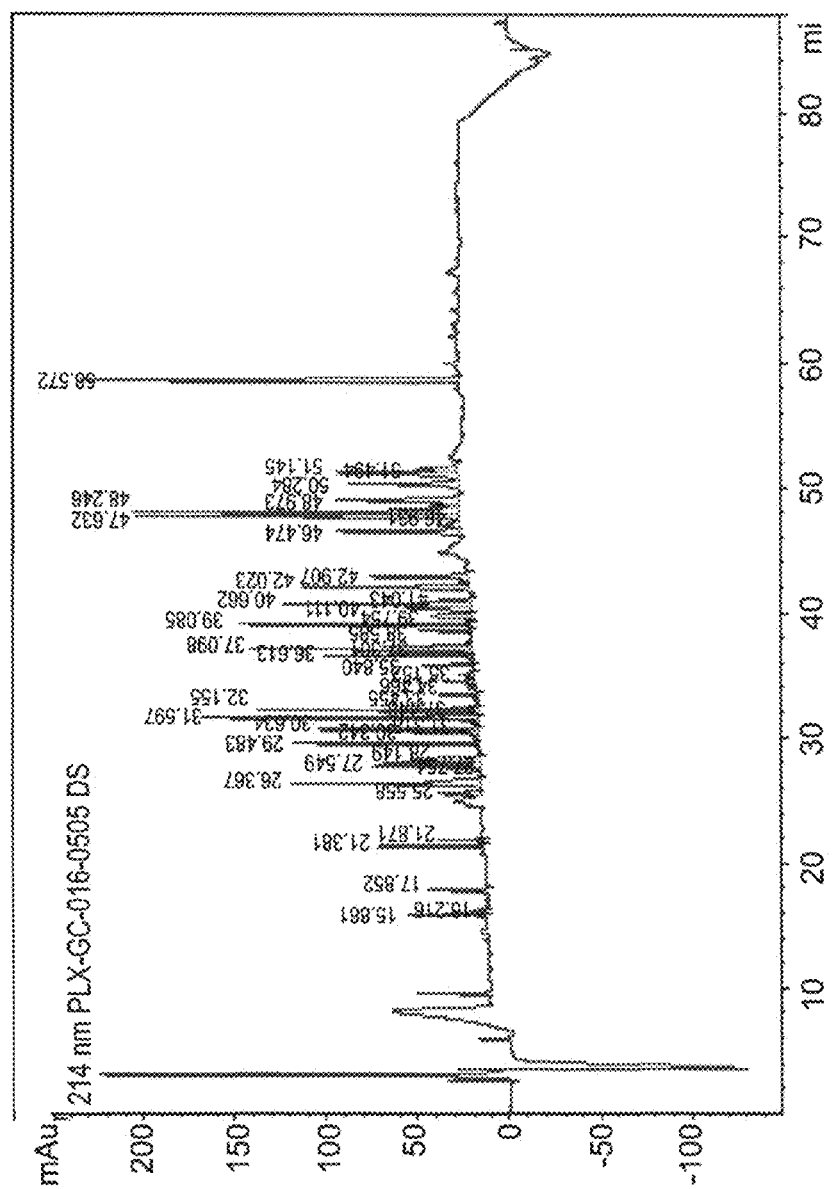
Figure 8B:
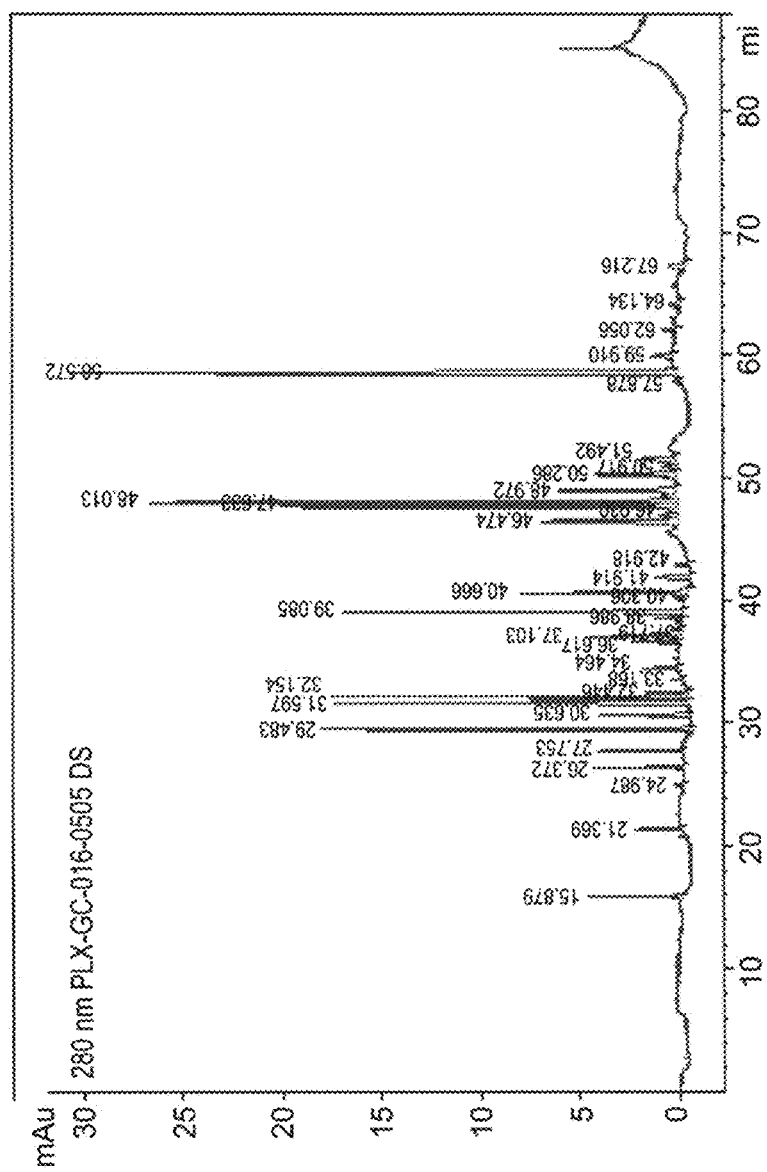
Figure 8C:
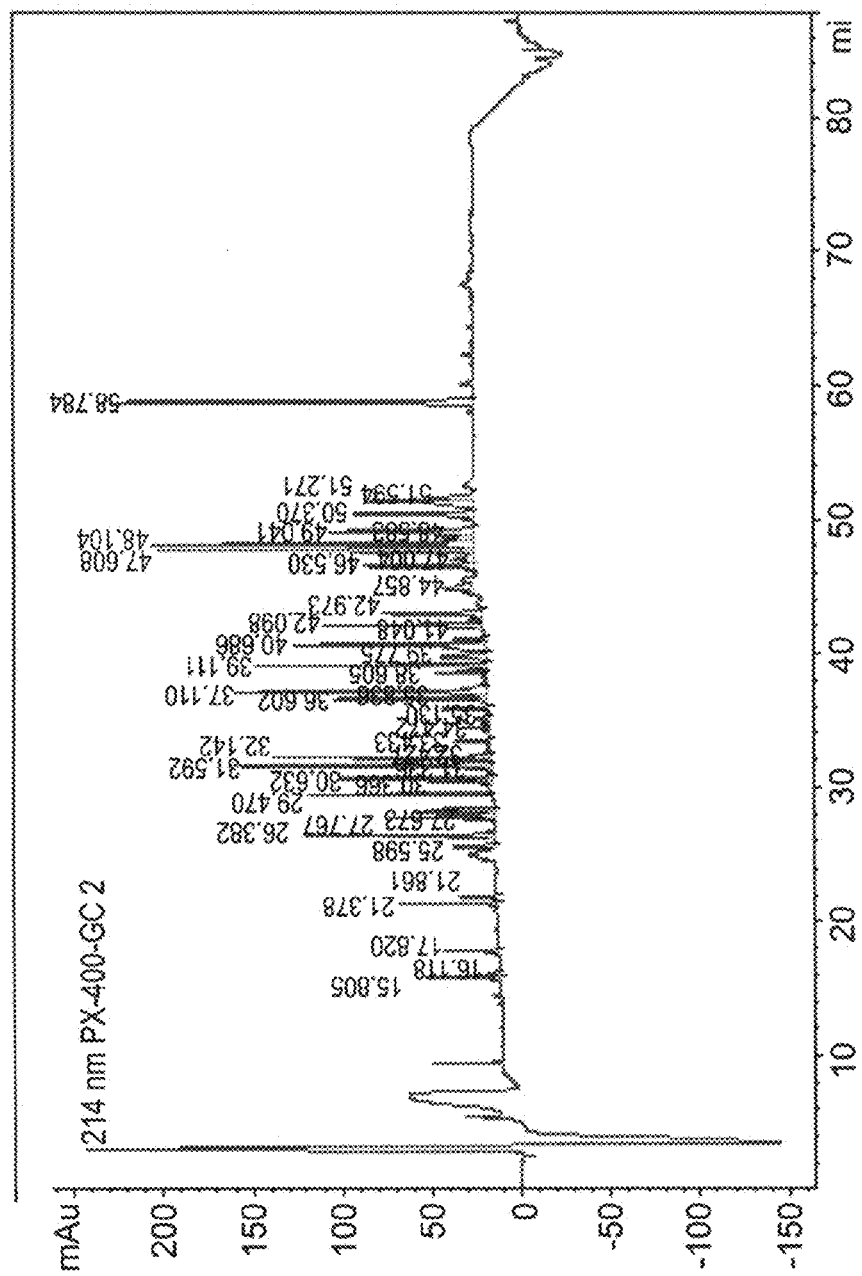
Figure 8D:
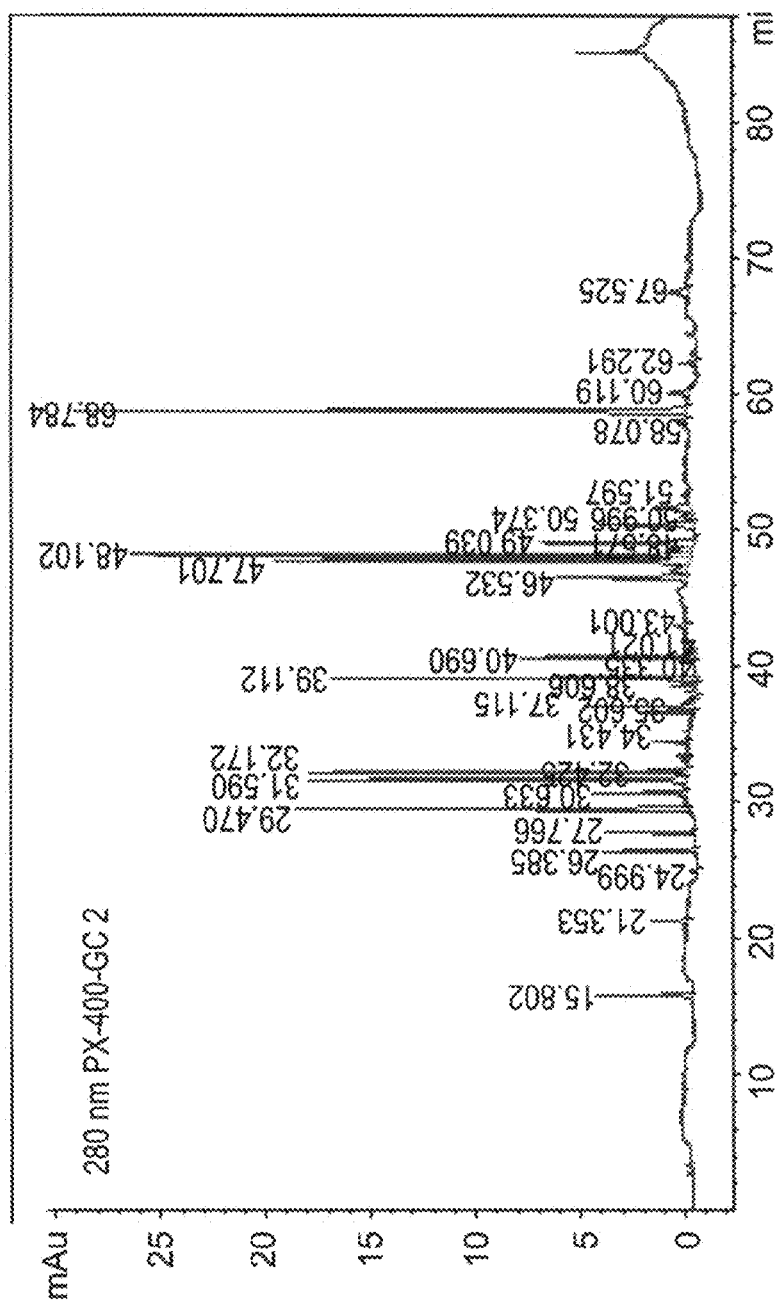
Figure 9A:
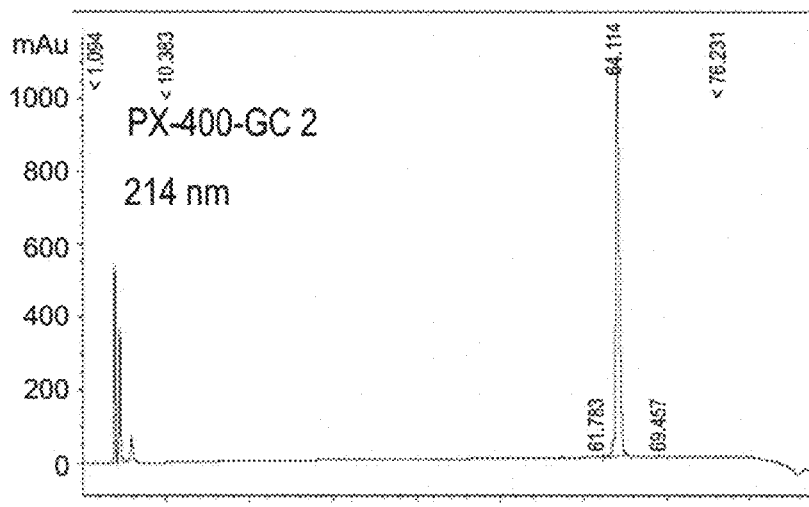
Figure 9B:
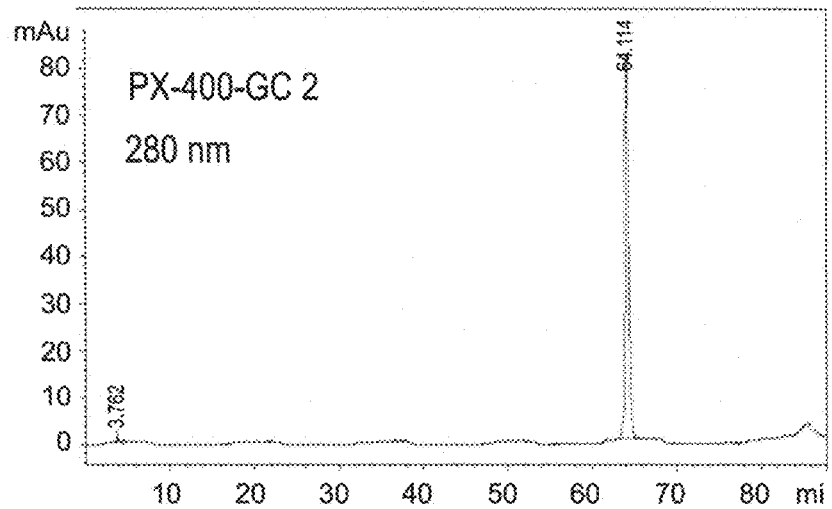
Figure 10:
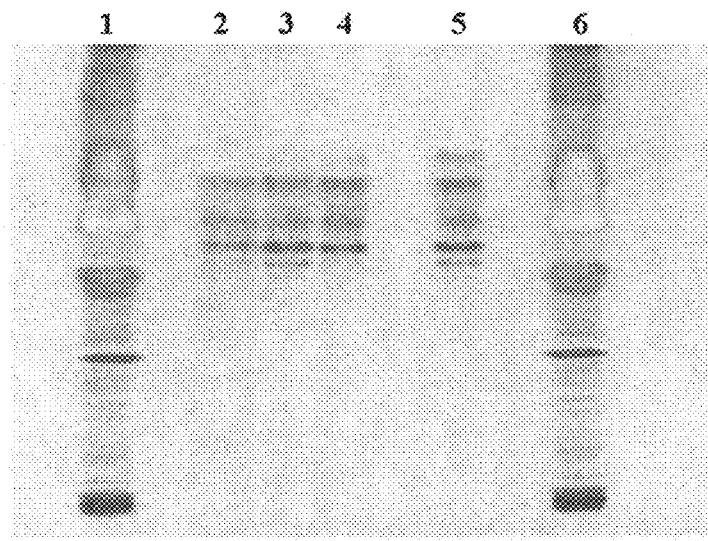
Figure 11:
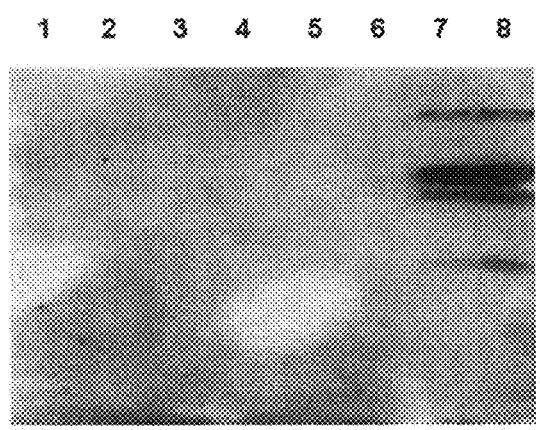
Figure 12:
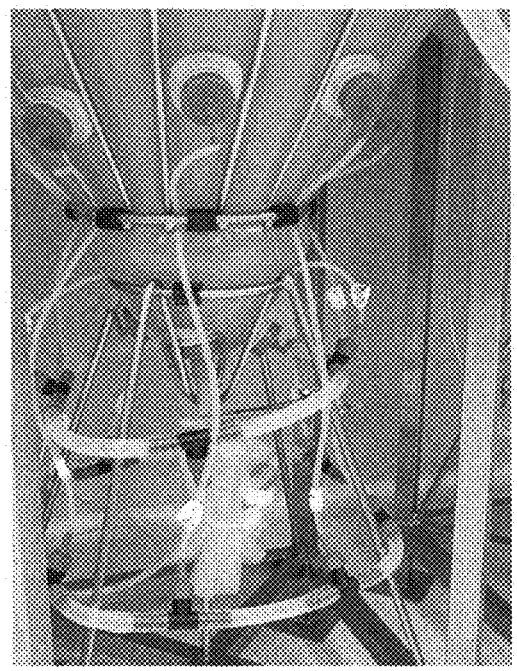

FIG. 3 is a histogram showing the superior oxygen saturation achieved in plant cell cultures using the Large-Scale Disposable Bioreactor. Carrot cells were inoculated into culture media in bioreactors of different volumes: Erlenmeyer flasks, (blue columns); 10 liter reactors (PX-10, red columns); 100 liter reactors (PX-100, white columns) and 400 liter reactors (PX-400, orange columns), and cultured for 3-4 days under optimal conditions of each system (see Materials and Methods hereinbelow). Each reactor is equipped with a sterile silicon chip [(Cat. Number SFPST3YOPSUP (Presens Presision Sensing GmbH)] for determining $O_2$ saturation at the indicated days [$O_2$ is measured using Fibox 3 (Presens Presision Sensing GmbH)]. Note the superior levels of $O_2$ saturation in the large scale (PX-100 and PX-400) bioreactors;

FIG. 4 is a photograph of a Western blot showing the superior production of recombinant GCD using the Large-Scale Disposable Bioreactor. 5 µl samples of crude extracts at 4 or 7 day cell culture extracts from bioreactors of different volumes, prepared as described hereinbelow (see Materials and Methods), were separated on PAGE, blotted onto a nitrocellulose transfer membrane, and reacted with specific rabbit anti-GCD polyclonal antibody. Bands were visualized by SuperSignal West Pico Chemiluminescent Substrate. Lane 1—10 liter reactor with sparging; Lane 2—10 liter reactor with 8 mm bore opening; Lane 3—10 liter reactor with 100% oxygen added from day 4; Lanes 4 and 5—400 liter reactor, day 4; Lane 6—400 liter reactor, day 7; Lanes 7 and 8—100 liter reactor, day 7; Lanes 9 and 10—prGCD standard 25 ng. Note the significantly superior yield of GCD in the Large Scale Disposable Bioreactor, as compared with 10 and 100 liter reactors;

FIGS. 5a-5b are RP-HPLC analysis showing the elimination of Antifoam-C using ion exchange chromatography. 0.075% Antifoam C emulsion (Dow Corning®, Corning, N.Y.) was loaded on a 15 ml cation exchange column (Bio Rad USA), and samples of flow-through, wash and salt-gradient (0.2M NaCl; 1.2M NaCl; and 12% EtOH in 1.2M NaCl) eluate monitored at 262 nm for detection of Antifoam-C. FIG. 5a shows detection of the Antifoam-C in the solution loaded on the column. FIG. 5b shows detection of the Antifoam-C in the column flow-through. Note that absence of retention of Antifoam-C on the column;

FIG. 6 is a SDS-PAGE analysis showing the identity of GCD produced in Large Scale Disposable Bioreactors. Samples of GCD from 400 liter reactors (Lane 1, 10 µg), 80 liter reactors (lanes 2 and 3, 10 µg and 20 µg, respectively), and commercially prepared glucocerebrosidase Cerezyme (10 ng and 20 ng) (lanes 4 and 5, 10 µg and 20 µg, respectively) were separated on SDS-PAGE. Bands were visualized by staining with Coomassie blue. Lane 6 is molecular weight markers. Note the electrophoretic identity of the GCD from Large Scale, Small Scale Bioreactors, and the commercial glucocerebrosidase preparation;

FIG. 7 is a Western blot showing the identity of GCD produced in Large Scale Disposable Bioreactors. Samples of GCD from 400 liter reactors (Lanes 1, and 2, 50 ng and 100 ng, respectively), 80 liter reactors (lanes 3 and 4, 50 ng and 100 ng, respectively), and commercially prepared glucocerebrosidase Cerezyme® (lanes 5 and 6, 50 ng and 100 ng, respectively) were separated on SDS-PAGE, blotted onto a nitrocellulose transfer membrane, and reacted with specific rabbit anti-GCD polyclonal antibody. Bands were visualized by SuperSignal West Pico Chemiluminescent Substrate. Note the electrophoretic, and immunological identity of the GCD from Large Scale, small scale bioreactors, and the commercial glucocerebrosidase (Cerezyme®) preparation;

FIGS. 8a-8d are graphs showing peptide mapping (tryptic digest) of glucocerebrosidase produced in Large Scale Disposable Bioreactors. Samples of glucocerebrosidase harvested from Small Scale Disposable Bioreactors (80 liter) and Large Scale Disposable Bioreactors (400 liter) were digested with protease, separated on RP-HPLC Jupiter 4u Proteo 90A column (Phenomenex, 00G-4396-E0) to produce an amino acid "fingerprint", and the fragments monitored at 214 nm and 280 nm. FIGS. 8a and 8b are the profiles of glucocerebrosidase produced in 10 liter bioreactors (8a, detection at 214 nm; 8b, detection at 280 nm). FIGS. 8c and 8d are the profiles of glucocerebrosidase produced in 400 liter bioreactors (FIG. 8c—detection at 214 nm, FIG. 8d—detection at 280 nm. Note the identity of the product for the Large- and Small Scale Disposable Bioreactor;

FIGS. 9a-9b are graphs showing RP-HPLC analysis of glucocerebrosidase produced in Large Scale Disposable Bioreactors. Glucocerebrosidase harvested from Large Scale Disposable Bioreactors (400 liter) was purified as detailed hereinbelow, and analyzed on C-4 RP-HPLC column and monitored at 214 nm (FIG. 9a) and 280 nm (FIG. 9b). Note that the prGCD appears as a single peak with retention time of 64.12 minutes, similar to that of prGCD standard (64.70 minutes);

FIG. 10 is a photograph of an IEF gel showing the superior purity of the prGCD produced using Large Scale Disposable Bioreactor. Samples of prGCD produced in the Large Scale Disposable Bioreactor (400 liter), and purified in the 5 column purification process described hereinbelow were separated on an isoelectric focusing gel along with prGCD purified from Small Scale Disposable Bioreactor (10 liter). Lane 2—Large Scale, $3^{rd}$ purification stage; Lane 3—Large Scale, $4^{th}$ purification stage; Lane 4—Large Scale, $5^{th}$ purification stage; Lane 5—Small Scale; Lanes 1 and 6, IEF PI standards. Note the identity, and high level of purity of the prGCD from Large Scale Disposable Bioreactor at all stages of purification;

FIG. 11 is a Western blot showing the purity of prGCD produced using Large Scale Disposable Bioreactor. Samples of GCD from 400 liter reactors (lanes 1 and 2, 50 ng and 100 ng, respectively), 80 liter reactors (lanes 3 and 4, 50 ng and 100 ng, respectively), commercially prepared glucocerebrosidase Cerezyme (lanes 5 and 6, 50 ng and 100 ng, respectively) and carrot host proteins (CHP) (lanes 7 and 8, 50 ng and 100 ng, respectively) were separated on SDS-PAGE, blotted and reacted with specific anti-CHP polyclonal antibody. Bands were visualized by SuperSignal West Pico Chemiluminescent Substrate. Note the absence of impurities in the Large Scale Disposable Bioreactor, as in all the other prGCD preparations;

FIG. 12 is a photograph of the bottom end of an exemplary disposable bioreactor of the present invention, showing multiple gas inlets for providing aeration and mixing of the culture medium, and an exemplary conical rigid support structure.

Figure 13:
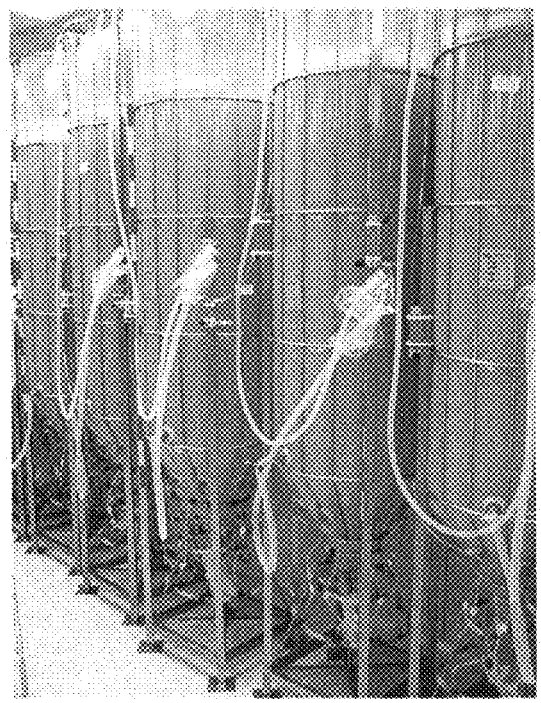
Figure 14:
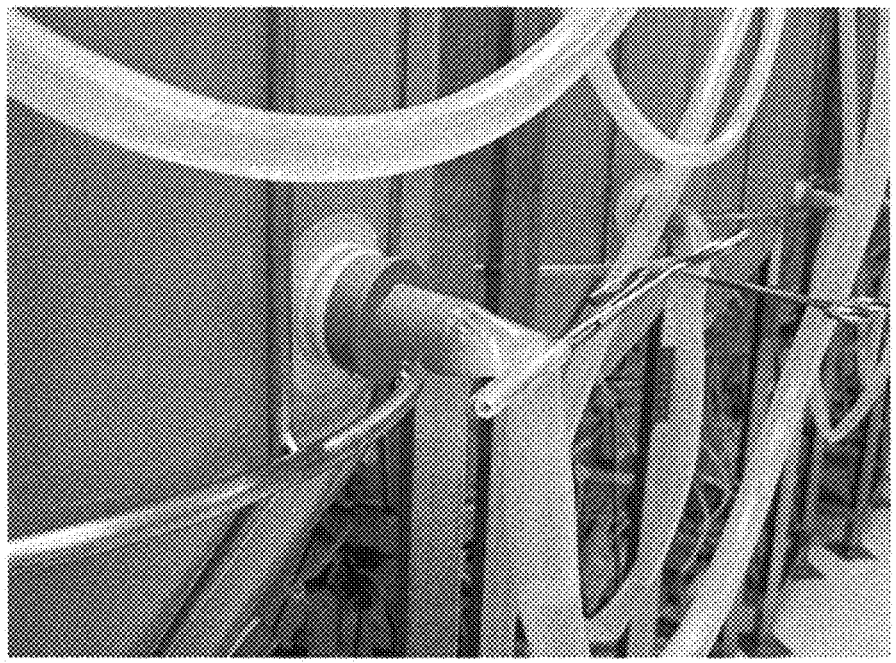
Figure 15:
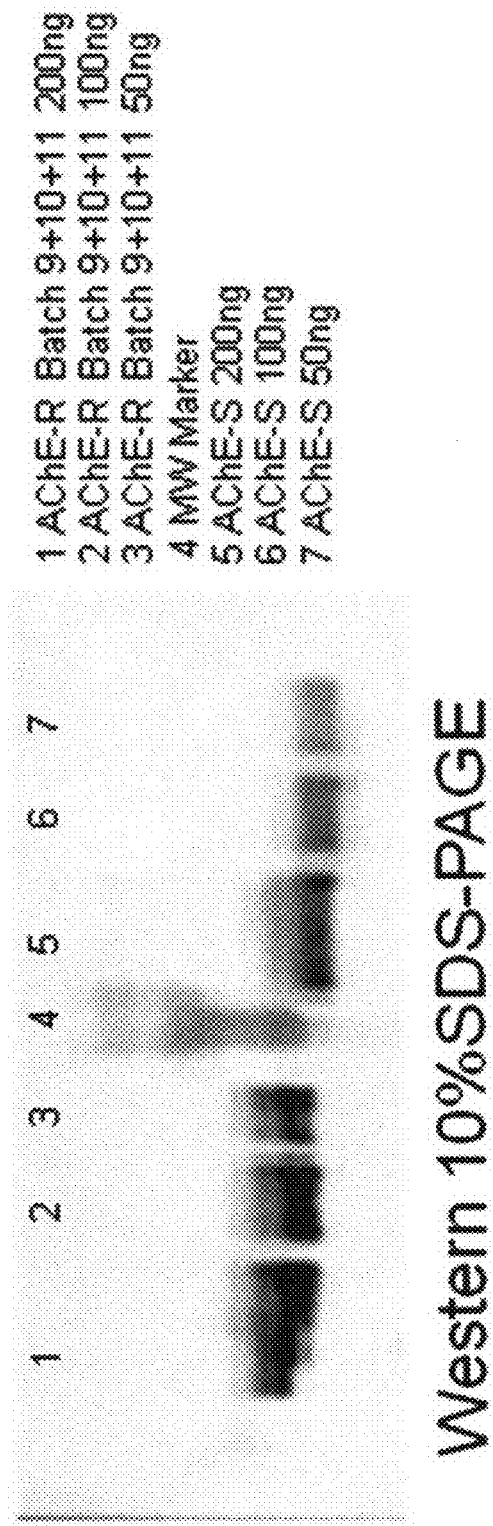
Figure 16:
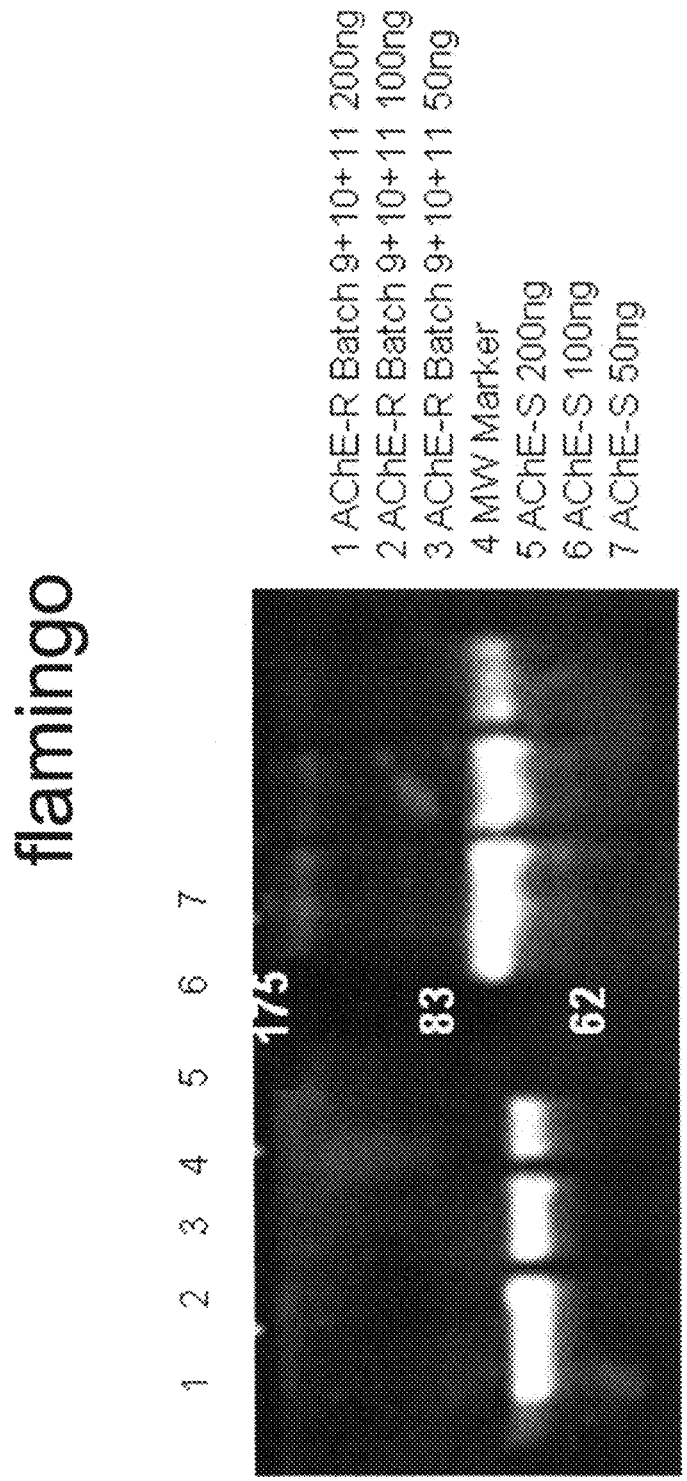
Figure 17:
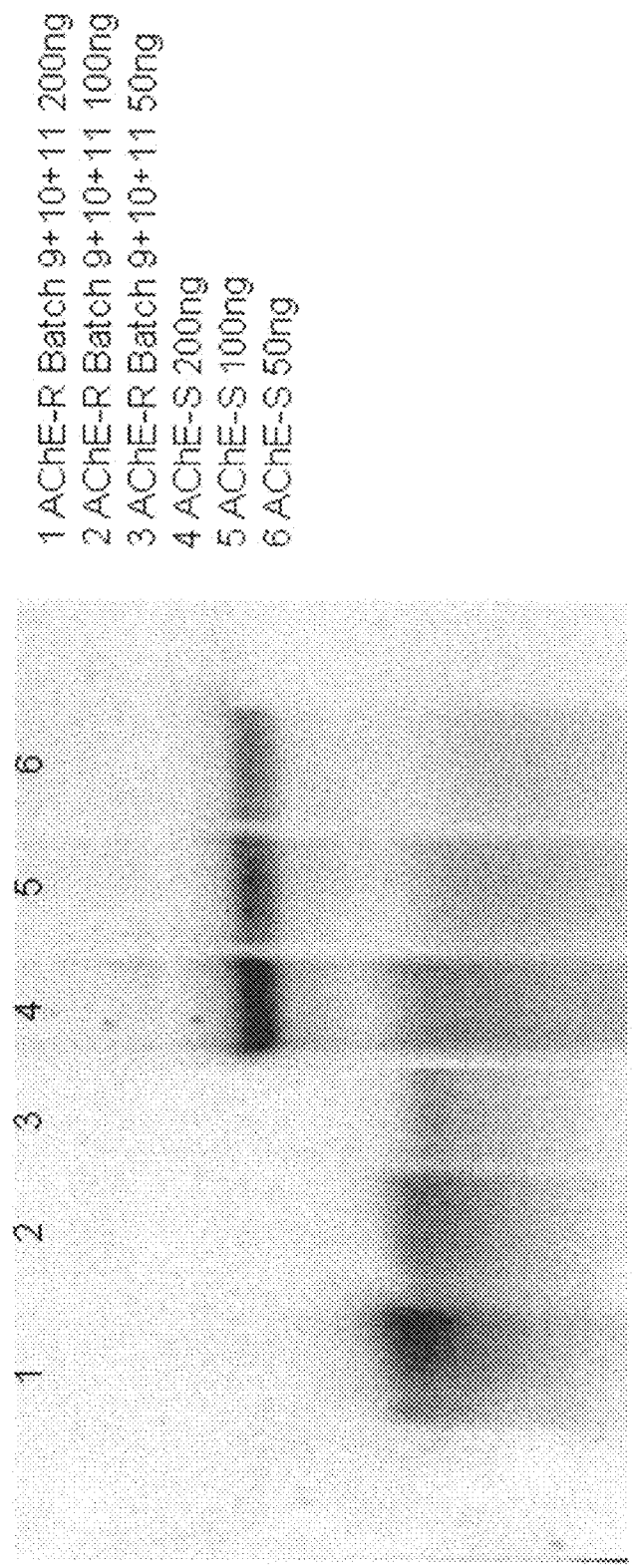

FIG. 13 is a photograph showing a battery of exemplary Large Scale Disposable bioreactors of the present invention;

FIG. 14 is a photograph of an exemplary bioreactor of the present invention showing a reusable harvesting port;

FIG. 15 is a photograph of Western blot showing immunodetection of plant-expressed human recombinant AChE. 50 (lanes 3 and 7), 100 (lanes 2 and 6) and 200 ng (lanes 1 and 5) of recombinant human AChE-R produced in a Large Scale Disposable Bioreactor according to one embodiment of the present invention (lanes 1-3) and commercially available recombinant human AChE-S (lanes 4-6) were detected using an affinity purified goat polyclonal antibody raised against a peptide at the N-terminus of AChE of human origin (Santa-Cruz Biotechnology, Santa Cruz, Calif.) (identical in AChE-R and AChE-S). Lane 4 is Molecular Weight standards. Strong antibody binding is evident in all samples;

FIG. 16 is a photograph of Flamingo™ non-specific protein staining of SDS-PAGE gel of plant-expressed human recombinant AChE-R, produced in a Large Scale Disposable Bioreactor according to one embodiment of the present invention, as compared to the profile of commercially available AChE-S. Plant expressed AChE-R (lanes 1-3) and mammalian-cell produced AChE-S (lanes 5-7) were separated as in FIG. 13, and the gel stained with Flamingo™ reagents as described herein. Note that the AChE-R migration profile corresponds to that of the AChE-R detected by immunoassay using anti AChE antibodies (FIG. 13, above). Furthermore, the single band observed on the gel as shown in FIG. 13 indicates efficiency of purification;

FIG. 17 is a Karnovsky assay gel stained to detect acetylcholinesterase catalytic activity in plant cells cultured in a Large Scale Disposable Bioreactor. Catalytically active acetylcholinesterase-R was purified from BY-2 cells harvested from pooled batches of cells, cultured in a 400 L Large Scale Disposable Bioreactor according to one embodiment of the present invention. Decreasing amounts of protein purified from cells (lanes 1 and 4=200 ng; lanes 2 and 5=100 ng, lanes 3 and 6=50 ng) were separated on a 10% native polyacrylamide gel under non-denaturing conditions, washed and treated to reveal acetylcholine catalytic activity (Karnovsky stain). Corresponding amounts of acetylcholine-S (lanes 4-6) were included as a controls. Electrophoresis of AChE-R and AChE-S was performed in 10% native polyacrylamide gel under non-denaturing conditions. Gels were run at 4° C., rinsed 3 times with H2O and incubated for 1 h with agitation in buffer containing acetylthiocholine (0.5 mg/mL; Sigma), sodium acetate (65 mM, pH 6.0; Sigma), sodium citrate (5 mM; Sigma), cupric sulfate (3 mM; Sigma), and potassium ferricyanide (0.5 mM; Riedel De Haen). Catalytic activity was visually detected. Upper arrow indicates migration of the tetramer of AChE-S. Lower arrow indicates migration of monomeric AChE.

DESCRIPTION OF THE PREFERRED EMBODIMENTS

The present invention is of a reusable, disposable device for culturing plant tissues or cells. Specifically, the device of the present invention includes a non-rigid container having dimensions and gas exchange ports designed for maintaining dissolved oxygen concentration and shear forces suitable for culturing plant tissue or cells in 400 liters or more of culture medium. Such a device can be used for culturing transformed plant cells for the production of recombinant, plant-derived biologically active materials (e.g. pharmaceuticals) from the cells and/or culture medium. Also provided is a plant cell culturing system using the device of the present invention.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As described hereinabove, scale-up to large volumes of disposable bioreactors requires unique solutions to the problems of aeration and mixing. Some prior art bioreactors have employed gas for this purpose. US Patent Application No. 2005/0282269 to Proulx et al. discloses a disposable bioreactor having multiple gas inlets with built-in gas diffusers and filters at the inlet ports, positioned at the bottom end of the container, in order to provide aeration and mixing. Such a configuration is limited in that the filters being in contact with the liquid medium, would tend to become blocked and interfere with adequate gas supply. No volume capacity or dimensions are disclosed.

Another type of disposable bioreactor using gas for aeration and agitation is offered by Cellexus Biosystems, PCC (Cambridge, England). This bioreactor is a flexible bag having an integral sparger tube affixed or placed along the inside bottom end of the device, for introducing air or gas for aeration and mixing. The bioreactor bags of Cellexus are designed according to a unique, asymmetrical geometry, which concentrates the majority of the bag's fluid volume in the upper half of the bioreactor. This design requires a specially designed support enclosure (Cellmaker Lite™) for operation.

U.S. Pat. No. 6,432,698 to Gaugler et al. discloses a flexible, disposable culture bag for culture of nematodes. The culture bag is outfitted with a gas inlet and diffuser, in the form of a tube, for the aeration and mixing of the culture medium. Volumes of up to 200 liters are envisioned, although no reduction to practice is provided. No specific dimensions are disclosed.

US Patent Application No. 2005/0272146 to Hodge et al. discloses a 150 liter disposable bioreactor having integrated impellor blades for mixing. Mixing of culture medium in bioreactors by impellor is known to create shear forces unsuitable for culturing plant cells.

U.S. Pat. No. 6,391,683 to Shaaltiel et al., (which is hereby incorporated by reference as if fully set forth herein) discloses disposable culturing devices comprising non-rigid bags having gas inlet and outlet ports, designed either for a single use, or for multiple cycles of culture and harvest. The device employs air pressure through carefully regulated bubble volume and number, to mix and aerate the culture. Efficient culture of transformed plant cells accurately expressing a variety of heterologous (mammalian and non-mammalian) recombinant proteins has been reported using the bioreactors as described by Shaaltiel (see U.S. Pat. No. 6,391,683, U.S. patent application Ser. No. 10/784,295; International Patent Publications PCT Nos. WO2004/091475, WO2005/080544 and WO 2006/040761, all of which are hereby incorporated by reference as if fully set forth herein). However, Shaaltiel et al., in U.S. Pat. No. 6,691,683, discloses a design suitable for smaller and medium size volumes, limiting the yields of the recombinant proteins synthesized therein.

While reducing the present invention to practice, the present inventors have designed a large scale, reusable disposable bioreactor constructed of transparent or translucent, non-rigid materials. The bioreactor has sampling ports enabling use for at least two consecutive cycles of culture, specific dimensions and gas exchange ports providing gas in a manner sufficient to mix and aerate a cell culture in the bioreactor with suitable dissolved oxygen concentration and shear forces for efficient growth of plant cells in volumes greater than 400 liters.

Thus, according to one aspect of the present invention there is provided a disposable device for culturing and harvesting plant tissue and/or cells.

The device of the present invention includes a non-rigid container having a volume of at least 400 liters and being configured with gas exchange ports and a harvesting port enabling the device to be used continuously for at least two consecutive culturing/harvesting cycles.

Although the present device can be used for culturing any type of cell or tissue, it is designed to enable efficient large scale culturing of plant cells and tissue.

Oxygen saturation of the medium is crucial for efficient growth of cells and recombinant protein expression, and therefore critical to the proper operation of bioreactors and their use in production of recombinant cell products. Oxygen saturation of bioreactors for plant cell culture growth is even more important, since plant cells are more susceptible to fluctuations in oxygen saturation than bacteria or mammalian cells (see Schlatmann et al, Biotech. Bioeng., 1995; 45:435-39). Further, plant cells are sensitive to the hydrodynamic environment in conventional bioreactors, most probably due to larger plant cell sizes, extensive vacuolization and aggregation patterns. Thus, while aeration of the culture medium by introduction of gas bubbles into the container also provides mixing, shear forces detrimental to fragile plant cells must be avoided. Recently, plant cells in culture have shown to be susceptible to sublethal shear forces, responding with a characteristic "sub-lytic" response, which in turn significantly limits the efficiency of plant cell bioreactors (Namdev and Dulop, App. Biochem and Biotech, Part A, Frontiers in Bioprocessing, 1995).

Thus, the device of the present invention maintains oxygen saturation and shear forces suitable for culturing plant tissue and/or cells in volumes of 400 liters or greater, by employing parameters, or combination of parameters critical for determining oxygen saturation and shear forces in culture.

Oxygen saturation and shear forces suitable for culturing plant tissues and/or cells in the device are maintained by a combination of values or value ranges of: a) a height to volume ratio; b) an inlet gas pressure; c) a density of gas inlets per cross sectional area; d) an aeration rate at the inlet; and e) a gas bubble volume at the inlet.

Height to Volume Ratio:

Mechanical mixing methods are unsuitable for use in plant cell bioreactors, especially where large volumes of medium are being processed. Aeration and mixing of the culture medium in a large scale bioreactor can be accomplished by the movement of gas bubbles through the medium. The more extensive the contact of the gas bubble with the medium, the greater the potential for gas exchange, and the more efficient the mixing action of the gas in the medium. Thus, while the height to volume ratio of smaller volume bioreactors may have allowed greater flexibility, the height to volume ratio of bioreactor devices to be used with large volumes (e.g. 400 liters or more) must be maintained within a range of about 0.06 to 1 centimeters per liter. Height to volume ratio can be calculated from the height (length) of the container of the device and the average cross sectional area of the device. As used herein, volume of the device is the height times the cross sectional area. For example, for a bioreactor having a height (length) of 200 centimeters and a volume of 400 L (having, for example an average radius of about 25 centimeters), the height to volume ratio is 200/400, or 0.5; for a bioreactor having a height of 300 cm and a volume of 3000 L, the height to volume ratio is 300/3000, or 0.1 Examples of ranges of height to volume ratios suitable for use with the bioreactor of the present invention are about 0.06 to 1 centimeters per liter, preferably about 0.1 to about 0.5, most preferably about 0.44 centimeters per liter.

Further, it will be appreciated that the height to volume ratio can be calculated using either the total potential fillable internal volume of the container, or using a designated portion thereof, which is the operating, functional fillable internal volume of the container, without the "headspace" typically found above the fluid level in a bioreactor.

Inlet Gas Pressure:

In order to provide sufficient gas (for example, air or oxygen) for mixing and aeration of the culture medium of the large scale bioreactor, gas pressure at the inlet(s) needs to be sufficient to overcome the downward force of the column of liquid in the bioreactor, and at the same time avoid shear forces associated with creation of too many bubbles, or bubbles of unsuitable size for plant cell culture. Large scale bioreactors of the present invention, having a height to volume ratio suitable for plant cell culture, require greater gas pressure at the gas inlet than in smaller volume bioreactors. Gas pressure is expressed in bar units, wherein 1 bar is 100,000 pascals (Pa), or 1,000,000 dynes per $cm^2$. Pressure gauges for monitoring and pressure regulators for control of gas pressure at gas inlet(s) are well known in the art, and widely commercially available. Examples of ranges of inlet gas pressures suitable for the bioreactor of the present invention are in the range of about 1.5 bar to about 4 bar, more preferably about 1.5 bar to about 2.5 bar.

Density of Gas Inlets Per Cross Sectional Area:

Small volume bioreactors are typically limited to a single or very few gas inlets in order to provide sufficient gas bubbles, of the desired volume, for mixing and aeration of the culture medium in the bioreactor vessel. On the other hand, large volume bioreactors, such as the devices of the present invention, require a greater density of gas inlets in order to overcome the compressive forces of the column of culture medium in the device, and achieve the ranges of inlet gas pressure required to provide mixing and aeration in a manner suitable for use with plant cell cultures. In order to provide control over the pressure at gas inlet(s) and maintenance of bubble size optimal for mixing and aeration of the culture medium in the large volume bioreactor, a plurality of gas inlets are provided, positioned at a given density on the disposable, non-rigid container of the device. The density of gas inlets is expressed as number of inlets per square meter outer surface of the container of the device. Examples of ranges of density of gas inlets suitable for use in the bioreactor of the present invention are about 20 inlets per square meter of the surface of the container, to about 70 inlets per square meter. Preferably, the density of gas inlets per cross sectional area is about 40 to 60 inlets per square meter, more preferably 55 inlets per square meter.

Aeration Rate at the Inlet:

Increased aeration generally (i.e.—the presence of a more rapid gas exchange), and increased oxygen specifically, both increase the rate of growth of cells in culture. Smaller volume bioreactors for plant cell culture have typically provided air at an aeration rate of 0.15-0.3 vvm (volume air per volume medium per minute), at the gas inlet, with increased aeration rate as volume increased. However, the effectiveness of air bubbles in promoting cell circulation is different in smaller enclosed volumes than in a larger equivalent volume, thus a nonproportional aeration rate is required for promoting air circulation and oxygen distribution in a large volume, compared to that in a number of smaller volumes having the same combined volume of medium.

While reducing the present invention to practice, inventors have surprisingly found that rather than proportionally increasing aeration rate (vvm) with increasing volume, improved results were achieved by reducing the range of aeration rate, measured as vvm, in large scale bioreactors. Examples of ranges of aeration rates at the gas inlet(s) suitable for culturing plant cells in a large volume bioreactor are about 0.05-0.12 vvm, and preferably about 0.07 vvm to about 0.1 vvm. The advantage of such reduced aeration rates include greater yield in large volume bioreactors, and improved energy efficiency, greatly significant in industrial scale culturing.

Gas Bubble Volume at the Inlet:

The importance of suitable mixing apparatus in large scale reactors cannot be overstated. In some cases, particularly relating to plant cells, gas bubble size is of great importance for efficient culture and growth of cells in a bioreactor. Small bubbles may actually damage the plant cells, and a mean bubble volume of not less than 20 cubic millimeters substantially overcomes this potential problem. Thus, along with gas pressure and number of inlets, control of gas bubble volume at the inlet is important for achieving mixing and aeration of the culture medium effective for growth of plant cells. While the size of the bubbles delivered by the gas inlet(s) will vary according to the use of the device, examples of suitable ranges of gas bubble volume at the inlet is from 20 to over 1800 cubic millimeters volume, preferably about 40 cubic millimeters to about 1000 cubic millimeters, more preferably about 100 cubic millimeters to about 500 cubic millimeters, most preferably about 300 cubic millimeters. In cases where smaller bubbles are desired a sparger may be used at the gas inlet to reduce the size of the bubbles, but not to below suitable size for large scale plant cell bioreactors.

The disposable bioreactor of the present invention therefore has a number of advantages over presently known devices, including but not limited to, providing large volume culture conditions while maintaining superior aeration and non-mechanical mixing of plant cell culture and medium, according to the parameters mentioned herein, thus achieving superior yields and purity of the cultured cells and products derived from the cells.

Figure 1:
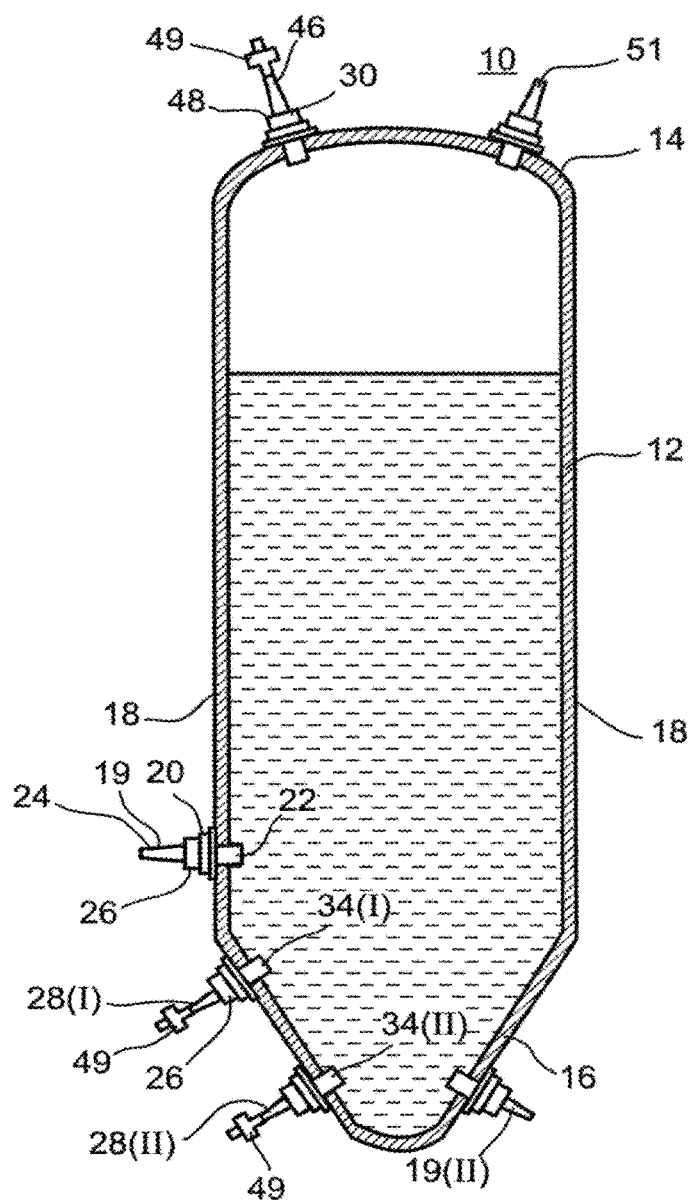

FIG. 1 illustrates an embodiment of the device of the present invention which is referred to herein as device 10.

As shown in FIG. 1, device 10 includes a container 12 which serves for culturing and harvesting plant tissue and/or cells. Container 12 is shown partially full with a liquid and thus in its inflated (and relatively rigid) state in FIG. 1, however, it should be noted that container 12 is preferably constructed as a non-rigid container (e.g. constructed from flexible materials). Thus, the pressure of the contents of container 12 on the container walls maintain the shape of container 12. When empty, or partially filled, container 12, by nature of its non-rigid design, can be partially or completely collapsed. This feature of container 12 facilitates storage and transport when empty. Container 12 has an internal volume which can accommodate between about 400 liters and about 30000 liters, more preferably between about 500 liters and 8000 liters, most preferably between about 600 and 3000 liters. Container 12 can have a typical height-to-volume ratio of about 0.06-1 centimeters to liter.

Container 12 is preferably constructed from a polymer such as polyethylene, polycarbonate, a copolymer of polyethylene and nylon, polyvinyl chloride (PVC), ethyl vinyl acetate (EVA) and ethylene vinyl alcohol (EVOH). Varying grades, densities and types of polymers can be used, such as low density polyethylene (LDPE), very low density polyethylene (VLDPE), ultra-low density polyethylene (ULDPE), linear low density polyethylene (LLDPE), and the like. Container 12 can be constructed by welding from polymer sheets, blow molding from melted polymers, or any other standard plastic-polymer manufacture method know in the art.

In a preferred configuration, container 12 is constructed from a laminate of several layers of one or more types of polymers. The laminate can contain 2, 3, 4 and up to 7, 9, or more layers, which can be made of similar or different flexible materials, of varying thickness, the materials and thickness selected, for example, according to the fluid volume of container 12. The layers can be produced by co-extrusion. Laminates can be designed to provide specific smoothness or rough texture to the inner and outer surfaces of the container, greater or lesser tensile strength, elasticity, softness, flexibility, toughness, durability, processability, etc. The material can be selected having low levels, or preferably devoid of inactivated animal derived processing agents. Slip and/or antiblock agents such as silica or diatomaceous earth can be included in the laminate layers to reduce friction and/or prevent self adhesion.

Container 12 of the present invention can be made from materials designed to provide a transparent and/or translucent character to the container, in some embodiments, the material can also be non translucent where light will be damaging for the cells or the product. As used herein, transparent is defined as clear, easily transmitting most if not all light, while translucent is defined as transmitting some, but not all light. In one embodiment, the device is for plant cells in culture, which do not have the ability of photosynthesis. In another embodiment, wherein the device is used for culture of other types of cells, e.g., moss cells, or algae cells, photosynthetic bacteria having photosynthetic capabilities, can be grown in the device. Preferably, light transmitted into the internal volume of the container is of wavelengths suitable for use by the photosynthetic and other light-gathering pigments of the plant cells cultured in the bioreactor. Light might also be needed for the production of secondary metabolites, e.g. anthocyanin, by wine grape cells. More preferably, container 12 is designed from materials allowing visual or instrumented (e.g. spectrophotometry) observation and/or monitoring of the internal volume, in order to detect changes in the culture and/or culture medium potentially indicative of the state of the culture (e.g. color, cell coagulation, turbidity resulting from contamination).

Container 12 can be fabricated at any desirable configuration, preferred is a tapering sleeve-like configuration which has a top 14 and a bottom 16 (conical in FIG. 1) connected via two side walls 18 which are flat when container 12 is empty and provide a substantially cylindrical cross sectional shape when container 12 is full. Other cross sectional shapes such as rectangular or polyhedral, for example, may also be suitable.

It will be appreciated that the cylindrical shape is most suited for cell culture containers, providing most even and unimpeded fluid flow throughout, for mixing with minimal turbulence and generation of undesired shear forces detrimental to the plant cell cultures. Preferably, bottom 16 is suitably shaped to minimize sedimentation. For example, bottom 16 can be substantially frusta-conical (as shown in FIG. 1) at least having an upwardly sloping wall or walls While reducing the invention to practice, the inventor has found that this shape is superior over a conical shape for avoiding sedimentation of cells, which can enhance decay and cell death thus influencing the overall viability of the culture. Alternatively, bottom 16 can be substantially cylindrical or alternatively convex. The aforementioned configurations of bottom 16 enable gas supplied to container 12 near bottom 16 to induce a mixing motion to the container contents effectively minimizing sedimentation thereat. Nevertheless, bottom 16 may be substantially flat in other embodiments of the present invention.

Container 12 can be fabricated by bonding/welding two panels (forming side walls 18) of suitable material. For example, two sheets of a polymeric material may be cut in an approximately elongated rectangular shape and placed one over the other. The sheets are then fusion bonded together in a manner well known in the art to form seams along the edges of the two longer sides, and along the periphery of one of the shorter ends, and again parallel and inwardly displaced thereto to form a seam at top 14 of the container.

Bottom 16 of the container can be formed by fusion bonding the remaining short end of the sheets along two sloping seam lines, mutually converging from the seams of the long sides. Optionally, the two sloping seam lines may be joined above their apex by another fusion welded seam line approximately orthogonal to the long side seams. Prior to fusion welding the two sheets together, rigid plastic bosses can be fusion welded at locations corresponding to attachment points for corresponding input and output ports (further described below).

Container 12 can also be fabricated from a continuous sleeve of flexible polymeric material, eliminating the need for welding seams along the long sides of the container, and providing a continuous, unbroken circular cross-section throughout most of the height of the container. Using a sleeve of material for fabrication is desirable since absence of weld seams minimizes turbulence and shear forces during aeration and mixing of the culture medium.

As is shown in FIG. 1 container 12 further includes a harvest port 19I for harvesting at least a portion of the medium containing cells and/or tissue thereby enabling device 10 to be used continuously for at least two consecutive culturing or harvesting cycles, without need for cleaning, sterilization and/or testing in between the cycles. Alternatively, harvesting can be effected via an additional harvesting port (19II) located at the bottom of the bioreactor for draining all of bioreactor contents, thus enabling harvest of the entire culture within the bioreactor. A remaining second portion of medium containing cells and/or tissue serves as inoculant for a next culture and harvest cycle, wherein culture medium and/or required additives can be provided, as described below. Harvest port(s) 19 may also be used to introduce the original volume of inoculant into the container, as well as for enabling the harvested material to flow therethrough and out of the container.

Harvest port(s) 19 include(s) a harvest pipe 20 having a harvest inlet 22 which is in fluid communication with the internal volume of container 12, and a harvest outlet 24 which is positioned outside container 12. Alternatively harvest port(s) 19 can be made of a single orifice, welded into the container 12, which contacts the internal volume from the internal side, and has an outlet to the external side of the container. Harvest pipe 20 can be made from a polymeric material or alloy as is well known in the art.

Since harvesting is oftentimes hindered by the presence of cell clumps, harvest pipe 20 is preferably fabricated having a large internal diameter (e.g. in the range of 1-10 cm) and/or having a degree of elasticity allowing evacuation of clogs.

The position of harvesting port(s) 19 is selected according to the volume of container 12, such that the portion of medium and cells and/or tissue that remains is a predetermined fraction of the volume of container 12 (e.g. 5-35%).

Harvest port 19 can be located at a position near the bottom of container 12 which enables harvesting of most of container 12 contents while retaining a portion of medium containing cells and/or tissues for use as an inoculum.

Alternatively, or additionally, a harvest port 19II can be located further down bottom 16 of container 12, and the operator could then optionally manually ensure that a suitable portion of medium containing cells and/or tissue could remain in container 12 after harvesting a desired portion of medium and cells and/or tissue. Having port 19II at a position lower down bottom 16 enables removal of all or most of the medium.

It will be appreciated that although said positions of harvesting port(s) 19 and 19II are presented as alternatives above, both can be incorporated into a single device 10 providing an operator with alternative harvesting ports.

Harvest port(s) 19 further includes a flow regulator 26. Flow regulator 26 can be, for example, a valve for regulating the flow of material into or out of container 12 via harvest port(s) 19. Flow can also be regulated via an aseptic connector which is made from a durable, sterilisable material such as glass, stainless steel, rigid plastic, and the like. Harvest port(s) 19 can also include a contamination preventer (not shown), such as a fluid trap, in order to prevent the unintentional introduction of material into container 12 following harvesting.

Container 12 can include an additional sampling port which is similar in construction to harvest port(s) 19 and can be positioned in proximity to harvest port 19. Container 12 further includes an optional additional additive inlet 51, for introduction of medium or other additives. In some embodiments, additive inlet 51 is located in the top end of container 12, in communication with the "headspace" above the culture medium. In other embodiments, additive inlet 51 is located nearer to the middle portion or the bottom end of container 12. In other embodiments, additive inlet 51 can also include a contamination preventer (not shown), such as a fluid trap, in order to prevent the unintentional introduction of material into container 12 during or following addition of media, etc.

Device 10 further includes gas exchange ports for communicating gases into and out of container 12. Gas exchange ports include at least one gas inlet port 28, for percolating gas (such as air, oxygen or other gases) through the medium, for aeration and mixing of the plant cell culture, and at least one gas exhaust port 30, for venting of gas which percolate through the contents of container 12 (e.g. culture medium and cells). Gas inlet ports and outlet ports can be equipped with a filter 49, described in detail herein. In one embodiment, a plurality of gas inlets is provided in order to better distribute the air pressure while providing the necessary inflow for desired flow of air bubbles.

Gas inlet port(s) 28 can be connected to a gas supply (e.g. pump) via a gas supply tube or tubes.

Gas inlet port 28 can be made from flexible (e.g. silicone) or rigid material (e.g. stainless steel). Gas inlet 34 (gas inlet 34(I) corresponds to gas inlet port (28(I) at position I, and gas inlet 34(II) corresponds to gas inlet port 28(II), at position II) of gas inlet port(s) 28 is designed to provide gas bubbles of volume suitable for aerating and mixing the plant culture medium, and preventing sedimentation, without generating undesirable shear forces, as described hereinabove. Gas inlet 34 can be varied in shape (narrow, wide, tapered, conical, rounded, etc) to provide a desired bubble shape and size. Alternatively the port can be fashioned in one piece with different diameters in inner and outer opening, as described for the harvesting port 19.

Gas exchange ports 28 and 30, harvest port(s) 19 and the optional sampling ports are formed by creating an opening in the surface of the container 12 and reinforcing the opening around the port with additional rigid or non-rigid material as is well known in the art.

In order to provide suitable mixing and aeration, a plurality of gas inlet ports 28 can be provided at a density of 20 to 70 inlets per square meter. Gas inlet ports 28 can be positioned around the perimeter of container 12 at a predetermined distance from bottom end 16 thereof. Location of gas inlet ports 28 is determined by the volume and height of the container, and by the type of aeration desired for specific plant culture uses. Gas inlet ports 28 can be located 15 to 65 centimeters from bottom 16 of the container. In one embodiment of the invention, at least one of the gas inlet ports is at a location below the level of harvesting port 18.

Additional gas inlet ports 28 can be provided as needed, for example, for containers having very large height dimensions, or for containers of higher volumes, in order to provide greater volumes of gas, without increasing the gas inlet pressure or the gas bubble volume. Additional gas inlet ports 28 can be located at any location on the surface of container 12, and are preferably located within the bottom one half of the height of container 12, to provide substantial mixing and aeration of the medium. Such a configuration, having a plurality of gas inlet ports is indicated here by gas inlet ports at positions I [28(I)] and II [28(II)], having gas inlets 34(I) and 34 (II), respectively, positioned at a distance from each other, to provide efficient mixing and aeration of the plant cell culture. Gas inlet ports can further contain a contamination prevention mechanism, such as a filter 49 or a trap (not shown), which can prevent entry of contaminating gas, fluids or solids (e.g. airborne microbes) into the inner volume of container 12 and the culture medium.

Container 12 includes gas exhaust port 30 for venting and removal of gas accumulating above the culture medium. Gas exhaust port 30 is located in the upper one half preferably upper one third portion of container 12, at a location substantially above the level of fluid (e.g. culture medium) so as to be in fluid communication with the "headspace" above the culture medium. External gas exhaust opening 46 of gas exhaust port 30 can open to the environment, and the flow of exhaust gas is unregulated at gas exhaust port 30. Optionally, and alternatively, gas exhaust port 30 can further include a gas exhaust regulator 48 (e.g. pressure valve or clamp) which regulates the flow of gas out of container 12, and thus can be used to create a positive gas pressure within container 12 and thus maintain container 12 amply inflated and in the desired cylindrical shape. Gas exhaust port 30 can further include a contamination prevention mechanism, such a filter 49 or a trap, which can prevent entry of contaminating gas, fluids or solids (e.g. airborne microbes) into the inner volume of container 12 and the culture medium.

Since container 12 of the present invention is designed for use with volumes of at least 400 and up to several thousand liters of culture medium, and since it is flexible in nature, device 10 further includes a support structure for supporting container 12 in position.

Figure 2:
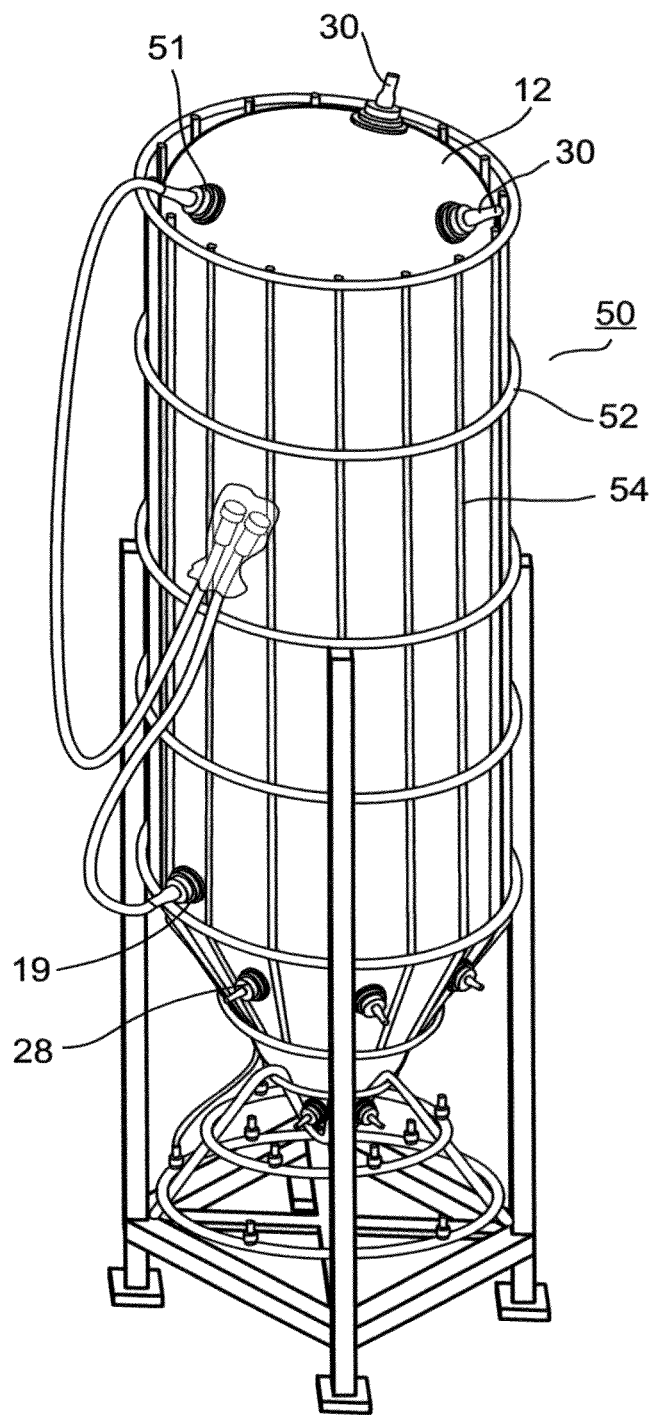

As is shown in FIG. 2, support 50 can include a conical structure which is designed to provide support for container 12 without exerting force on container 12 or the contents therein.

Support 50 can be fabricated from steel, wood, plastic or ceramic. The support can be made of lightweight cylindrical or elliptical tubing forming a grid like structure of ring shaped 52 and rod like 54 support members. Alternatively, the support members can be plates, connected to vertical rod-like members and further connected to horizontal, ring-shaped members. The plates can be continuous, essentially creating a shell-like support for the container, or can be stave-like, providing rings of broad support elements with space between them. Support structure 50 can be free standing, or attached to casters (not shown) for mobility, or it can be further supported by attachment to a rigid structure such as a wall, floor, column, etc.

Container 12 is disposable and thus is designed to be discarded following use (one or more culturing cycles) with minimal loss and impact to the environment. Devices made from plastics such as the flexible plastics used in the present device, for example, are relatively inexpensive and can therefore be disposed of after use with negligible economic loss, if so desired. Disposal of these bioreactor devices does not generally present an economic disadvantage to the user, since even the low capital costs of these items is offset against ease of use, storage and other practical considerations. Disposal is advantageous in that it eliminates the need for extensive washings with disinfectants and other harsh chemicals which can contaminate the environment. Thus, polymeric disposable bioreactor devices such as container 12 can be easily recycled, thus reducing pollution and environmental impact of their use.

Although container 12 can be sterilized and reused, it is preferably provided in a pre-sterilized form, thereby eliminating the need for costly and time consuming sterilization procedures. Sterilization of the non-rigid container can be performed using wet and/or dry sterilization processes. Preferably, the sterilization is a dry sterilization process suited for use with flexible, non-rigid plastic materials mentioned herein, such as gamma or electron beam radiation, gas (e.g. ethylene oxide) sterilization, and the like, well known in the art.

According to preferred embodiments of the present invention, the operation of the previously described individual device and/or battery is controlled by a computer (not shown). The computer is optionally and preferably able to control such parameters of the operation of the battery and/or of a device according to the present invention as one or more of temperature, amount and timing of gas or gas combination entering the container, amount and timing of gas being allowed to exit the container, amount and timing of the addition of at least one material (such as nutrients, culture medium and so forth), and/or amount of light. The computer may optionally also be able to detect the amount of waste being produced.

The computer is preferably connected to the various measuring instruments present with regard to the operation of the present invention, as an example of a system for automating or semi-automating the operation of the present invention. For example, the computer is preferably connected to a gauge (not shown) or gauges for controlling the flow of a gas or gas combination. The gauge is preferably connected to a pipe connectable to a suitable air supply, and controls the flow of air or other gas(es) to the pipe.

The computer is also preferably connected to a temperature gauge, which is more preferably present in the environment of container 12 but more preferably not within container 12. The computer is also optionally and preferably able to control a mechanism for controlling the temperature, such as a heater and/or cooler for example.

The computer is optionally and preferably connected to a gauge for controlling the flow of media and/or other nutrients from a nutrient/media container to container 12.

The computer is preferably connected to at least one port of the container, and more preferably is connected at least to harvest port 19. The computer optionally may control an automated sampler and/or harvester for removing portions of the contents of the container from an optional sampling port, for testing and/or harvesting (not shown). The computer may also optionally be connected to an analyzer for analyzing these portions of contents, for example in order to provide feedback for operation of the computer.

As is mentioned hereinabove, device 10 is designed for culturing plant cell cultures. Culture media suitable for large volume culture of plant cells in the device of the present invention can be any plant cell culture medium known in the art. Specific, but non-limiting examples of suitable culture media are Murashige and Skoog media (Sigma Ltd, St Louis, Mo.), Anderson medium, Schenk and Hildebrandt medium and the like. Many plant tissue culture media are commercially available (see, for example, Phytotechnology Laboratories, Shawnee Mission, Ky.).

The phrase "plant cell culture" refers to any type of wild type (naturally occurring) plant cells or genetically modified plant cells (e.g., capable of stable or transient expression of exogenous genes). Preferably, it refers to cultures of cells that produce an active ingredient which is commercially desired for use in the pharmaceutical industry (drug or drug APIs), food industry (e.g., flavor, aroma), agriculture (e.g., pesticide), cosmetics and the like.

Preferably, the plant cell culture comprises plant cells obtained from a plant tissue such as root or leaf meristem. More preferably, the plant cells are selected from the group consisting of *Agrobacterium rihzogenes* transformed root cell, celery cell, ginger cell, tobacco, alfalfa, tomato, lettuce, horseradish cell and carrot cell.

Additional cell cultures that can be grown in the present invention include yeast, moss, algae, photosynthesizing bacteria.

Plant cell cultures suitable for use with the devices and methods of the present invention include, but are not limited to, established cell lines and cell lines generated from plant roots, leaves, stem, flowers and the like. Non-limiting examples of established cell lines are *Nicotiana tabacum* L. cv Bright Yellow-2 (BY-2) and *Nicotiana tabacum* L. cv. Petit Havana cell lines.

It will be appreciated that the increased gas inlet pressure, the increased gas inlet density, the increased gas aeration rate and volume required to provide mixing and aeration suitable for Large Scale Bioreactors of the present invention, can present a possible problem of foaming of the plant cell medium, which can be detrimental to cells and the contents of the medium. Methods known in the art for inhibition of foaming include, but are not limited to, the use of antifoam agents such as silicones, organic phosphates and alcohols, which act to cause small bubbles to coalesce into larger, less detrimental bubbles. Food grade antifoam agents commonly used in industry and food processing include, for example, polydimethylsiloxane and Simethicone. The use of antifoaming agent in the Large Scale Disposable Bioreactor of the present invention is described in detail in the Examples section hereinbelow.

The present invention also relates to a method for culturing and harvesting plant cells in a Large Scale Disposable Bioreactor. The device is optionally and preferably configured according to the device described hereinabove, most preferably according to the device described in Example 1 below. In this method, plant cells are preferably placed in a container of the device according to the present invention. Optionally and more preferably, the plant cells are cultured in suspension.

According to preferred embodiments of the present invention, the plant cells are cultured in suspension in a liquid medium, with at least one sterile gas or gas combination (plurality of gases) added as required. Optionally and preferably, the sterile gas comprises a sterile gas combination which more preferably comprises sterile air. The sterile gas and/or gas combination is preferably added to the container through an air inlet, preferably connected to a sterilizing filter (preferably, a 0.2 micron filter) during each cycle, either continuously or in pulses, as previously described.

Sterile culture medium and/or sterile additives are preferably placed in the container and transferred through additive inlet 51 into the bioreactor, preferably through sterilization filter or filters as previously described.

The plant cells (as an example of an axenic inoculant) are optionally and preferably added through the harvester. Optionally and preferably, the plant cells in the container (12) can be exposed to light, for example through an external light (a source of illumination external to the container), particularly if the container is transparent and/or translucent. Optionally, no light source is used, optionally the container is maintained in dark conditions.

The cells are allowed to grow to a desired yield of cells and/or the material produced by the cells, such as a protein or secondary metabolite for example.

According to preferred embodiments, excess air and/or waste gases are preferably allowed to leave the container through a gas outlet, optionally through a filter, optionally and more preferably continuously and/or intermittently.

Also optionally and preferably, the material in the container (such as the cell culture medium for example) is checked for one or more contaminants and/or the quality of the cells and/or cell product(s) which are produced in the container. More preferably if one or more contaminants are found to be present in the culture, or the cells and/or cell product(s) which are produced are of poor quality, the device and its contents are disposed of.

At an appropriate time, particularly if contaminant(s) and/or poor quality cells and/or cell product(s) are not found, at least a first portion of the material in the container is preferably harvested, such as medium containing cells and/or cell product(s). More preferably, a remaining second portion of material, such as medium containing cells and/or cell product(s) is allowed to remain in the container, wherein this second portion may optionally serve as an inoculant for a next culture/harvest cycle. Next, sterile culture medium and/or sterile additives can be provided for the next culture/harvest cycle through an additive inlet 51, optionally connected to a filter 49 for prevention of contamination.

The previously described cycle is optionally performed more than once. Optionally and preferably, the method permits cells to be cultured and/or harvested anaerobically.

For the anaerobic embodiment, inert gas, instead of oxygen or air, is provided through the gas inlets of the device. For at least one device thereof the following process is performed. An axenic inoculant is introduced to device via a harvesting port. Next, sterile culture medium and/or sterile additives is added to the device via common additive inlet piping. Optionally, the device is illuminated as previously described.

The cells in the device are allowed to grow in medium to a desired yield of cells and/or product(s) of the cells. Optionally and preferably, excess air and/or waste gases are permitted to leave the device, optionally through a filter, more preferably continuously, via gas exhaust port.

As for the previous method, the material in the container is monitored for the presence of one or more contaminant(s) and/or poor quality cells and/or poor quality cell product(s), in which case the container and its contents are preferably disposed of. Also as for the previous method, the cells and/or cell product(s) are preferably harvested at a suitable time, for example when a desired amount of cell product(s) has been produced.

Typically, a water purification system supplies deionized and substantially endotoxin free water to a tank comprising concentrated media, and diluted media is then pumped to the device 10 via an additive inlet. Filters, typically 0.2 micrometer, are installed in the feed pipes and also just upstream of the inlet to minimize risk of contamination of the container contents in each device 10. Alternatively or additionally, a valve may be also be used to minimize this risk.

For the first culturing cycle of each device 10, inoculant, typically a sufficient sample of the type of cell that it is required to harvest in the device 10, is premixed with media or water in a pre-sterilized container and is introduced into the device 10, typically via the harvester port, but alternatively or optionally via a separate additive inlet port. Media is then introduced into the device 10 via the harvester port, or via the optional additive inlet port. For subsequent cycles, only media and/or additives are introduced, as hereinbefore described.

Typically, an air compressor provides substantially sterilized air or gasses to each device 10, via a number of apparatuses: a coarse filter for removing particles, a dryer and humidity apparatus for removing humidity, and a fine filter, typically 0.2 micro-meter, for removing contaminants. Preferably, another filter just upstream of the gas inlet further minimizes the risk of contamination of the container contents.

For each device 10, all connections to the container 12, i.e., to gas inlet port(s), to additive inlet port, and preferably also to the gas exhaust port(s) and to the harvester are sterilized prior to use, and sterility is maintained during connection to peripheral equipment, including, for example, air supply and exhaust by performing the connections in the laminar airflow hood.

Temperature control for each device 10 is preferably provided by a suitable air handling unit. Optional illumination of the device may be provided by suitable fluorescent lights suitably arranged around the device 10, when required for cell growth or compound production.

During each culturing cycle of each device 10, the contents of each corresponding container 12 are typically aerated and mixed for about 3 to about 14 days, or longer, under controlled temperature and lighting conditions. Culture conditions and duration of culture are determined according to individual requirements of each culture cycle, such as type of cell cultured, recombinant product to be harvested, concentration of inoculant, and the like.

At the end of the culturing cycle for each device 10, the corresponding harvester port is typically connected to a presterilized environment with suitable connectors which are sterilized prior and during connection, as hereinbefore described. Harvesting is then effected, leaving behind between about 2.5% to about 45%, though typically between about 10% to about 35%, of cells and/or tissue to serve as inoculant for the next cycle.

The harvested cells/tissues and/or cell product(s) may then optionally be dried, or extracted, as required.

Another optional adjustment is the addition of pure oxygen during the cell culture process, more preferably on day 3 or 4 after starting the culture process.

An example of a preferred cell type suitable for culturing in the Large Scale Disposable Bioreactor of the invention is the transformed carrot cell described in the Examples section which follows. As described in the Examples section, this cell is an *Agrobacterium tumefaciens*-transformed carrot cell which expresses an exogenous gene encoding human glucocerebrosidase (hGCD). IN another embodiment of one aspect of the invention, the cell type is *Nicotiana tabacum*. In yet another embodiment of the invention, the *Nicotiana tabacum* cells are BY-2 cells. Methods for transformation and expression of exogenous genes in carrot and other cell types, suitable for use with the Large Scale Disposable Bioreactors of the present invention, are well known in the art. Transformation and expression of biologically active exogenous proteins in carrot and other cell cultures, using disposable bioreactors, is disclosed in detail in U.S. patent application Ser. No. 10/784,295 and PCT publication WO 2004/096978, which are incorporated fully herein.

The Examples section which follows demonstrates use of the present device in culturing the above described carrot cell, and in tobacco *Nicotiana tabaccum* cells. As is shown therein, culture of transgenic carrot and tobacco cells in a Large Scale Bioreactor device 10, having a volume of greater than 400 liters, resulted in superior yield and purity of the recombinant protein. Carrot cells expressing human Glucocerebrosidase and tobacco cells expressing Aceteylcholineesterase-R were cultured in the Large Scale and smaller scale disposable Bioreactors, and the culture conditions, yields and product analyzed and compared (see Examples 2 and 3). The results show that the Large Scale Disposable Bioreactor of the present invention provides increased $O_2$ saturation of the culture medium, at a significantly lower inlet aeration rate, up to 30% for at least 7 days of culture, and greater efficiency of culture, resulting in higher yield of the recombinant protein product. Analysis of the recombinant protein by peptide mapping (FIG. 8), IEF (FIG. 10), SDS-PAGE and immunological analysis (FIGS. 7 and 15-17), and chromatography (FIGS. 6 and 9) showed that the glucocerebrosidase and acetylcholinesterase enzyme preparations from cells harvested from the Large Scale Disposable Bioreactor are identical with that of a standard preparation obtained with standard-scale technology, strongly indicating the consistency and identity of the enzyme preparations produced from cells harvested from the 80 L, 400 L and 800 L bioreactors. Enzyme preparations from the Large Scale Disposable Bioreactor also showed comparable, if not superior, catalytic activity and specific activity (see Table 5 and FIG. 17). Further, it was shown that recombinant (β-glucocerebrosidase produced in Large Scale Disposable Bioreactors of the present invention contain undetectable levels of carrot host cell proteins, no less pure than the β-glucocerebrosidase manufactured by the standard volume production methods (FIG. 11). Thus, the Large Scale Disposable Bioreactor of the present invention can provide accurate, efficient and even superior conditions for scale-up of plant cell cultures expressing recombinant proteins developed in smaller, even much smaller, volumes.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Efficient Culturing of Plant Cells in a Large Scale Disposable Bioreactor

In order to test the growth parameters, yields and characteristics of the cultures and cell products produced using the Large Scale Disposable Bioreactor, carrot cells expressing Human Glucocerebrosidase were cultured in the Large Scale and smaller scale disposable Bioreactors, and the culture conditions, yields and product analyzed and compared.

Materials and Experimental Methods:

Transformation and Culturing of Carrot Cells Expressing GCD:

Cell transformation and culturing were effected as described in Example 2

Upscale Culture Growth in a Bioreactor

About 1 cm (in diameter) of genetically modified carrot cell callus, containing the rh-GCD gene, was plated onto an agar medium in a 9 cm plate containing 4.4 gr/l MSD medium (Duchefa, Haarlem, The Netherlands), 9.9 mg/l thiamin HCl (Duchefa), 0.5 mg folic acid (Sigma Ltd, St Louis, Mo.) 0.5 mg/l biotin (Duchefa), 0.8 g/l Casein hydrolisate (Duchefa), sugar 30 g/l and hormones 2-4 D (Sigma). The callus was grown for 14 days at 25° C.

Cell suspension culture was prepared by sub-culturing the transformed callus in MSD liquid medium containing 0.2 mg/l 2,4-dichloroacetic acid), as is well known in the art. The cell suspension culture was then cultured in a 250 ml Erlenmeyer flask, beginning with a 25 ml working volume and increasing the volume to 50 ml following 7 days of culture, at 25° C. with shaking speed of 60 rpm. Subsequently, cell culture volume was increased up to 300 ml in a 1 L Erlenmeyer under the same conditions.

Inoculum of the small bio-reactor (10 L) [see WO98/13469] containing 4 L MSD medium, was effected by adding 400 ml of cell suspensions derived from two 1 L Erlenmeyers that were cultured for seven days. Following a week of cultivation at 25° C. with 1 Lpm airflow, MDS medium was added up to 10 L and the cultivation continued under the same conditions. After additional cultivation (five days), most of the cells were harvested and collected by passing the cell media through a 80 micron net. The extra medium was squeezed out and the packed cell cake was stored at −70° C.

Antifoam:

To avoid foaming, Medicinal Antifoam C Emulsion (Polydimethylsiloxane-PDMS, Dow Corning, Midland Mich.) was used, containing 30% Simethicone USP, Methylcellulose, sorbic acid and water. The antifoam was added to the 400 L bioreactor media at a concentration of 10 ppm.

Antifoam Analysis:

Antifoam C Emulsion (PDMS) is used as an anti-flatulent and an ingredient in non-standardized foods. PDMS presence was evaluated according to and in compliance with all USP requirements for Simethicone emulsions. A 450 ml solution of 0.075 PDMS was loaded onto a 15 ml cation exchange chromatography column (Macro-Prep® High S Support, BioRad, Hercules, Calif.). Aliquots for PDMS analysis were taken from the load, flow through (unbound materials) and from three elution steps of 0.2 M NaCl, 1.2 M NaCl and 12% Ethanol in 1.2 M NaCl.

Aliquot samples of the harvested culture during the different chromatography steps (load, flow through, wash and elution steps) were collected and analyzed for PDMS presence using an RP-HPLC method, with a C4 column monitored at 262 nm, (peak absorbance of the Antifoam C Emulsion).

SDS-PAGE:

Sodium Dodecyl Sulfate-Polyacrylamide Gel Electrophoresis (SDS-PAGE) separates proteins primarily by their molecular weight. In addition, this technique provides large amounts of information about the purity and composition of proteins. The molecular weight identity and the protein impurity pattern of prGCD produced from cells harvested from the Large Scale Disposable Bioreactor were examined by SDS-PAGE analysis using Coomassie Brilliant blue staining, according to standard gel separation protocols. Briefly, the SDS gels consist of a stacking gel (3%) and a resolving gel (12%). Running buffer was Tris/SDS, pH 8.3, loading buffer was glycerol-Tris-mercaptoethanol, pH 6.8.

Reverse Phase High Performance (Pressure) Liquid Chromatography (RP-HPLC):

RP-HPLC comprises the separation of intact protein and other components from a protein solution. The exact retention time of each compound is characteristic and allows determination of the identity and purity of the protein of interest. The characteristic peak and retention time of the plant recombinant GCD (prGCD) was determined using a column of stationary phase C-4 (Phenomenex Jupiter 5 u C4 proteo 300 A 4.6×250 mm Phenomenex, Torance Calif.) with a mobile phase gradient of: A; 0.1% TFA/$H_2O$ and B; 0.1% TFA/Acetonitril. Protein detection was with diode-array spectrophotometer detecting at two wavelengths: 214 nm and 280 nm.

Preparation of Polyclonal Antibodies:

Recombinant GCD (75 micrograms, Cerezyme™ Genzyme, Cambridge, Mass.) was suspended in 3 ml complete Freund's adjuvant (Difco, Voigt, Lawrence, Kans.) and injected to each of two rabbits, followed by a booster injection after two weeks. The rabbits were bled about 10 days after the booster injection and again at one week intervals until the antibody titer began to drop. After removal of the clot the serum was divided into aliquots and stored at −20° C.

Western Blotting:

Western blot was performed to identify the plant recombinant GCD (prGCD) molecules purified from cells harvested from the Large Scale Disposable Bioreactor in comparison to previously manufactured batches and to commercial human β-glucocerebrosidase (Cerezyme®, Genzyme, Cambridge, Mass.) by using specific affinity purified anti-GCD antibodies. Protein transfer was performed substantially as described herein. Briefly, transfer from the gel to nitrocellulose was performed at 100 volts for 90 minutes at 4° C. After the transfer, the membranes were incubated in blocking buffer [1% dry milk, 0.1% Tween 20 (Cat. No: P1379; Sigma Ltd, St Louis, Mo.) in phosphate buffer]. Proteins were then immuno detected by incubation with anti-GCD antibody, washed, and reacted with a suitable secondary antibody (such as Goat anti rabbit (whole molecule) HRP (Cat. No. A-4914). Blots were then developed with ECL developer reagents (RPN 2209, Amersham, Pharmacia Biotech UK LTD), and autoradiography used for visualization.

Comparison Between prGCD Production in Different Bioreactors and Different Aeration Regimes:

Recombinant cells expressing prGCD were grown in different volume bioreators (10 L, 100 L, 400 L) for 4-7 days. Cells were grown in three different 10 L bioreactors, subjected to different aeration regimes (with sparger; with an 8 mm bore opening; with 100% oxygen added from day 4). Samples of crude extracts (5 μl) were taken at day 4 or day 7, separated on PAGE, blotted onto a nitrocellulose transfer membrane, together with 25 ng of prGCD standard, and reacted with specific rabbit anti-GCD polyclonal antibody. Bands were visualized by SuperSignal West Pico Chemiluminescent Substrate (Pierce Biotechnology, Rockford, Ill.).

Dissolved Oxygen:

Dissolved oxygen rates are depicted in Kla units: $dC/dT=Kla,(Cs-C)$, where Cs is the saturation level of oxygen, in mg/l and C is the actual oxygen concentration, in mg/l Aeration Rate:

Aeration rate is defined as the volume of air at 1 Atm pressure per volume of liquid volume per minute (volume per volume per minute-) at the gas inlet was calculated by deviding the inlet air flow by the working volume of the bioreactor.

Determining Optimal Aeration Rate:

In order to determine optimal aeration rates, optimization was effected for every increase in volume (from 100 L, to the Large Scale bioreactors of 400 and 800 L), by upscaling the air flow to achieve aeration rate of the lower volume bioreator, and altering aeration rate until achieving optimal predetermined parameters. The effect of different aeration rates was tested on physical parameters including foaming level, liquid turbulence level, filter resistance to air outflow and expandment of bioreactor. Biological parameters included cultured cell growth curve as depicted by daily recordation of cellular fresh weight (gr/L) for a growth cycle (7 days) and protein product yields at 7 days. 10-15 growth cycles were compared for achieving optimized aeration rate.

Results

Large Scale Disposable Bioreactors Culturing Requires Lower Aeration Rates:

It is an axiom of cell culture that increased aeration increases the rate of growth of cells in culture. Smaller volume bioreactors for plant cell culture typically provide air at an aeration rate of 0.15-0.3 vvm. Surprisingly, when culture efficiency of bioreactors of various volumes was evaluated over a range of aeration rates suitable for promoting air circulation and oxygen distribution, while maintaining a minimal shear force, it was found that optimal aeration rates for Large Scale Bioreactors were proportionally lower than those for smaller volume reactors. Table 1 below illustrates that while in lower volume bioreactors (up to 100 L) an increase in volume requires an increase in aeration rates to maintain efficiency, in Large Scale Bioreactors (400 L and greater), optimal aeration rates actually decrease with increasing bioreactor volume. Such a decrease is advantageous in industrial scale culturing for both the ability to decrease shear forces, and the greater energy efficiency.

TABLE 1

Optimized aeration rate in bioreactors of different volumes

| Bioreactor model | Working volume (L) | Inlet air flow (liter/minute) | Aeration rate (VVM) |
|---|---|---|---|
| PX10 | 10 | 1.5 | 0.15 |
| PX100 | 85 | 15 | 0.18 |
| PX400 | 350 | 35 | 0.10 |
| PX800 | 700 | 65 | 0.09 |

Large Scale Disposable Bioreactor Provides Superior Oxygen Saturation Levels:

Proper combinations of the parameters effecting the introduction, mixing and venting of gas in the bioreactor are crucial to the efficient operation of the Large Scale Disposable Bioreactor of the present invention. Bubble volume, aeration rate, gas pressure at inlet, gas pressure in the bubbles and the path of the bubble through the culture medium must be balanced to optimize aeration and mixing, yet minimize destructive shear forces and turbulence within the suspension. In order to assess these parameters, oxygen saturation levels were determined.

FIG. 3 shows the percent $O_2$ saturation of the medium in a 400 liter Large Scale Disposable Bioreactor, compared with $O_2$ saturation in the medium using smaller reactor vessels (Erlenmeyer flask 10 liter bioreactor and 100 liter bioreactor), measured in aliquots sampled at time of inoculation (day 0), and at 3, 4 and 7 days of culture. Air pressure and flow was 35 L/min in the Large Scale Bioreactor, and 10 L/min in the smaller 10 and 100 liter reactors. The reduction in saturation after inoculation, as the cell content of the suspension increases in proportion, is a well known phenomenon. Yet, despite the gradual reduction over 7 days, the Large Scale Disposable Bioreactor clearly provides conditions for superior $O_2$ saturation of the medium, exceeding 30% at any given time up to 7 days post inoculum.

Table 2 below illustrates that the 800 liter bioreactor attains an even greater $O_2$ saturation levels, expressed as Kla (mg/L) as compared with a bioreactor of smaller volume. This superiority is maintained throughout a range of aeration rates.

TABLE 2

Concentration of dissolved oxygen (Kla in mg/L), at different aeration rates (vvm)-comparison between 400 and 800 L Large Scale disposable bioreactors.

| Bioreactor | 0.07 vvm | 0.1 vvm | 0.11 vvm |
|---|---|---|---|
| PX400 | 3.24 | 4.68 | 7.56 |
| PX800 | 4.68 | 7.92 | 10.08 |

Large Scale Disposable Bioreactor Provides Superior Recombinant Protein Yields:

In order to determine the effect of culturing in the Large Scale Disposable Bioreactor on the efficiency of production of recombinant protein in the culture, extracts of suspension from each of the reactors were separated by SDS-PAGE, blotted and analyzed by immune detection with anti-human glucocerebrosidase (GCD) antibody. Comparison between the yield of recombinant product in the 400 L Large Scale Disposable Bioreactor (FIG. 4, lanes 4-6), and those of the 10 L (FIG. 4, lanes 1-3) and 100 L (FIG. 4, lanes 7 and 8) reactors clearly shows the increased protein levels, and more efficient use of the medium in the Large Scale Bioreactor. Indeed, the yield of GCD in the Large Scale Bioreactor at 4 and 7 days culture (lanes 4, 5 and 6, respectively) was superior to that of the 10 L reactor with increased gas inlet bore (FIG. 4, lane 2) and addition of $O_2$ from day 4 (FIG. 4, lane 3).

These results indicate that the Large Scale Disposable Bioreactor of the present invention provides increased $O_2$ saturation of the culture medium, and greater efficiency of culture, resulting in higher yield of the recombinant protein product and greater energy efficiency.

Efficient and Simple Removal of Antifoam from Culture Medium in Large Scale Disposable Bioreactor:

In the use of higher air pressures for aeration of the Large Scale Disposable Bioreactor, the issue of foaming of the medium, which should be avoided for many reasons, requires attention. Antifoam (10 ppm) was added to the cell growth media when transferred to the 400 L bioreactor.—
The lowest level of detection using standardized laboratory techniques such as HPLC and atomic absorption is approximately 7 ppm.

In order to confirm that the harvesting and purification of recombinant product from the Large Scale Disposable Bioreactor is capable of eliminating antifoam residue, large excess of PDMS antifoam were subjected to the initial steps of the purification process, and the presence of antifoam monitored throughout.

FIG. 5a is an RP-HPLC analysis of the PDMS antifoam (0.075%) in an aliquot of the load solution of the cation exchange column Retention time (peak) was 22.531 minutes. FIG. 5b shows the antifoam in the flow through of the column (retention time 22.554 minutes), with size of peak and absorbance at 262 nm similar to the loaded material. No PDMS was detected in samples from any of the three subsequent elution steps (0.2M NaCl, 1.2M NaCl, and 12% ethanol in 1.2M NaCl). Table 3 below clearly indicates that the PDMS was not retained on the column:

TABLE 3

Summary of the performance and yield of PDMS on cation exchange chromatography column

| Sample | Sample Volume (ml) | Absorbent (OD/ml) | Total OD | Yield Absorbent (%) | HPLC peak area | Yield by HPLC (%) |
|---|---|---|---|---|---|---|
| Load | 450 | 0.097 | 43.65 | 100 | 438.46 | 100 |
| Flow through | 448 | 0.101 | 45.24 | 103 | 443.00 | 101 |

These results clearly indicate that antifoam residue is easily removed from the medium, and remains below detectable levels from the first stages of the isolation and purification process.

Example 2

Efficient Expression of Human Glucocerebrosidase in Carrot Cell Suspension Using Large-Scale Disposable Bioreactor This Example provides a description of experiments that were performed with transformed plant cells, cultured in the Large Scale Disposable Bioreactor of the present invention, according to some embodiments of the present invention.

Materials and Experimental Methods

Plasmid Vectors:

*CE-T—was constructed from plasmid CE obtained from Prof. Galili [U.S. Pat. No. 5,367,110 Nov. 22, (1994)].

Plasmid CE was digested with SalI. The SalI cohesive end was made blunt-ended using the large fragment of DNA polymerase I. Then the plasmid was digested with PstI and ligated to a DNA fragment coding for the ER targeting signal from the basic endochitinase gene [*Arabidopsis thaliana*] ATGAAGACTAATCTTTTTCTCTTTCT-CATCTTTTCACTTCTCCTATCATTATCCTC GGC-CGAATTC (SEQ ID NO: 6), and vacuolar targeting signal from Tobacco chitinase A: GATCTTTTAGTCGATAC-TATG (SEQ ID NO: 5) digested with SmaI and PstI.

*pGREENII—obtained from Dr. P. Mullineaux [Roger P. Hellens et al., (2000) Plant Mol. Bio. 42:819-832]. Expression from the pGREEN II vector is controlled by the 35S promoter from Cauliflower Mosaic Virus, the TMV (Tobacco Mosaic Virus) omega translational enhancer element and the octopine synthase terminator sequence from *Agrobacterium tumefaciens*.

Human Glucocerebrosidase (hGCD) cDNA:

human glucorebrosidase was obtained from ATCC (Accession No. 65696), GC-2.2 [GCS-2 kb; lambda-EZZ-gamma3 *Homo sapiens*] containing glucosidase beta acid [glucocerebrosidase]. Insert lengths (kb): 2.20; Tissue: fibroblast WI-38 cell.

Construction of hGCD Expression Plasmid:

The cDNA coding for hGCD (ATTC clone number 65696) was amplified using the forward: 5' CA GAATTCGCCCGCCCCTGCA 3' (SEQ ID NO: 3) and the reverse: 5' CTCAGATCTTGGCGATGCCACA 3' (SEQ ID NO: 4) primers. The purified PCR DNA product was digested with endonucleases EcoRI and BglII (see recognition sequences underlined in the primers) and ligated into an intermediate vector having an expression cassette CE-T digested with the same enzymes. The expression cassette was cut and eluted from the intermediate vector and ligated into the binary vector pGREENII using restriction enzymes SmaI and XbaI, forming the final expression vector. Kanamycin resistance is conferred by the NPTII gene driven by the nos promoter obtained together with the pGREEN vector, to provide an expression cassette.

The resulting plasmid was sequenced to ensure correct in-frame fusion of the signals using the following sequencing primers: 5' 35S promoter: 5' CTCAGAAGACCA-GAGGGC 3'(SEQ ID NO: 1), and the 3' terminator: 5' CAAAGCGGCCATCGTGC 3' (SEQ ID NO: 2).

Establishment of Carrot Callus and Cell Suspension Cultures:

Establishment of carrot callus and cell suspension cultures we preformed as described previously by Torres K. C. (Tissue culture techniques for horticular crops, p.p. 111, 169).

Transformation of Carrot Cells and Isolation of Transformed Cells:

Transformation of carrot cells was effected by *Agrobacterium* infiltration, using an adaptation of a method described previously [Wurtele, E. S. and Bulka, K. Plant Sci. 61:253-262 (1989)]. Cells growing in liquid media were used throughout the process instead of calli. Incubation and growth times were adapted for transformation of cells in liquid culture. Briefly, *Agrobacteria* were transformed with the pGREEN II vector by electroporation [den Dulk-Ra, A. and Hooykaas, P. J. Methods Mol. Biol. 55:63-72 (1995)] and then selected using Kanamycin. Carrot cells were thereafter transformed with *Agrobacteria* and selected using paromomycine antibiotics in liquid media.

Screening of Transformed Carrot Cells for Isolation of Calli Expressing High Levels of GCD:

Cells were homogenized in SDS sample buffer and the resulting protein extracts were separated on SDS-PAGE [Laemmli U., (1970) Nature 227:680-685] and transferred to nitrocellulose membrane (hybond C nitrocellulose, 0.45 micron. Cat. No: RPN203C; Amersham, Pharmacia Biotech UK LTD). Western blot for detection of GCD was performed using polyclonal anti hGCD antibodies (described herein below).

Culturing and Scale Up of Cells in the Large Scale Bioreactors:

culturing of cells was effected as described in detail in Example 1 herinabove.

Protein Analysis:

Analysis of protein identity and purity was effected as described in Example 1 hereinabove.

Mass Spectrometry:

Mass-Spectrometry (MS) analysis was performed using a matrix-assisted laser desorption ionization time-of-flight/time-of-flight (MALDI-TOF) Mass spectrometer (4700, Applied Biosystems, Foster City Calif.) and an ion-trap mass spectrometer (LCQ classic, Finnigan, San Jose, Calif.).

Peptide Mapping or Protein "Fingerprinting" Using RP-HPLC:

Peptide mapping is a method for analyzing peptides resulting from proteolytic digestion of a protein followed by RP-HPLC to provide high-resolution separating that is reproducible with a distinct profile called "Fingerprinting". As a highly specific identification method, this analysis serves to confirm the identity of the enzyme preparation produced in the standard production process and from cells harvested from the 400 L bioreactor (PX-400-GC-2; within the limits of the technique). prGCD was digested with Trypsin by incubating at 1:50 w/w with Trypsin in 50 mM $(NH_4)_2CO_3$ (pH 8.0) for 6 hours at 37° C. followed by over-night incubation at room temperature.

For RP-HPLC analysis, 50 µg of digested peptide was loaded on the C-18 column, (Column: Phenomenex Jupiter 4 u proteo 90 A 4.6×250 mm, Phenomenex, Torance Calif.) and the peptides were separated, and detected as described hereinabove.

IEF:

Isoelectric Focusing (IEF) is a technique that separates proteins on the basis of their charge in an electrical field. IEF is employed as an identification tool, and to ensure the homogeneity of a protein as demonstrated by a pattern with the correct pI range. Isoelectric focusing of the prGCD, and Cerezyme® was carried out according to standard protocol. Briefly, to identify the isoelectric point (pI) of prGCD the purified enzyme was run on pre-cast polyacrylamide IEF gel with pH range 3-10 (Bio-Rad Laboratories, Hercules Calif.) using designated anode and cathode buffers and pI standards (Amersham Pharmacia Biotech UK LTD). To each prGCD and Cerezyme® sample, 0.05% taurocholic acid (slight anionic detergent) was added to improve the mobility in the gel.

The banding pattern of prGCD and Cerezyme® proteins were visualized by Bio-Safe™ Coomassie Stain (Bio-Rad Laboratories, Hercules Calif.) as directed by the manufacturer. The pI of each protein band was estimated by using the protein standards of the IEF Calibration Kit High Rang pI 5-10.5 (Amersham Pharmacia Biotech UK LTD). Similarity banding profile of the prGCD and commercially produced Cerezyme® was determined. The prGCD banding pattern was also examined for batch-to-batch consistency.

Enzymatic Activity Assay:

β-Glucocerebrosidase catalyzes the hydrolysis of the glycolipid glucocerebroside to glucose and ceramide. To assess the catalytic activity of the recombinant glucocerebrosidase, an enzymatic assay using a synthetic substrate is employed for evaluation of each batch. An enzyme unit is defined as the amount of enzyme that catalyzes the hydrolysis of one micromole of the synthetic substrate para-nitrophenyl-β-D-glucopyranoside (pNP-Glc) per minute at 37° C.

Results

Characterization of Recombinant Glucocerebrosidase from Large Scale Disposable Bioreactor:

In order to determine the optimal character of the improved culture conditions afforded by the Large Scale Disposable Bioreactor, and in order to test the reliability and reproducibility of these conditions, the molecular and physico-chemical characteristics of the recombinant product, produced in Large Scale Disposable Bioreactors, was compared with preparations produced in smaller scale bioreactors.

Molecular Weight of Glucocerebrosidase Determined by Mass Spectrometry:

Mass spectrometry analysis was effected to determine the mass of the protein without the need for protein standards. Two mass spectrometry methods were used to determine the molecular weight of the enzyme produced from cells harvested from the 400 L bioreactor, and this was compared to the Glucocerebrosidase produced in smaller scale reactors. All enzyme preparations were isolated and purified in the same manner.

Table 4 below summarizes the molecular weight of several enzyme batches obtained by both instruments, LCQ classic and MALDI-TOF. Batches of prGCD produced from cells harvested from the 400 L bioreactor are indicated by PX400-GC.

TABLE 4

Molecular Weight of Different prGCD produced from different Batches

| Bioreactor | Enzyme Batch No. | Molecular Weight (D) (LCQ classic) | Molecular Weight (D) MALDI-TOF |
|---|---|---|---|
| 80L | PLX-GC-016-0505-DS | 60877 | 60954 |
| 80L | PLX-GC-016-Phenyl | 60884 | 60923 |
| 80L | PLX-GC-017-0705-DS | 60865 | 60524 |
| 80L | PLX-GC-017-Phenyl | 60869 | 60586 |
| 400L | PX-400-GC-1 | 60593 | 60712 |
| 400L | PX-400-GC-2 | 60869 | 60819 |

The mass spectrometry results show that the estimate of the molecular weight of the protein in all the preparations is routinely approximately 60800 Dalton and remains consistent between batches produced from cells harvested from the 400 L bioreactor and 80 L bioreactors. This molecular weight is consistent with a glycosylated polypeptide having 506 amino acids contributing 56642.6 Dalton and the addition of the glycan structures contributing the remaining 4158 Dalton (ca. 7%).

Identification, Determination of Molecular Weight and Purity by SDS-PAGE and Western Blot Analysis:

The molecular weight identity and the protein impurity pattern of the glucocerebrosidase produced from cells harvested from the 400 L bioreactor were examined by SDS-PAGE analysis using Coomassie Brilliant blue staining.

FIG. 6 shows SDS-PAGE with Coomassie Brilliant blue staining of standard enzyme preparation (PLX-GC-016-0505 DS), Cerezyme and glucocerebrosidase produced from cells harvested from the 400 L Large Scale Disposable Bioreactor (PX-400-GC-2).

FIG. 6 further substantiates that prGCD from cells cultured in the Large Scale Bioreactor shows close to identical properties as GCD produced in other methods. The migration of the protein in each batch was similar, with an estimated molecular weight of 60.9 kD. Furthermore, the pattern of protein bands is identical between the batches from the standard and 400 L bioreactor, indicating no evidence of protein impurities in the enzyme produced from cells harvested from the 400 L bioreactor.

Immunodetection of the SDS-PAGE separated proteins (Western blot) with anti-glucocerebrosidase antibody was performed to identify the β-glucocerebrosidase molecules purified from cells harvested from the 400 L bioreactor in comparison to previously manufactured batches and to commercial human β-glucocerebrosidase (Cerezyme®, Genzyme) by using specific affinity purified anti-β-glucocerebrosidase antibodies.

FIG. 7 shows Western Blot analysis using specific rabbit anti-β-glucocerebrosidase antibodies for detection of standard β-glucocerebrosidase (PLX-GC-016-0505 DS), Cerezyme® and the protein produced from cells harvested from the 400 L bioreactor (PX-400-GC-2). The protein bands identified by the specific antibody are identical between the batches of the standard and 400 L bioreactor procedures. This analysis reveals no additional degraded bands in the enzyme protein produced from cells harvested from the 400 L bioreactor.

Thus, according to SDS-PAGE and immunological analysis, there is no evidence to indicate differences in the identity and purity between the enzyme produced from cells harvested from the standard (80 L) or from the 400 L bioreactor.

Peptide Mapping or Protein "Fingerprinting" Using Reverse Phase High Performance (Pressure) Liquid Chromatography (RP-HPLC):

In order to confirm the identity of the enzyme preparation produced in the standard production process (80 L) and from cells harvested from the 400 L bioreactor (PX-400-GC-2), protein fingerprinting was performed on prGCD produced from cells harvested from 80 and 400 L bioreactors.

FIGS. 8a and 8b show a typical profile of the tryptic map of commercial glucocerebrosidase (PLX-GC-016-0505 DS) performed on the C-18 chromatography column. FIG. 8a shows the separated peptides monitored at 214 nm (peptide bonds) and FIG. 8b shows the separated peptides monitored at 280 nm (Tryptophan and Tyrosine). FIGS. 8c and 8d represent the tryptic map of glucocerebrosidase prepared by from cells harvested from the 400 L bioreactor (PX-400-GC-2) monitored at 214 nm (FIG. 8c) and 280 nm (FIG. 8d).

Thus, the peptide map of glucocerebrosidase enzyme preparations from cells harvested from the Large Scale Disposable Bioreactor is identical with that of a standard preparation obtained with standard-scale technology, strongly indicating the consistency and identity of the enzyme preparations produced from cells harvested from the 80 L and 400 L bioreactor.

Reverse Phase High Performance (Pressure) Liquid Chromatography (RP-HPLC):

Further characterisation of the proteins produced by cells cultured in the 400 L Large Scale bioreactor was effected with RP-HPLC.

FIGS. 9a and 9b represent chromatograms at 214 nm (9a) and 280 nm (9b) of glucocerebrosidase purified from cells harvested from the 400 L bioreactor (PX-400-GC-2). In the chromatogram of enzyme protein produced in the Large Scale Disposable Bioreactor, the enzyme appears as one intact peak with retention time of 64.12 minutes, similar to the retention time of previously prepared glucocerebrosidase enzyme, 64.70 minutes.

Thus, under standard chromatographic conditions, recombinant glucocerebrosidase produced by both the Large Scale and standard scale Disposable Bioreactor eluted at a similar and consistent retention time. Appearance of one intact peak is consistent with the results obtained from the analysis performed on previous batches of enzyme preparations. The pattern and the size of the tiny impurity peaks are similar to a glucocerebrosidase standard, and the impurity level is within the required specifications.

Isoelectric Focusing (IEF):

In order to further identify, and to ensure the homogeneity of the recombinant protein produced by cells cultured in Large Scale bioreactor of the present invention, the pI range of Glucocerebrosidase banding profile from cells harvested from the Large Scale 400 L Bioreactor (PX-400-GC-2) and from cells harvested from standard 80 L reactor preparations (PLX-GC-016-0505DS) was determined.

FIG. 10 shows the pI banding pattern, visualized by Coomassie brilliant blue staining, of enzyme samples from standard volume bioreactor preparations (PLX-GC-016-0505DS) and from cells harvested from the 400 L bioreactor (PX-400-GC-2) at different stages of purification (after $3^{rd}$, $4^{th}$ and $5^{th}$ purification column, indicated by C-3, C-4 and C-5 respectively).

The profile of the enzyme produced by the standard volume bioreactor and from cells harvested from the 400 L bioreactor is identical in both the number of bands the pattern and the intensity of each analog band. Thus, the IEF isoform patterns of the enzyme produced in the Large Scale Disposable Bioreactor and previously produced preparations are identical.

Enzymatic Activity Assay:

To assess the catalytic activity of the recombinant glucocerebrosidase, produced in the Large Scale bioreactor, an enzymatic assay using the synthetic substrate-β-D-glucopyranoside (pNP-Glc) was employed. Table 5 summarizes the specific activity of glucocerebrosidase produced from cells harvested from the 400 L bioreactor (indicated by PX-400-GC) and by standard volume reactors.

TABLE 5

Specific activity of recombinant glucocerebrosidase batches

| Bioreactor Volume | Enzyme Batch No. | Specific Activity (Units/mg) |
| --- | --- | --- |
| 80L | PLX-GC-016-0505-DS | 41.53 |
| 80L | PLX-GC-016-Phenyl | 36.57 |
| 80L | PLX-GC-017-0705-DS | 33.04 |
| 80L | PLX-GC-017-Phenyl | 34.26 |
| 400L | PX-400-GC-1 | 33.30 |
| 400L | PX-400-GC-2 | 36.3 |

Thus, the specific activity of the enzyme produced from cells harvested from the 400 L bioreactor is in the range of that produced in standard scale production. Moreover, when comparing growth parameters of three lots of prGCD expressing cell cultures grown in the 800 liter bioreactor with values of cultures grown in 400 liter bioreactors, as is shown in Table 6 below, parameters of conductivity, osmolarity, and yield (cells and protein) were within the same range for cultures in the two Large Scale Disposable Bioreactors.

TABLE 6

Production Growth parameters of prGCD expressing cell culture in 400 and 800 L bioreactors

| | Batch analysis 400L | | | Batch analysis 800L | | |
| --- | --- | --- | --- | --- | --- | --- |
| Parameter | 31106 | 10107 | 20307 | 31106 | 10107 | 20307 |
| pH | 5.2 | 5.1 | 5.1 | 5.0 | 4.9 | 4.9 |
| Conductivity (ms/cm) | 5.7 | 5.6 | 5.3 | 5.5 | 5.7 | 5.2 |
| Osmolality (mOsm/kg H$_2$0) | 279 | 282 | 294 | 270 | 282 | 275 |
| Fresh weight (g cells/liter) | 55.0 | 48.0 | 56.3 | 54.4 | 50.3 | 55.0 |
| prGCD concentration at end point (mg prGCD/Kg cells) | 3.3 | 5.4 | 7.8 | 1.8 | 4.9 | 7.4 |

β-Glucocerebrosidase from Large Scale Disposable Bioreactor is Free of Host Cell Proteins:

For detection of carrot host cell proteins (CHP), a sensitive immunoassay capable of detecting a wide range of protein impurities has been developed. For this assay, a polyclonal antibody was generated by immunization with a protein preparation produced from non-transformed carrot cells (carrot cells not harboring the β-glucocerebrosidase construct). These polyclonal antibodies were further separated to give specific binding to the polypeptide core of the proteins and not to the sugar moieties/residues, for preventing cross-reaction with the sugars attached to the recombinant β-glucocerebrosidase.

Carrot host proteins (CHP) preparation is used as a reference standard for host related protein impurities and as an antigen for preparation of the polyclonal antibodies used for the immunoassay.

FIG. 11 shows the reactivity of the specific anti-host protein antibody to host protein samples and β-glucocerebrosidase batches analyzed by SDS-PAGE and Western Blot analysis with specific anti-carrot cell host protein antibodies. β-glucocerebrosidase batches (PLX-GC-016-0505 DS) from standard volume bioreactors, and β-glucocerebrosidase batches produced from cells harvested from the 400 L bioreactor (PX-400-GC-2) were analyzed as well as samples from the carrot host protein extract. Four major protein bands are identified in the carrot cell host protein samples (FIG. 11, lanes 7 and 8), however none of the corresponding CHP protein bands are detected in either of the β-glucocerebrosidase samples, indicating that recombinant β-glucocerebrosidase produced in Large Scale Disposable Bioreactors of the present invention contain undetectable levels of carrot host cell proteins, no less pure than the β-glucocerebrosidase manufactured by the standard volume production methods.

Example 3

Efficient Expression of Human Acetylcholinesterase in BY-2 Cell Suspension Using Large-Scale Disposable Bioreactor This Example provides a description of experiments that were performed with Nicotiana tabaccum BY-2 cells transformed with human acetylcholinesterase, cultured in a Large Scale Disposable Bioreactor according to one embodiment of the present invention.

Materials and Experimental Methods cDNA:

The cDNA encoding human acetylcholinesterase "read through" variant (AChE-R) inserted was obtained from Dr. Hermona Soreq, The Hebrew University of Jerusalem, Israel (Yissum Technology Transfer Company of the Hebrew University of Jerusalem, number pTM240). The sequence of this gene was plant optimized and includes the native leader sequence into the ER (33 amino acids at the N-terminal, SEQ ID NO: 7, degraded in the mature protein), and the ER retention sequence (SEKDEL; SEQ ID NO: 8) fused to the C-terminus of the recombinant gene (SEQ ID NO: 9).

Construction of Acetylcholinesterase Expression Plasmid—

The pBluescript SK+ plasmid (Cat. No 212205, Stratagene, La Jolla, Calif.) was used as the backbone for construction of the plant expression cassette. The plant expression cassette with the necessary elements required for high level expression was built into the pBluescript SK+ plasmid. This expression cassette (CE) includes the CaMV35S promoter, Omega translational enhancer, the transcription termination and polyadenylation signal of the *Agrobacterium tumefaciens* Octopine synthase gene (CE cassette).

AChE-R sub-cloned into the Bluescript® expression vector containing the expression cassette, by PCR amplification of AChE-R using primers containing Sal I and PstI restriction sites, depicted in bold underline (forward primer: 5'-CGGCGTCGACACAAGAGGCCTCCACAAT-3' (SEQ ID NO: 10) Reverse primer: 5'-CCCCCTGCAGCTAGAGTTCATCCTTCTC-3' (SEQ ID NO: 11) The expression cassette with AChE-R coding sequence was then removed from the intermediate vector and further subcloned using NotI and Acc651 into the binary vector pGREENII nos-Kana (Hellens et al., 2000), as described herein. Positive clones were selected using PCR and restriction analysis.

Transformation, Screening and Culturing of Ache-R Expressing BY-2 Cells:

Transformation of *Agrobacterium* prior to infiltration of BY2 cells was performed as previously described (den Dulk-Ras and Hooykaas, 1995). Kanamycin resistance, conferred by the NPTII gene driven by the nos promoter obtained together with the pGREEN vector, was used for screening and selection of transformants.

Infiltration with *Agrobacterium* of genetically modified *Nicotiana tabaccum* cells (line BY2) and subsequent culturing was effected essentially as described for transformation of carrot cells in Example 2 hereinabove. Screening for calli expressing high levels of Ache-R was effected with Elman's catalytic activity assay and Western blot, described herein. Cell suspension cultures of selected cells were maintained as 50 ml suspensions in 250 ml Erlenmeyers, in constant agitation and controlled temperature conditions, 25±2° C. on an orbital shaker (80 rpm). The production process included a growth phase in medium containing the antibiotics Paromomycin and Cefotaxime as selective agents.

Scal-Up of Culture Growth in a Bioreactor:

The scale-up of the culture to 10 L was done gradually. First an inoculum of 200-400 mL cell suspension was introduced into a 12 L bio-reactor containing 3.6-9.8 L of Medium. Following 7 days of cultivation (25±2° C., 1.5 Lpm of sterile air), medium was added up to 10 L and cultivation continued under the same conditions for another 7 days. The 400 L bioreactor was inoculated with 10 L of suspension cells and subsequently gradually filled with medium to up to 350 L, continuing cultivation under the same conditions.

Antifoam (10 ppm) was added to the cell growth media when transferred to the 400 L. The antifoam used is Medicinal Antifoam C Emulsion (Polydimethylsiloxane-PDMS) as described herein.

Western Blot:

Western blot was effected with an affinity purified goat polyclonal antibody raised against a peptide at the N-terminus of AChE of human origin (Santa-Cruz Biotechnology, Santa Cruz, Calif.). The N-terminus is identical in all forms of AChE, thus, this antibodies can recognize AChE-R as well. Detection was preformed with ECL detection kit (Pierce).

SDS-PAGE was performed under standard conditions. AChE-S and AChE-R were analyzed on 10% SDS-PAGE. Electrophoresis is performed using Criterion™ cell vertical electrophoresis apparatus (Bio-Rad Laboratories) with premixed electrophoresis Tris-Glycine-SDS running buffer (Bio-Rad Laboratories). 10% acrylamide gels were prepared using premixed solutions of 40% Acrylamide/Bis and 10% SDS solution. Transfer of proteins from bis-acrylamide gels to nitrocellulose membrane was performed using iBlot™ Dry Blotting System (Invitrogen), using the blotter P3 ready plan. Transfer was performed at room temperature for 8 min. Following transfer of proteins to the membrane, membrane was blocked, washed, bound to the primary and secondary antibody using One-step™ Complete Western Kit (GenScript Corporation). Primary antibody (N-19; Santa Cruz, Calif.) was added into the One-step™ (GenScript) working solution in 1:200 dilutions. Detection was performed with ECL detection kit (Pierce). The immunoreactivity of AChE-R was compared to that of commercial human recombinant AChE-S (Sigma). Bands were detected using the Molecular Imager Gel Doc XR System (Bio-Rad Laboratories).

Flamingo™ Fluorescent Gel Stain:

Flamingo™ fluorescent gel stain (Bio-Rad Laboratories), is a highly sensitive, non-specific protein staining method. AChE-R (batch 9-11) were loaded at several concentrations (50, 100 and 200 ng/sample) in comparison to commercial human recombinant AChE-S (Sigma). Samples were analyzed on 10% SDS-PAGE under standard procedure as described herein, and stained with Flamingo™ fluorescent gel stain according to manufacturer's instructions.

Ellman's Assay:

Ellman's reagent is used for the modification of free thiols in proteins (Ellman, et al. 1961). It rapidly forms a disulfide bond with the thiol and releases a thiolate ion, which has a characteristic color, which can be measured at 405 nm. Ellman's assay was effected for measuring AChE-R activity and concentration of active enzyme in crude homogenate samples, as well as to determine the concentration of active enzyme in purified samples. An enzyme unit is defined as the amount of enzyme that catalyzes the hydrolysis of one micromole of the synthetic substrate acetylthiocholine iodide [(2-mercaptoethyl) trimethylammonium iodide acetate] to (2-mercaptoethyl)trimethylammonium iodide and acetic acid per minute at room temperature and pH=7.4. The catalytic activity of AChE-R was determined using acetylthiocholine iodide (Sigma, St Louis Mo.) as a substrate. Samples were examined for AChE catalytic activity at concentrations of about 60 ng/ml (purified sample) or 50-100 ng/ml (crude homogenate) and were dissolved in a phosphate buffer (0.1M; pH=7.4; 0.025% BSA) following the spectrophotometric method developed by Ellman et al.

(1961). In this method, AChE, acetylthiocholine iodide (20 mM) and Ellman's regaent-DTNB [5-5'-dithio-bis(2-nitrobenzoate); 9 mM; Sigma] were mixed and hydrolysis was monitored spectrophotometrically by measuring optical density at 405 nm at 2 min intervals for 20 min. Negative controls contained all components except the tested extract. Results plotted against time and initial rates were calculated from the slope of the linear portion of the graph.

The unit activity of each AChE preparation is calculated using the following equation:

$$\text{Unit/ml} = \frac{\text{slope\_AChE}\left(\frac{\Delta OD}{\min}\right)}{13{,}600\left(\frac{1}{MX\,\text{cm}}\right)X\,0.5\text{ cm}} \times 100 \text{ (µmole)} \times F(\text{Dilution})$$

Ellman's Reagent Using a Specific AChE Inhibitor—DEPQ:

DEPQ [7-(O,O-diethyl-phosphinyloxy)-1-methylquinolinium methylsulfate] is a potent non-reversible inhibitor of AChE and it is used for monitoring its activity. Active site titration of enzyme solutions was performed in the presence of phosphate buffer (0.1M; pH=7.4; 0.025% BSA) by adding various amounts of DEPQ (0.2-0.8 nM). Activity was measured using the Ellman's assay as described above. Percentage of inhibition was plotted against the concentration of inhibitor. DEPQ reacts in a 1:1 ratio with AChE-R. These values were used to determine AChE-R concentration, expressed in µM.

Cholinesterase Activity Using Karnovsky Staining:

Karnovsky and Roots cholinesterase activity staining (Karnovsky and Roots, 1964) is a specific method used to visually detect cholinesterase (AChE and BChE) activity. This method utilizes thiocholine esters as substrates, and is based on the reduction of ferricyanide to ferrocyanide by thiocholine released by cholinesterase activity. The ferrocyanide formed is captured by copper to form copper ferrocyanide, which is then visualized by the naked eye.

Native (Non-Denaturing) PAGE:

Native polyacrylamide gel electrophoresis (PAGE) is used for proteins ranging in size from 5 to 2,000 kDa due to the uniform pore size provided by the polyacrylamide gel. Unlike SDS-PAGE, native gel electrophoresis does not use a charged denaturing agent. The molecules being separated, therefore, differ in molecular mass and intrinsic charge. Since the proteins remain in the native state throughout separation, they may be detected not only by general protein staining reagents but also by reagents employing specific catalytic properties of the enzyme.

Results

Recombinant Ache-R Profile:

The recombinant AChE-R protein produced by the methods of the present invention is estimated at molecular weight of 64 kDa, as shown in FIG. 15 (lanes 1-3). Control AChE-S (lanes 5-7), a tetramer under neutral conditions, was reduced in the SDS-PAGE to its monomers, and thus migrated similarly to AChE-R, since the AChE-S monomer is about 70 kDa, 6 kDa heavier than AChE-R. Thus, AChE-R expressed in BY2 tobacco cells in the Large Scale Disposable Bioreactor has similar 3 dimensional structure (as determined by electrophoretic mobility) to the recombinant human AChE-S expressed in HEK 293 cells (Sigma) in its monomeric form.

Flamingo™ non-specific staining additionally verifies the recombinant, plant expressed AChE-R migration profile, as the detected bands exhibit the same migration pattern as was detected by immunoassay using anti AChE antibodies (FIG. 16). Furthermore, the single staining band observed on the gel as shown in FIG. 16 indicates significant efficiency of purification of the plant-expressed enzyme protein.

Recombinant AChE-R Activity:

FIG. 17 shows the catalytic identity of the plant-expressed AChE-R and mammalian-cell expressed AChE-S polypeptides, using Karnovsky stain. 50 ng (lanes 3 and 6), 100 ng (lanes 2 and 5) and 200 ng (lanes 1 and 4) AChE-R were loaded on the gel. Activity was evident in all 3 loading concentrations, confirming activity of the Ache-R purified from BY-2 cells harvested from the Large Scale bioreactor of the present invention. Commercial human recombinant AChE-S appears in its tetramer form (see upper arrow), thus migrating slower than the AChE-R monomers (lower arrow) and remained its activity. The less pronounced band detected in lanes 4-6, migrating identically to that of AChE-R monomers (lanes 1-3) indicates that the plant-expressed AChE-S monomers are not only identical in size, but equally catalytically active with the commercial human recombinant AChE-S.

Table 7 below shows a comparison of plant-expressed AChE-R activity and concentration in batchs produced in small volume bioreactors and those produced in Large Scale Disposable Bioreactor according to an embodiment of the present invention, as tested by Ellman's activity assay using DEPQ inhibition. Table 7 clearly shows significantly increased yields of AChE protein (expressed as mg protein/Kg cells) in the Large Scale culturing device, without reduction in range of enzymatic activity.

|  | U = 1 nmole (Ellman) | yield (mg protein/ Kg cells wet weight) | mg/ml |
|---|---|---|---|
| 10 L bioreactor (batch 6) | 429.6 | 0.38 | 2.2 |
| 10 L bioreactor (batch 67) | 489.3 | 0.48 | 1.8 |
| 400 L (batch 8) | 535 | 0.68 | 1.62 |
| 400 L (batch 9-11) | 564 | 0.66 | 1.16 |

Thus, taken together these result further support the significant advantages of culturing transgenic plant cells in the Large Scale Disposable Bioreactor according to some embodiments of the present invention for accurate and highly efficient expression and post-translational processing of recombinant proteins, while avoiding many of the disadvantages of smaller volume and animal-based expression systems.

REFERENCES

Ma, J. K. C., Drake, P. M. W., and Christou, P. (2003) *Nature reviews* 4, 794-805

US Patent Application No. 2005/0282269 to Proulx et al.

US Patent Application No. 2005/0272146 to Hodge et al

U.S. Pat. No. 6,432,698 to Gaugler et al.

Schlatmann et al, Biotech. Bioeng., 1995; 45:435-39

Namdev and Dulop, App. Biochem and Biotech, Part A, Frontiers in Bioprocessing, 1995

What is claimed is:

1. A disposable device for culturing and harvesting plant tissue and/or cells comprising a non-rigid container having a volume of at least 400 liters and being configured with gas exchange ports and a harvesting port enabling said device to be used continuously for at least two consecutive culturing/harvesting cycles, wherein said gas exchange ports include a plurality of gas inlet ports positioned around the perimeter of the container in the lower half of the container, the outlets of said ports into the container having exits into the container that are spaced from an axis of the container and wherein the device has neither mechanical agitation to mix medium in the container or a sparger to distribute gas bubbles when medium is present therein.

2. The device of claim 1, wherein said harvesting port is located at the bottom of said bottom end of the container.

3. The device of claim 1, wherein said bottom end is substantially frusta-conical.

4. The disposable device of claim 1, wherein the plurality of gas inlet ports are distributed in the lower half of the volume with a density of 20 to 70 inlets per cross sectional area of the container in square meters.

5. A plant cell culturing system comprising the device of claim 1 and culture medium suitable for culturing said plant tissue and/or cells.

6. The plant cell culture system of claim 5, further comprising a plant cell suspension or tissue culture growing in said medium.

7. The plant cell culture system of claim 6, wherein said plant cells express a recombinant protein.

8. The plant cell culture system of claim 6, wherein said plant cells are selected from the group consisting of *Agrobacterium rihzogenes* transformed root cells, celery cells, ginger cells, horseradish cells, tobacco cells and carrot cells.

9. The plant cell culture system of claim 6, wherein said cells are tobacco cells expressing human recombinant acetylcholinesterase.

10. The plant cell culture system of claim 9, wherein said human recombinant acetylcholinesterase is acetylcholinesterase-R.

11. The disposable device of claim 1, wherein the container is formed with an inverted conical lower portion and wherein the first plurality of said ports is positioned on said conical portion.

12. The disposable device of claim 1, wherein a portion of said container has a generally uniform cross section and wherein a plurality of gas exits into the medium is provided at a density of gas inlets per cross sectional area of about 20 inlets per square meter to about 70 inlets per square meter.

13. The disposable device of claim 1, and including a gauge for controlling an aeration rate of about 0.05-0.12 volumes gas per volume medium per minute when said container is filled to its fillable volume.

14. The disposable device of claim 1, wherein each of the plurality of gas ports is shaped to provide a gas bubble volume at exit into the medium of about 20 cubic millimeters to about 1800 cubic millimeters.

15. The disposable device of claim 1, wherein said harvesting port is below the level of at least one said inlet port.

16. The plant cell culturing system of claim 5, wherein the exits are adjacent the perimeter of the container at the position of the ports.

17. The plant cell culturing system of claim 5 wherein the container is generally cylindrically symmetrical and a ports of first plurality are positioned at a same first distance from a bottom of the container, and spaced from each other.

18. The plant cell culturing system of claim 5, wherein the container is formed with an inverted conical lower portion and wherein a first plurality of said plurality of inlet ports are positioned on said conical portion.

19. The plant cell culturing system of claim 18, wherein ports of a second plurality of said plurality of gas inlet ports are positioned at a same second distance from a bottom of the container, and spaced from each other, said second distance being different from said first distance.

20. The plant cell culturing system of claim 18, wherein the second plurality of said plurality of gas inlet ports is positioned on said conical portion such that the distance from the axis of the container is different for the first and second plurality of ports.

21. The plant cell culturing system of claim 5, wherein different ones of said plurality of gas inlet ports are positioned at different distances from a bottom of the container.

22. The plant cell culturing system of claim 5, wherein a portion of said container has a generally uniform cross section and wherein a plurality of said gas exits into the medium; is provided at a density of gas inlets per cross sectional area of about 20 inlets per square meter to about 70 inlets per square meter.

23. The plant cell culturing system of claim 5, and including a gauge for controlling an aeration rate of about 0.05-0.12 volumes gas per volume medium per minute when said container is filled to its fillable volume.

24. The plant cell culturing system of claim 5, wherein each of the plurality of gas inlet ports provides a gas bubble volume at exit into the medium of about 20 cubic millimeters to about 1800 cubic millimeters.

25. A disposable device for culturing and harvesting plant tissue and/or cells comprising a non-rigid container having a volume of at least 400 liters and being configured with gas exchange ports and a harvesting port enabling said device to be used continuously for at least two consecutive culturing/harvesting cycles, wherein said gas exchange ports include a plurality of gas inlet ports positioned around the perimeter of the container in the lower half of the container, the outlets of said ports into the container having exits into the container that are spaced from an axis of the container; and
wherein the device has neither mechanical agitation to mix medium in the container or a sparger to distribute gas bubbles when medium is present therein; and
the exits are adjacent the perimeter of the container at the position of the ports; and
wherein the container is generally cylindrically symmetrical and ports of a first plurality of said plurality of gas inlet ports are positioned at a same first distance from a bottom of the container and spaced from each other.

26. The disposable device of claim 25, wherein different ones of said plurality of gas inlet ports are positioned at different distances from a bottom of the container.

27. The disposable device of claim 25, wherein ports of a second plurality of said plurality of gas inlet ports are positioned at a same second distance from a bottom of the container, and spaced from each other, said second distance being different from said first distance.

28. The disposable device of claim 25, wherein the container is formed with an inverted conical lower portion and wherein the first plurality of said ports is positioned on said conical portion.

29. The disposable device of claim 26, wherein the container is formed with an inverted conical lower portion and wherein said ports is positioned on said conical portion.

30. The disposable device of claim 29, wherein the second plurality of said plurality of gas inlet ports is positioned on said conical portion such that the distance from the axis of the container is different for the first and second plurality of gas inlet ports.

31. A method for culturing and harvesting a plant tissue and/or plant cells in a volume greater than 400 liters, the method comprising:

(a) providing a disposable non-rigid container having a volume of at least 400 liters and being configured with gas exchange ports and a harvesting port enabling said device to be used continuously for at least two consecutive culturing/harvesting cycles, wherein the device is designed and constructed for maintaining oxygen saturation and shear forces suitable for culturing said plant tissue and/or cells; and
(b) providing inoculant via said harvesting port;
(c) providing sterile culture medium and/or sterile additives;
(d) optionally illuminating said container with external light; and
(e) allowing said cells and/or tissue to grow in said medium to a desired yield; and
said gas exchange ports include a plurality of gas inlet ports and the method includes positioning said around the perimeter of the container in the lower half of the container, the outlets of said ports exiting into the container being provided at positions that are spaced from an axis of the container and wherein gas is distributed within the container without sparging or mechanical agitation of the medium and wherein the container is generally cylindrically symmetrical and ports of a first plurality of said plurality of gas inlet ports are positioned at a same first distance from a bottom of the container and spaced from each other.

32. The method of claim 31, and including:
a) providing gas at a gas pressure of about to 1 bar to 5 bar;
b) providing a density of gas inlets per cross sectional area of a generally uniform portion of the container of about 20 inlets per square meter to about 70 inlets per square meter;
c) providing gas at an aeration rate about 0.05 to 0.12 volumes gas per volume medium per minute; and
d) providing said gas as bubbles having a gas bubble volume at said outlets of about 20 cubic millimeters to about 1800 cubic millimeters.

33. The method of claim 32, providing said gas at rate to provide a steady state oxygen saturation of at least 15% volume per volume in a liquid contained within said container.

34. The method of claim 32, wherein said gas is provided at a gas pressure of about 1.5 bar to about 2.5 bar.

35. The method of claim 32, wherein a portion of said container has a generally uniform cross section and wherein said density of gas inlets per cross-sectional area is about 40 per square meter to about 60 per square meter.

36. The method of claim 32, wherein said aeration rate is about 0.07 to 0.10 volumes gas per volume medium per minute.

\* \* \* \* \*